US009526794B2

(12) United States Patent
Rangaramanujam et al.

(10) Patent No.: US 9,526,794 B2
(45) Date of Patent: Dec. 27, 2016

(54) INJECTABLE DENDRIMER HYDROGEL NANOPARTICLES

(75) Inventors: Kannan Rangaramanujam, Detroit, MI (US); Sujatha Kannan, Detroit, MI (US); Roberto Romero, Detroit, MI (US); Raghavendra Navath, Somerset, NJ (US); Anupa Menjoge, Hayward, CA (US)

(73) Assignees: Wayne State University, Detroit, MI (US); National Institutes of Health, Bethesda, MD (US)

( * ) Notice: Subject to any disclaimer, the term of this patent is extended or adjusted under 35 U.S.C. 154(b) by 627 days.

(21) Appl. No.: 13/636,715

(22) PCT Filed: Mar. 31, 2011

(86) PCT No.: PCT/JP2011/030648
§ 371 (c)(1),
(2), (4) Date: Nov. 30, 2012

(87) PCT Pub. No.: WO2011/123591
PCT Pub. Date: Oct. 6, 2011

(65) Prior Publication Data
US 2013/0136697 A1    May 30, 2013

Related U.S. Application Data

(60) Provisional application No. 61/319,289, filed on Mar. 31, 2010.

(51) Int. Cl.
*A61K 47/48* (2006.01)
*C08L 79/02* (2006.01)
*C08G 73/02* (2006.01)

(52) U.S. Cl.
CPC ... *A61K 47/48207* (2013.01); *A61K 47/48784* (2013.01); *C08G 73/028* (2013.01); *C08L 79/02* (2013.01)

(58) Field of Classification Search
None
See application file for complete search history.

(56) References Cited

U.S. PATENT DOCUMENTS 5,714,166 A    2/1998  Tomalia et al.
2002/0192843 A1  12/2002  Kaganove et al.
(Continued)

FOREIGN PATENT DOCUMENTS

WO    WO2004041310        5/2004
WO    WO 2008068531 A2 *  6/2008
WO    WO2010017184 A2     2/2010

OTHER PUBLICATIONS

Wu et al. Preparation and Characterization of Novel Physically Cross-linked Hydrogels Composed of Poly (vinyl alcohol) and Amine-terminated Polyamidoamine Dendrimer. Macromolecular bioscience 4.2 (2004): 71-75.*
(Continued)

*Primary Examiner* — Nissa Westerberg
(74) *Attorney, Agent, or Firm* — Pabst Patent Group LLP

(57) ABSTRACT

The invention discloses injectable hydrogels which are in the form of crosslinked nano beads or particle in the size range 5 nm to 10 μm, comprising PAMAM dendrimer with asymmetrical peripheral end groups such that one of the terminal groups is involved in formation of hydrogel and the other in involved in the conjugation of drugs or imaging agents and their methods of preparation. The said gel is formed by reaction of the PAMAM dendrimer with asymmetrical end groups with other polymer wherein the other polymer is selected from the group of linear, branched, hyperbranched or star shaped polymers with functionalized terminal groups. The PAMAM dendrimer with asymmetrical terminal groups consists of a Generation 2 and above PAMAM dendrimer with symmetrical end groups modified using the amino acids or their modified forms. The gel
(Continued)

disclosed in the present invention is formed as small cross-linked particles in the size range 25 nm to 10 μm and is suitable for injectable delivery of hydrogel to any of the body orifices, tissues by intramuscular or subcutaneous route and ocular delivery for the purpose of therapeutic treatment and imaging.

11 Claims, 41 Drawing Sheets

(56) References Cited

U.S. PATENT DOCUMENTS

| 2003/0135005 | A1 | 7/2003 | Houser et al. | |
|---|---|---|---|---|
| 2006/0041058 | A1 | 2/2006 | Yin et al. | |
| 2006/0240110 | A1* | 10/2006 | Kiick et al. | 424/486 |
| 2007/0128681 | A1 | 6/2007 | Barman et al. | |
| 2007/0298006 | A1 | 12/2007 | Tomalia et al. | |
| 2009/0104123 | A1* | 4/2009 | Yang | A61K 49/0002 424/9.3 |

OTHER PUBLICATIONS

Navath et al. Bioconjugate Chemistry, 19, p. 2446-2455, 2008.*
Mishra et al., Journal of Biomaterials Science 20, p. 141-166, Feb. 2009.*
Li et al., Journal of Controlled Release 56, p. 117-126, 1998.*
Wu et al., Macromolecuar Bioscience, 4, p. 71-75, 2004.*
Viers et al. Polymer Preprints, 41(1), 729, 2000.*
Lee et al., Bioconjugate Chemistry, 18, p. 579-584, 2007.*
Antoni, et al., "Bifunctional dendrimers: from robust synthesis and accelerated one-pot post functionalization strategy to potential applications," Angew Chern Int Ed Engl, 48, (12),2126-30, 2009.
Antoni, P., et al, "A chemoselective approach for the accelerated synthesis of well-defined dendritic architectures," Chem Commun (Camb) 2007, (22), 2249-51.
Brauge, L., et al, "First divergent strategy using two AB(2) unprotected monomers for the rapid synthesis of dendrimers," J Am Chem Soc 2001.
Chow, H., et al, "Synthesis and Characterization of Outer Sphere—Outer Sphere Connected Organoplatinum Dendritic Networks from Surface-Difunctionalized and Surface-Trifunctionalized Dendritic Monomers," Macromolecules 2004,37, (10), 3595-3605.
Darbre, T., et al, "Peptide Dendrimers as Artificial Enzymes, Receptors, and Drug-Delivery Agents," Accounts of Chemical Research 2006, 39, (12), 925-934.
Duncan, R., et al., "Dendrimer biocompatibility and toxicity," Adv Drug Deliv Rev 2005,57, (15),2215-37.
Fischer-Durand, N., et al, "Design of a New Multifunctionalized PAMAM Dendrimer with Hydrazide-Terminated Spacer Arm Suitable for Metal-Carbonyl Multilabeling of Aldehyde-Containing Molecules," Macromolecules 2007, 40, (24), 8568-8575.
Fuchs, S., et al., "A surface-modified dendrimer set for potential application as drug delivery vehicles: synthesis, in vitro toxicity, and intracellular localization," Chemistry 2004, 10, (5), 1167-92.
Gillies, E. R., et al., "Designing Macromolecules for Therapeutic Applications: Polyester Dendrimer-Poly(ethylene oxide) "Bow-Tie" Hybrids with Tunable Molecular Weight and Architecture," Journal of the American Chemical Society 2002, 124, (47), 14137-14146.
Goodwin, et al., "Efficient Synthesis of Heterobifunctional Biodegradable Dendrimers," Journal of the American Chemical Society 129, (22), 6994-6995, 2007.
Goyal, P., et al., "Multifunctionalization of dendrimers through orthogonal transformations," Chemistry2007, 13, (31), 8801-10.
Han, et al., "Multifunctional Dendrimer-Templated Antibody Presentation on Biosensor Surfaces for Improved Biomarker Detection," Adv. Funct. Mater. 20, 409-421, 2010.

Kaminskas, L. M., et al., "The impact of molecular weight and PEG chain length on the systemic pharmacokinetics of PEGylated poly I-lysine dendrimers," Mol Pharm 2008, 5, (3), 449-63.
Kannan, S., et al, "Effect of dendrimer end functionality on the cytotoxicity and the cellular drug delivery in lung epithelial cells," Journal of Biomaterials Science: Polymers Edition 2004, 15, 311-330.
Khandare, J., et al., "Synthesis, cellular transport, and activity of polyamidoamine dendrimer methylprednisolone conjugates," Bioconjug Chem 2005, 16, (2), 330-7.
Kitchens, K. M., et al., "Transepithelial and endothelial transport of poly (amidoamine) dendrimers," Adv Drug Deliv Rev 2005, 57, (15), 2163-76.
Kobayashi, H., et al., "Renal tubular damage detected by dynamic micro-MRI with a dendrimer-based magnetic resonance contrast agent," Kidney Int 2002, 61, (6), 1980-1985.
Kobayashi, H., et al., "Dynamic micro-magnetic resonance imaging of liver micrometastasis in mice with a novel liver macromolecular magnetic resonance contrast agent DAB-Am64-(1 B4M-Gd)(64)," Cancer Res 2001, 61, (13), 4966-4970.
Kolhatkar, R B., et al. "Surface acetylation of polyamidoamine (PAMAM) dendrimers decreases cytotoxicity while maintaining membrane permeability," Bioconjug Chem 2007, 18, (6), 2054-60.
Kolhe, et al., "Drug complexation, in vitro release and cellular entry of dendrimers and hyperbranched polymers," Int J Pharm 259, (1-2), 143-60, 2003.
Kono, K., et al, "Transfection activity of polyamidoamine dendrimers having hydrophobic amino acid residues in the periphery," Bioconjug Chem 2005, 16, (1),208-14.
Kurtoglu, et al., "Poly(amidoamine) dendrimer-drug conjugates with disulfide linkages for intracellular drug delivery," Biomaterials, 30, (11), 2112-21, 2009.
Lee, et al., "Designing dendrimers for biological applications," Nat Biotech 23, (12), 517-26, 2005.
Lim, J., Simanek, E.E., "Synthesis of water-soluble dendrimers based on melamine bearing 16 paclitaxel groups," Organic Letters 2008, 10, 201-204.
Majoros, I. J., et al., "Acetylation of Poly(amidoamine) Dendrimers," Macromolecules 2003, 36, (15), 5526-5529.
Majoros, I. J., et al., "Poly(amidoamine) dendrimer-based multifunctional engineered nanodevice for cancer therapy," J Med Chern 2005,48, (19), 5892-9.
Malik, N., et al., "Dendrimers: relationship between structure and biocompatibility in vitro, and preliminary studies on the biodistribution of 125I-labelled polyamidoamine dendrimers in vivo," J Control Release 2000,65, (1-2), 133-48.
Menjoge et al., "Dendrimer-based drug and imaging conjugates: design considerations for nanomedical applications," Drug Discov Today. 15:171-185, 2010.
Mulders, S. J. E., et al., "Synthesis of a novel amino acid based dendrimer," Tetrahedron Letters 1997, 38, (4), 631-634.
Navath, et al., "Amino Acid-Functionalized Dendrimers with Heterobifunctional Chemoselective Peripheral Groups for Drug Delivery Applications," Biomacromoleculas Apr. 26, 2010.
Navath, et al., "Dendrimer-drug conjugates for tailored intracellular drug release based on glutathione levels," Bioconjug Chem 19, (12), 2446-55, 2008.
Oh, S.-K., et al., "Synthesis, Characterization, and Surface Immobilization of Metal Nanoparticles Encapsulated within Bifunctionalized Dendrimers," Langmuir2003, 19, (24), 10420-10425.
Okuda, et al., "Biodistribution characteristics of amino acid dendrimers and their PEGylated derivatives after intravenous administration," J Control Release 114, (1), 69-77, 2006.
Paleos, C. M., et al., "Acid- and salt-triggered multifunctional poly(propylene imine) dendrimer as a prospective drug delivery system," Biomacromolecules 2004,5, (2), 524-9.
Patil, M. L., et al., "Internally cationic polyamidoamine PAMAM-OH dendrimers for siRNA delivery: effect of the degree of quaternization and cancer targeting," Biomacromolecules 2009, 10, (2), 258-66.
Qi, R., et al, "PEG-conjugated PAMAM Dendrimers Mediate Efficient Intramuscular Gene Expression," Aaps J 2009.
Saad, M., et al., "Receptor targeted polymers, dendrimers, liposomes: which nanocarrier is the most efficient for tumor-specific treatment and imaging?" J Control Release 2008, 130, (2),107-14.

(56) References Cited

OTHER PUBLICATIONS

Sato, et al., "Tumor targeting and imaging of intraperitoneal tumors by use of antisense oligo-DNA complexed with dendrimers and/or avidin in mice," Clin Cancer Res 7, (11), 3606-12, 2001.

Sivanandan, K., et al., "Functional group diversity in dendrimers," Org Lett 2002, 4, (21), 3751-3.

Steffensen, M. B., Simanek, E.E., "Synthesis and manipulation of orthogonally protected dendrimers: building blocks for library synthesis," Angew. Chem. 2004, 116, 5290-5292.

Svenson, "Dendrimers in biomedical applications—reflections on the field," Adv Drug Deliv Rev 57:2106-29, 2005.

Tolic, L. P., et al., "Electrospray ionization Fourier transform ion cyclotron resonance mass spectrometric characterization of high molecular mass Starburst™ dendrimers," Int J of Mass Spectrometry and Ion Processes, 1997, 165-166, 405-418.

Tomalia, et al., "Dendrimers as multi-purpose nanodevices for oncology drug delivery and diagnostic imaging," Biochemical Society Transactions 35, 61- 67, 2007.

Waite, C. L., et al., "Acetylation of PAMAM dendrimers for cellular delivery of siRNA," BMC Biotechno/2009, 9, 38.

Woller, E. K.; Cloninger, M. J., "The lectin-binding properties of six generations of mannose-functionalized dendrimers," Org Lett 2002,4, (1), 7-10.

Wu, P., et al., "Multivalent, bifunctional dendrimers prepared by click chemistry," Chem Commun (Camb) 2005, (46), 5775-7.

Search report dated Jun. 22, 2011 for PCT/US2011/30648.

Baek, et al., "Synthesis and Protein Binding Properties of T-Antigen Containing GlycoPAMAM Dendrimers", Bioorganic & Medicinal Chemistry, 2002, vol. 10 (1), pp. 11-17.

Desai, et al.,"Synthesis and Characterization of Photocurable Polyamidoamine Dendrimer Hydrogels as a Versatile Platform for Tissue Engineering and Drug Delivery", Biomacromolecules, vol. 11, No. 3, 2010, pp. 666-673.

Kannan, S., et al, "Dynamics of Cellular Entry and Drug Delivery by Dendritic Polymers into Human Lung Epithelial Carcinoma Cells," Journal of Biomaterials Science: Polymers Edition 2004, 15, 311-330.

Kurtoglu, et al., "Drug Release Characteristics of PAMAM Dendrimer-Drug Conjugates with Different Linkers", International Journal of Pharmaceutics, 2010, vol. 384 (1-2), pp. 189-194.

Liu, et al., "Dendrinneric Pyridoxamine Enzyme Mimics" Journal of the American Chemical Society, 2003, vol. 125 (40), pp. 12110-12111.

Menjoge, et al., "Transport and biodistribution of dendrimers across human fetal membranes: Implications for intravaginal administration of dendrimer-drug conjugates," Biomaterials 31 (2010) 5007-5021.

Search Report Dated Jul. 30, 2014 in European Application No. 11763407.1.

Unal, et al., "Gelation and Swelling Behavior of End-Linked Hydrogels Prepared from Linear Poly(Ethylene Glycol) and Poly(Amidoamine) Dendrimers" Polymer, 2006, vol. 47 (24), pp. 8173-8182.

* cited by examiner

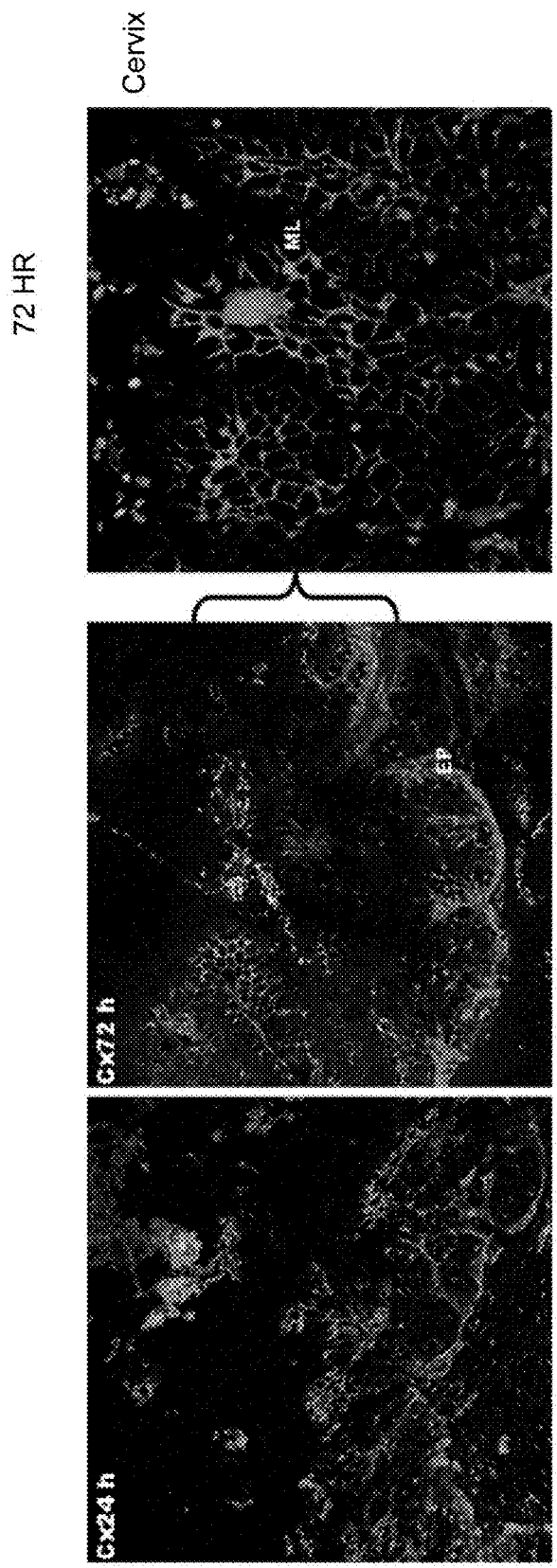

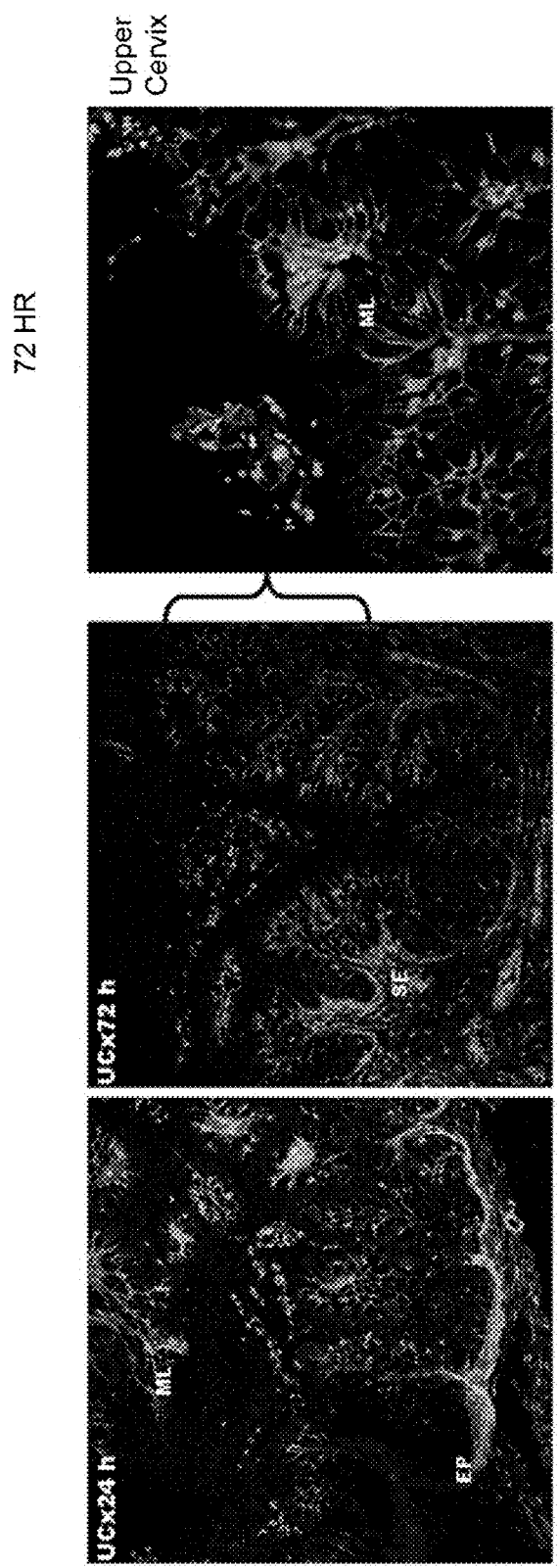

INJECTABLE DENDRIMER HYDROGEL NANOPARTICLES

BACKGROUND OF THE INVENTION

1. Field of the Invention

Generally, the present invention relates to the field of therapeutic agents. More specifically, the present invention relates to a hydrogels containing therapeutic agents.

2. Description of the Related Art

Dendrimers are a class of well-defined nanostructured macromolecules with narrow polydispersity, and a multivalent surface amenable for further modifications. Dendrimers are extensively and continually investigated for biomedical applications such as gene therapy, drug delivery and bioimaging purposes. As nanocarriers, dendrimers have the versatility to allow conjugation, complexation, and/or encapsulation of multifunctional moieties. The functional groups on the periphery of dendrimer act as highly accessible handles for drug or other functional group attachments. Since the functionalities of the drugs and ligands are diverse, there is a need to explore multiple functional group presentations at the dendrimer surface. Adding diverse functional moieties (drugs or imaging agents) onto a single dendrimer is difficult because all the peripheral groups of the symmetric dendrimer have the same reactivity. A suitable linker or spacer is required to react with the surface functionality of dendrimer, which offers the flexibility to link multiple moieties-such as drugs, imaging or targeting agents.

Functionalization of dendrimers has enabled several end objectives like reduction in cytotoxicity, targeted drug delivery, formation of hydrogels, increase plasma residence time, imaging, in-vivo biodegradation, or potentially any combination of these. For example, modification of G4 dendrimers with 19, 29, 46 molecules of phenylalanine resulted in improved gene transfection ability, while modification with 64 molecules of phenylalanine resulted in poorly soluble compounds with loss in DNA complexing ability. Widespread use of cationic dendrimers in drug and gene delivery is hindered by their cytotoxicity. PEGylation and acetylation are highly successful approaches in overcoming the cytotoxicity of amine terminated dendrimers but the higher degree of amine neutralization compromises its gene slicing efficiency. The dendrimer surface modification should therefore be such that several end objectives are met without compromising on any attributes and yet having chemically reactive groups suitable for modifications to attach drug or targeting moieties. There is a need to develop new methodologies for synthesis of functionalized dendrimers that involve fewer reaction steps, achieve high yields, are compatible with a variety of functional groups, and occur under mild reaction conditions offering clean and efficient synthesis.

To make dendrimers as efficient delivery vectors, apart from multivalency there is a need to have unique orthogonal end groups for chemoselective surface modifications and multi-functionalization. There are studies described in the literature for development of hetero-bifunctional dendrimers. However, the research into development of such dendrimers for biomedical applications is not extensive. The dendrimer synthesis requires elaborate steps, and is expensive, thereby limiting the commercial availability to PAMAM, DAB, Phosphorous PMMH and 2,2-bis(methylol) propionic acid (bis-MPA) dendrimers. There have been few reports on the synthesis of dendrimers bearing different asymmetric groups at the periphery. It is reported that to obtain a total of 32 (16+16) and 48 (24+24) reactive groups on the generation 4 dendrimer several sequential steps were required. Previously, melamine dendrimers with orthogonal reactive groups on surface comprising 4 hydroxyl groups, 4 hydroxyl groups masked as tert-butyldiphenylsilyl ether and 16 tert-Butoxycarbonyl protected amines was synthesized in eight total steps with a 55% overall yield. An efficient method to synthesize dendrimers with orthogonal peripheral groups is to grow a symmetric dendrimer in bulk and then tune its periphery for the desired application. However, this process requires that the subsequent differentiation and coupling steps be minimal in number and efficient in reactivity.

Functionalization of the peripheral groups of dendrimers is an extremely fruitful and convenient strategy for developing novel functional materials for biomedical applications and ways to simplify the synthesis towards achieving would be beneficial. For the application of dendrimers in drug delivery and biomedical area there is a need to develop these scaffolds with biocompatible (or generally recognized as safe materials by US FDA) materials such that their metabolites are non-toxic. Since dendrimers offer multivalency, one of the advantages is to use the functional handles to append diverse functional groups such as different drug molecules and imaging agents. However, these functional groups bear different reactive groups and to append these on dendrimers there is a need to undergo several synthetic steps for attachment of specific linkers or spacer molecule. Hence there is a need to have a dendrimer with biocompatible orthogonal groups that facilitate chemoselective attachment of these functional groups in minimal synthetic steps.

SUMMARY OF THE INVENTION

According to the present invention there is provided a biocompatible nanosized hydrogel particles suitable for injectable delivery of therapeutic agents for treatment of diseases or disease states and also for bioimaging purposes. These nanoparticles, including crosslinked hydrogels of the modified asymmetric PAMAM dendrimers and other polymers, are biodegradable and release the therapeutic agent over an extended period of time. The release of the therapeutic agent occurs by dual mechanism, the first mechanism of release involves the degradation of the linking bond to release free therapeutic agent while the second mechanism involves the diffusion of free therapeutic agent from the gel network thus providing a sustained release pattern. The biodistribution of the nanosized hydrogel can be optimized based on the modulation of the size of the particle. The nanosized hydrogels disclosed in the present invention are useful for selectively treating the neuroinflammation, inflammation, and targeted delivery of drugs intra-ocularly by injecting the particles into the eye and confining their residence into the organ of interest such as vitreous chamber.

These and other objects, advantages, and features of the invention will be more fully understood and appreciated by reference to the description of the current embodiment and the drawings.

BRIEF DESCRIPTION OF THE DRAWINGS

Other advantages of the present invention will be readily appreciated as the same becomes better understood by reference to the following detailed description when considered in connection with the accompanying drawings wherein:

FIG. 4 shows the MALDI TOF/MS spectra for G4-PAMAM-O-Asp(COOH)—NHBoc (Compound 16.

FIG. 5 shows the $^1$H NMR spectra for G4-PAMAM-O-Asp(COOH)—NHBoc (Compound 16.

FIG. 14A shows hydrogels without formulation additives (absence of glycerin, PVP and PEG600), The 8-arm PEG-SH (e) shows an endotherm at 51.7° C., which is lowered on crosslinking with G4-NH-PDP as seen in curves (b), (c) and (d) for 3, 6 and 10% hydrogels respectively. FIG. 14B shows hydrogels with formulation additives (glycerin, PVP and PEG 600). In addition to the endotherms corresponding to 8armPEG-SH (37.9 to 38.9° C.) in hydrogels, an endotherm for PEG 600 is seen between 15.6 to 14.3° C.

FIG. 15A shows the intact gel after 72 hours of treatment with GSH solution at pH 4.

(FIG. 18A) day 3: hydrogel seen on the fetal membrane of the pup positioned close to the cervix, the green arrows mark the presence of fetal membrane on the pup, the black arrows show the presence of gel outside of the fetal membrane (FIG. 18B) the pup covered in fetal membrane with hydrogel on top of the fetal membrane (FIG. 18C) the pup after removal of the fetal membrane showing no signs of hydrogel on the fur or inside the fetal membrane.

FIG. 19A shows UC=uterus control, FIG. 19B shows U24 and FIG. 19C shows 72 hours=hydrogel treated uterus 24 and 74 hours, FIG. 19D shows UCxC=control upper cervix, FIG. 19E shows UCx24 and FIG. 19F shows 72 hours=hydrogel treated upper cervix 24 and 74 hours, FIG. 19G shows Cx-C=cervix control, FIG. 19H shows Cx24 and FIG. 19I shows 72 hours=hydrogel treated cervix 24 and 74 hours (40× magnification)

FIGS. 20A-F show the confocal images of the cervical region of pregnant guinea pigs treated with hydrogels for 24 (FIGS. 20A and 20D) and 72 hours (FIGS. 20B, 20C, 20E and 20F). The in-situ forming hydrogel comprising FITC-G4-NH-PDP crosslinked with 8-arm PEG-SH was applied to the cervicovaginal region. The hydrogel (green color) is seen on the surface of the mucosal layer (red color). The confocal images after 24 and 72 hours confirm the presence of the gel on the tissue surface. The nuclei for all cells are stained blue with DAPI. There is no sign of the degraded gel into the subepithelial or submucosal layers. EP=epithelial layer, SE=subepithelial layer, ML=mucified epithelial layer (FIGS. 20C (cervix) and 20F (upper cervix)).

DETAILED DESCRIPTION OF THE PREFERRED EMBODIMENTS

Figure 1:
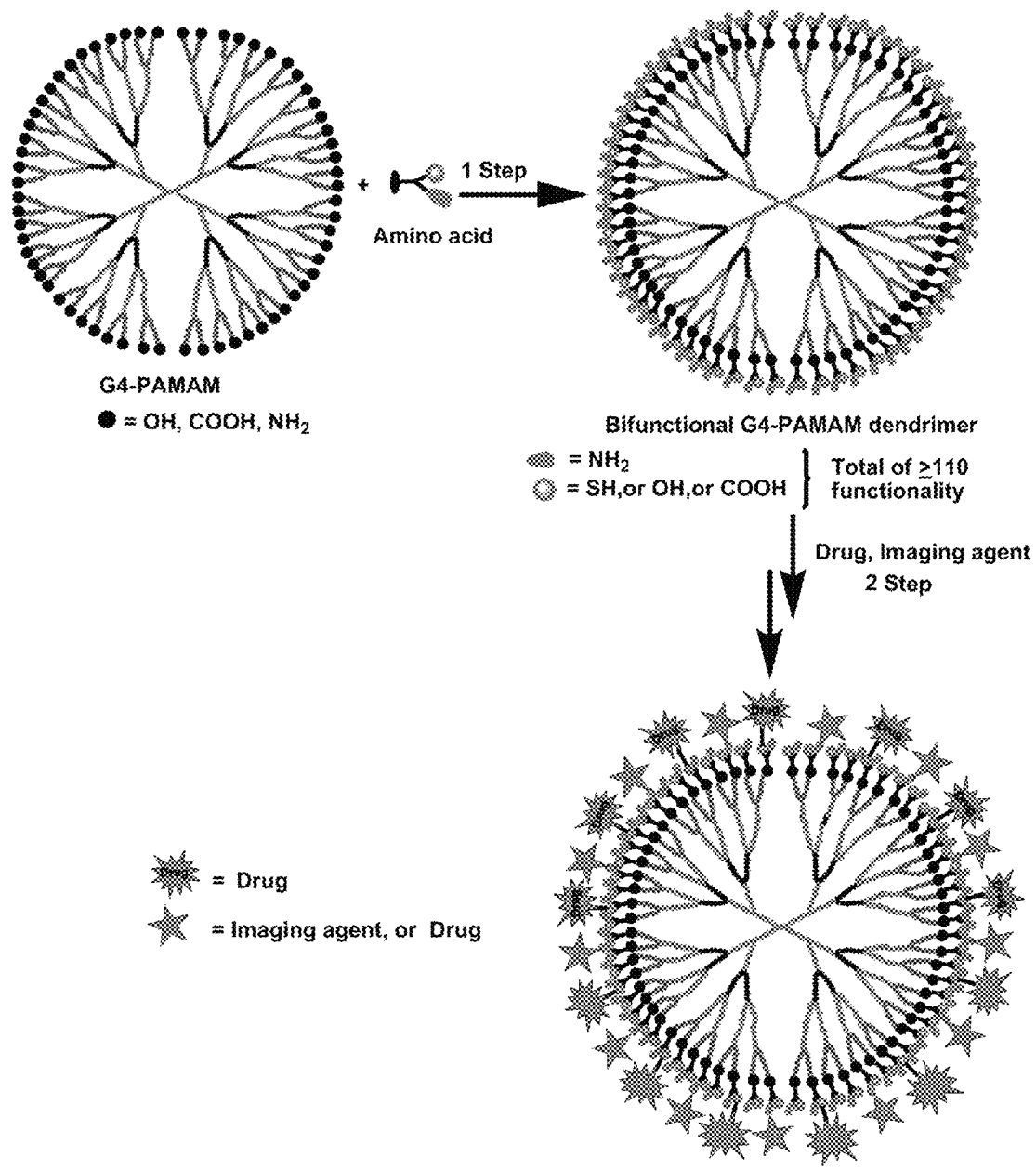
FIG. 1 is a schematic representation of bifunctional dendrimer and its post-functionalization in immediate succession.

Generally, the present invention provides biocompatible, injectable, nanosized hydrogels. The size of the nanohydrogels can be controlled and optimized for the targeted delivery to the organs of interest.

Generation 4-PAMAM dendrimers bear approximately 64 symmetrical end groups, often requiring different spacers to conjugate various functional groups, increasing the synthetic steps. In the present invention, a simple one step synthesis is used to convert the symmetrical end groups of generation 4 polyamidoamine (G4-PAMAM) dendrimers into two reactive, distinct orthogonal and chemoselective groups. A near complete end capping of the dendrimers (87-91%) with amino acids results in hetero-bifunctional G4-PAMAM dendrimers bearing very high (≥110) diverse peripheral end groups (OH+NHBoc, OH+COOMe, SH+NHBoc and COOH+NHBoc). The hetero-bifunctional groups at the dendrimer periphery can be chemoselectively conjugated to multiple functional groups such as drugs (indomethacin and dexamethasone) and/or imaging agents (dexamethasone and fluorescein isothiocynate). These conjugations can be achieved in immediate succession without requiring any protection and/or deprotection steps or functional group conversions, eliminating the additional elaborate synthetic steps traditionally required to append specific linkers. Further, one of the two functional handles at the periphery can be used to develop in-situ forming hydrogels, while the other handle could be used for conjugating the drugs (e.g. dexamethasone).

More specifically, the present invention discloses a sustained drug releasing hydrogel wherein the drug is covalently attached to the gel only at one functional terminal of the PAMAM dendrimer while the other terminal of the PAMAM dendrimer is used for gel formation. This is achieved in immediate successions and these gels are formed as nanosized particles resulting from crosslinking of the PAMAM dendrimer and another polymer. These compounds have shown a significant improvement in the reduction of the synthetic steps and conjugation of multiple functionalities. Further, the compositions have shown increased efficacy and treatment of neuroinflammation and inflammation.

The hydrogel of the present invention can act as a nanodevice and can offer several advantages. Unlike the conventional hydrogels where the drug is passively entrapped in the hydrogel, the nanosized hydrogel of the present invention has the drug covalently attached to one functional terminal end group of PAMAM dendrimer while the other terminal end of the dendrimer forms the hydrogel. The drug release pattern from these hydrogels is governed by hydrolysis or breakdown of the chemical bond linking the drug to the hydrogel mediated by the enzymes; change in pH or by action of other body fluids. The nature of linking bond can be tailored to provide a sustained release in the region of interest. These hydrogels therefore provide better handle in providing sustained delivery of the therapeutic agents over the conventional hydrogels where the drug is released by diffusion. A high payload of the drug can be achieved on one of the terminal groups of the asymmetric PAMAM dendrimer while the other terminal end group forms hydrogels. The possibility of burst release with excessive drug release is overcome and a sustained drug release is achieved. Since the drug payload is high, the amount of the carrier or the polymer scaffold is lower. The injectable nanosized hydrogels disclosed in the present invention are biocompatible.

The hydrogels of the present invention can be formed of crosslinked nano beads or particles. The size of the hydrogels can be controlled and optimized for targeted delivery to the tissue of interest. For example, the hydrogels can be in the size range 5 nm to 10 μm. The presence of orthogonal chemoselective groups on the PAMAM dendrimer with asymmetrical terminations enables the attachment of drugs or imaging agents or both in immediate succession eliminating the elaborate synthetic and purification steps. The conventional hydrogels are formed by crosslinking of the polymers bearing symmetrical terminal groups. The hydrogels are based on PAMAM dendrimers wherein the dendrimer by itself has two terminal functionalities enabling formation of hydrogel exclusively involving only one functional group which conserving the other for attachment of drugs and imaging agents is not known. The gel is formed by reaction of the PAMAM dendrimer with asymmetrical end groups with other polymers. Examples of such polymers include, but are not limited to, linear, branched, hyperbranched or star shaped polymers with functionalized terminal groups. The PAMAM dendrimer with asymmetrical terminal groups consists of a Generation 2 and above PAMAM dendrimer with symmetrical end groups modified using the amino acids or their modified forms. The gel disclosed in the present invention is formed as small crosslinked particles in the size range 25 nm to 10 μm and is suitable for injectable delivery of hydrogel to any of the body orifices, tissues by intramuscular or subcutaneous route and ocular delivery for the purpose of therapeutic treatment and imaging.

In another embodiment of the present invention, the hydrogel can be formed by chemical modification of symmetric PAMAM dendrimer with amino acids. For example, the said gel can be in the form of particles in the size range 5 nm to 10 μm (wherein nanoparticles can be in the size range of 5 nm to 900 nm, preferably from 50 nm to 500 nm.), and the other polymer involved in crosslinking is a linear, branched or star shape polymer or a dendrimer.

Specifically, the nanoparticles of the present invention is obtained by crosslinking with other polymer is characterized by presence of disulfide crosslinks, thioester and amide linkages. The PAMAM dendrimer can also be a poly(amidoamine) dendrimer of generation 2 and above wherein the surface has an asymmetrical end or peripheral groups obtained by modification of the symmetrical end groups by reaction with amino acids. Alternatively, the PAMAM dendrimer can include a generation 4 poly(amidoamine) dendrimer surfacized or modified with amino acids to yield all symmetrical terminal end groups into asymmetrical end or peripheral groups.

The PAMAM dendrimer of the present invention can also include amine, carboxylic acid, or hydroxyl terminations prior to modification with amino acids. Wherein, the amino acids can include, but are not limited to, serine, aspartic acid, cysteine, glutamic acid, threonine, tyrosine or their protected forms such as tert-butylcarbonyl-serine-hydroxysuccinimide (Boc-Ser-NHS), tert-butylcarbonyl-aspartic acid (Boc-Asp-OH), tert-butylcarbonyl-glutamic acid (Boc-Glu-OH), fluorenylmethoxycarbonyl-serine (Fmoc-Ser), fluorenylmethoxycarbonyl-aspartic acid (Fmoc-Asp-OH), fluorenylmethoxycarbonyl-glutamic acid (Fmoc-Glu-OH), tert-butylcarbonyl-cysteine-hydroxysuccinimide (Boc-Cys-NHS), serine-methylester (H-ser-OMe), cysteine-methylester (H-Cys-OMe), aspartic acid-methylester (H-Asp-OMe), glutamic acid-methyl ester (H-Glu-OMe), tert-butylcarbonyl-threonine-hydroxysuccinimide (Boc-Thr-NHS), threonine-methylester (H-Thr-OMe), fluorenylmethoxycarbonyl-threonine (Fmoc-Thr), tert-butylcarbonyl-tyrosine-hydroxysuccinimide (Boc-Tyr-NHS), tert-butylcarbonyl-tyrosine (Boc-Tyr-OH), Tyrosine-methylester (H-Tyr-OMe), cysteine-dithiopyridine (Cys-S-STP), tert-butylcarbonyl-cysteine-dithiopyridine (Boc-Cys-S-STP). S-STP refers to dithiopyridine.

The PAMAM dendrimer of the present invention can be formed wherein one of the end groups is involved in formation of hydrogel while the other end group is available for conjugation of drug or an imaging agent. Examples of such drugs and imaging agents can include, but are not limited to, G4-PAMAM-NH—CO-Ser(OH)—NHBoc, G4-PAMAM-NH—CO-Ser(OH)—NH$_2$, G4-PAMAM-NH—CO-Cys(SH)—NHBoc, G4-PAMAM-NH—CO-Cys(SH)—NH$_2$, G3.5-PAMAM-CO—NH-Ser(OH)—COOMe, G3.5-PAMAM-CO—NH-Ser(OH)—COOH, G4-PAMAM-O—CO-Cys(SH)—NHBoc, G4-PAMAM-O—CO-Cys(SH)—NH$_2$, G4-PAMAM-O—CO-Asp(COOH)—NHBoc, G4-PAMAM-O—CO-Asp(COOH)—NH$_2$, G4-PAMAM-O—CO-Cys(S-TP)-NHBoc and G4-PAMAM-O—CO-Cys(S-TP)—NH$_2$. "S-TP" refers to thiopyridine. The secondary amine group (—NH—) or the carbonyl group (—CO—) derived from —NH$_2$, or —COOH, respectively, of the amino acids as a result of conjugation to the terminal groups of the PAMAM dendrimers are omitted from the chemical denotations in some instances. In other instances, the terminal groups on the PAMAM dendrimers linked to the amino acids are also omitted. For example, G4-PAMAM-O—CO-Asp(COOH)—NH$_2$, G4-PAMAM-O-Asp(COOH)—NH$_2$, and G4-PAMAM-Asp(COOH)—NH$_2$ are used interchangeably to describe G4-PAMAM dendrimers conjugated to aspartic acid via terminal hydroxyl groups on the dendrimer as depicted in Scheme 5 (compound 17).

The PAMAM dendrimers of the present invention can also be reacted with the amino acid such that it yields two distinct orthogonal chemoselective asymmetrical end groups on the surface suitable for post-functionalization in immediate succession such as conjugation for drugs and/or imaging agents and hydrogel formation.

The hydrogel of the present invention is formed by the direct crosslinking of the asymmetric PAMAM dendrimer with other polymer involving a chemical reaction, or by physical crosslinking and photopolymerization reactions. The formed hydrogel is degradable in nature wherein the crosslinks are hydrolyzed over a period of time in response to the change in pH of environment, presence of enzymes and body fluids. Additionally, the rate of degradation can be modulated by the nature of the crosslinks.

The drug contained within the hydrogel can be released over an extended period of time in a dual manner, wherein the first mechanism of release involves the degradation of the linking bond to release free drug while the second mechanism involves the diffusion of free drug from the gel network. Examples of such drugs include, but are not limited to, macrolide antibiotics, such as, erythromycin, azithromycin, rapamycin and clarithromycin; tetracyclines, such as, minocycline, doxycycline, fluroquinolones, such as, ciprofloxacin, enrofloxacin, ofloxacin, gatifloxacin, levofloxacin and norfloxacin; cephalosporins, such as, cefuroxime, cefaclor, cephalexin, cephadroxil and cepfodoxime proxetil; nonsteoroidal, anti-inflammatory and analgesic drugs, such as, ibuprofen, aspirin, acetaminophen and diclofenac sodium and corticosteroids such as fluocinolone acetonide and methylprednisolone, antibodies such as ranibizumab, vitamins, peptides, growth factors, siRNAs, microRNAs, resolvins, neurostimulants and neuroprotectants or a pharmaceutically acceptable salts thereof.

The imaging agent for use with the present invention can include, but is not limited to, fluorescent dyes, for example, fluorescein isothiocynate, Carboxyfluorescein, fluorescein hydroxysuccinimide, tertramethyl rhodamine isothiocynate, alexa fluor dyes bearing hydroxylamine, hydrazide, cadaverine, aldehyde, ketone, carboxylic, amine and thiol reactive groups, cyanine dye, Texas red radiolabelled dyes selected from the group of $^{14}$C, $^{3}$H, $^{64}$Cu, magnetic resonance imaging agents $^{125}$I, $^{99}$Tc, $^{111}$In, gadolinium, and gadolinium tetra-azacyclododecanetetraacetic acid (Gd-DOTA).

The crosslinking polymer for use in the present invention is a functionalized polyethylene glycol (PEG) polymer in the size range of 5 kDa to 80 kDa, preferably 20-40 kDa. The functionalized PEG polymer can be either a linear or a branched PEG having a molecular weight of 20-40 kDa and bearing symmetrical terminations such as, amine, thiol, maleimide, carbonates, carbamates, N-hydroxy-succinimide, dithiopyridine, methacrylate, methoxy, hydrazine, azide, acid, alcohol, aldehyde, allyl, vinyl, epoxy, isothiocynate and isocyanate.

The hydrogel occurs due to the interaction between the asymmetric PAMAM dendrimer and the other polymer directly and alternately by use of suitable spacer which crosslinks the dendrimer and other polymer wherein the spacer is selected from the group consisting of bifunctional molecules in the size range 1-10 kDa wherein the bifunctional molecules are maleimide-poly(ethyleneglycol)-maleimide, Succinimidyl-carboxyl-methyl ester-poly(ethyleneglycol)-succinimidyl-carboxyl-methyl ester, acrylate-poly(ethyleneglycol)-acrylate, ortho-pyridyldisulfide-poly (ethyleneglycol)-ortho-pyridyldisulfide, thiol-poly(ethyleneglycol)-thiol, nitrophenyl carbonate-poly(ethyleneglycol)-nitrophenyl carbonate, isocyanate-poly(ethyleneglycol)-isocyanate, 1,6-hexane-bis-vinylsulfone and any other polymer which bears these functional terminations.

Examples of the nanoparticles include, but are not limited to, G4-PAMAM-NH—CO-Cys(S-TP) cross linked with 8-arm-poly(ethyleneglycol) with thiol terminations, G4-PAMAM-NH— pyridyldithio-propionate cross linked 8-arm-poly(ethyleneglycol) with thiol terminations, FITC-G4-PAMAM-NH-pyridyldithio-propionate crosslinked with 8-arm-poly(ethyleneglycol) with thiol terminations, G4-PAMAM-O-Cys(SH)—NH—FITC and 8-arm-poly(ethyleneglycol) with thiol terminations, FITC-G4-NH-Maleimide cross linked with 8-arm-poly(ethyleneglycol) with thiol terminations, G4-PAMAM-O—CO-Cys(S-Tp)-$NH_2$ cross linked with methoxy-poly(ethyleneglycol) with thiol termination (Meo-PEG-SH), G4-PAMAM-O—CO-Cys(SH)—$NH_2$ cross linked with pyridyldithio-propionate-poly(ethyleneglycol)-pyridyldithio-propionate. A high payload of the drug can be achieved on one of the terminal groups of the asymmetric PAMAM dendrimer while the other terminal end group forms hydrogels. This type of hydrogel where the drug is covalently bond to the hydrogel offers a sustained release of the drug over the extended period of times as compared the conventional hydrogels preparations where the drug is physically entrapped and diffuses out of the hydrogel.

The drug release pattern from these hydrogels is governed by hydrolysis or breakdown of the chemical bond linking the drug to the hydrogel mediated by the enzymes, change in pH or by action of other body fluids. The nature of linking bond can be tailored to provide a sustained release in the region of interest. These hydrogels therefore provide better sustained delivery of the therapeutic agents over the conventional hydrogels where the drug is released by diffusion.

A library of dendrimers having hetero-bifunctional groups at periphery, amenable for further modifications is disclosed (Table 1). The present invention provides a robust, simple synthetic approach to attain near complete surface modification with amino acids to yield hetero-bifunctional end terminations on a biocompatible dendrimer scaffold (FIG. 1). Past reports on synthesis of bifunctional dendrimers involve multiple steps. A simple one pot synthesis to achieve orthogonal and chemoselective end groups by complete end capping of the G4 PAMAM dendrimers with amino acids is shown in Schemes 1-5, 7. The present invention shows that ≥110 hetero-bifunctional end groups can be achieved on a generation four (G4) dendrimer (FIG. 1) without going to next generation (G5) dendrimers. This is a significant since it is well known that dendrimers exhibit generation dependant cytotoxicity. PEGylation of G5 and G6 PAMAM-$NH_2$ dendrimers significantly reduced its hemolytic activity but paradoxically compromised its transfection ability. The choice of the materials to design these hetero-bifunctional dendrimers was based on developing biocompatible dendrimer scaffolds for drug delivery applications, and also retaining the reactivity of terminal groups for drug conjugation.

One of the advantages of the present system, having multiple diverse functional handles on periphery groups is the ease of conjugating different drugs, along with imaging agents and/or targeting ligands without the need of additional synthetic steps to attach specific spacer or linker molecules. The feasibility of the concept, and the chemoselective and orthogonal nature of these new hetero-bifunctional dendrimers was demonstrated by conjugation of 1) two drugs viz. dexamethasone and indomethacin and 2) indomethacin and imaging agent (FITC) on the aspartic acid surface-modified PAMAM dendrimer. Thus two different moieties were added in immediate succession without any deprotection steps or functional group conversions owing to the orthogonal peripheral groups. Additionally, of the two diverse functional handles on the hetero-bifunctional dendrimers, one of the functional handles was selectively used for in-situ hydrogel formation, while the second functional handle was used for conjugating drug and or imaging agent.

Dendrimers have emerged as multifunctional carriers for targeted drug delivery and diagnostic agents. Additionally, dendrimers have become integral in improving the functional versatility at the surface for carrying multiple conjugation reactions is becoming vital. The compositions disclosed in present invention performs several functions like targeting, localization at diseased site, releasing the drug, imaging purpose and therefore the composition in itself acts as a nanodevice.

Hydrogels can be used for many different applications such as molecularly engineered scaffolds for controlled drug release, cellular delivery, tissue engineering and as wound dressings due to the highly hydrated and three dimensional properties which are similar to the native extracellular matrix (ECM). They have attracted a great deal of attention as a matrix for the controlled delivery of biologically active substances. The suitability of hydrogels for the pharmaceutical applications is mainly determined by their mechanical properties, drug loading and controlled drug release capability. In-situ forming gels have been investigated for a varied applications such as oral, nasal, ocular, injectable, vaginal and rectal. Thermosensitive gels are commonly investigated for the vaginal delivery of therapeutic agents as they gel in response to the body temperature. Thermosensitive vaginal gels for delivery of cotrimazole were formulated using Pluronic F127. Polycarbophil hydrogels were investigated for intravaginal delivery of granulocyte-macrophage colony-stimulating factor (GM-CSF) for treatment of human papillomavirus (HPV)-associated genital (pre) neoplastic lesions.

The intravaginal route of drug administration can be used as an effective means for local delivery of antibacterials, antifungals, antiprotozoals and antivirals agents. The use of topical microbicides is common in pregnant women to treat yeast and bacterial infections. Bacterial vaginosis (BV) is found in 15-20% of pregnant women and it is an ascending genital tract infection of chorioamnion and amniotic fluid. Intrauterine infection during pregnancy is often responsible for disease causing spontaneous preterm birth and the infection which is associated with the microorganisms ascending from vagina and cervix is known to affect the fetal membranes and the cervical mucosa and endometrium. Local drug delivery to cervical tissues is preferred. To treat BV in pregnant women antibiotics are administered intra-vaginally and the intravaginal route is preferred to attain high local drug concentration in the vagina, which cannot be achieved by oral administrations. One major problem associated with intravaginal and intrauterine drug delivery is limited contact time of administered dosage form with the mucosa due to the physiological conditions imposed by the protective mechanisms of the cervix and vagina. This reduces the therapeutic efficacy and necessitates frequent dosing. Hydrogels are better tolerated than other conventional dosage forms and thus provide a better treatment option.

Hydrogels are preferred drug delivery vehicles in pharmaceutical industry especially for the ocular delivery of drugs. Dendrimer based imaging agents are in the process of gaining approvals for human use. Dendrimer based intravaginal gels can also be used as topical microbicides. Polylysine dendrimer SPL7013 exhibited antimicrobial activity against herpes simplex virus and its formulation development into a prototype acidified carbopol gel for intravaginal delivery was evaluated in animal models. Human clinical trials (Phase I and II) were conducted to determine the retention, duration of activity, safety and tolerability of a gel containing SPL7013 applied intravaginally to young non-pregnant women and the gel was found to be safe and well tolerated. Apart from SPL7013, the amine terminated PAMAM dendrimers are found to exhibit antibacterial activity towards gram-ve bacteria. PAMAM dendrimer with hydroxyl terminations was found to effectively inhibit intra-uterine *Escherichia coli* (*E. Coli*) infections in guinea pigs. These dendrimers have also been used as carriers for the antimicrobial agents (e.g. triazine antibiotics). Quinolone drugs encapsulated in PAMAM dendrimers are highly active when used as topical microbicidal agents. The PAMAM dendrimer based silver complexes and nanocomposites have been shown to have increased antibacterial activity towards the *S. aureus, P. aeruginosa* and *E. coli*. Further, dendrimers are also extensively evaluated in several gel formulations. Many polymers can be used as topical microbicides or as a component of the topical microbicide formulations to be applied on the vagina or rectal mucosa.

The hydrogels of the present invention can be used to treat several macular degeneration related diseased conditions. The hydrogels can also be used in treating neuro-inflammation and inflammation in the eye by intraocular delivery. The hydrogels also have site-specific localization of the dendrimers based on their size and can therefore effectively deliver drugs to the diseased site. Further, these nanodevices can be used for the diagnostic and imaging purposes.

The above discussion provides a factual basis for the methods and uses described herein. The methods used with and the utility of the present invention can be shown by the following non-limiting examples.

EXAMPLES

Example 1

Synthesis of Asymmetrical hetero-bifunctional G4 PAMAM Dendrimers

Synthesis of
G4-PAMAM-NH—CO-Ser(OH)-NHBoc (3)

To a stirred solution of G4-PAMAM-NH$_2$ (1) (500 mg, 0.035 mol) and Boc-Ser-NHS (Compound 2) (1360 mg, 4.50 mol) in DMSO/DMF (4:1, 25 mL) followed by addition of DIEA (775 µl, 4.50 mol). The reaction was allowed to continue for 24 hours at room temperature (r.t.). The crude product was purified by dialysis against DMSO (3 times for 36 hours), and after dialysis the solvent was removed under lyophilization to get pure compound in 75% yield (646 mg, 0.026 mol). The chemical structure of G4-PAMAM-NH—CO-Ser(OH)—NH$_2$ (3) was confirmed by $^1$H-NMR and MALDI-MS spectra. $^1$H-NMR (DMSO-d$_6$, 400 MHz), 1.38 (s, 9H, Boc), 2.10-2.22 (br.s, OH), 3.22-3.38 (m, 1H, CH$_2$), 4.50-4.58 (m, 1H, CH$_2$) 4.80-4.90 (m, 1H, CH) 6.50-6.60 (m, 1H, NH amide), 7.78-7.97 (br. d, NH amide interior dendrimer amide), MALDI-MS: 24501 Da Synthesis of
G4-PAMAM-NH—CO-Ser(OH)—NH$_2$ (4)

Boc (tert-Butoxycarbonyl) deprotection was carried out by adding G4-PAMAM-NH—CO-Ser (OH)-NHBoc (Compound 3) (500 mg, 0.020 mol) in TFA/DCM (50:50% v/v, 10 mL) for 15 minutes. Post de-protection, the solution was neutralized pH=7.0 using 1N NaOH solution. The compound was dialyzed overnight using water as solvent and lyophilized to yield G4-PAMAM-NH-COSer(OH)—NH$_2$ with NH$_2$ and OH terminations. The compound (4) was obtained by lyophilization in 89% yield (339 mg, 0.018 mol). $^1$H-NMR and MALDI-MS spectra. $^1$H-NMR (DMSO-d$_6$, 400 MHz), δ, 1.0-1.19 (m, 2H, NH$_2$), 1.80-1.98 (br. s, 2H, OH), 4.21-4.26 (s, 1H), 8.0-8.15 (br. d from amide NH), 8.30-8.6 (br. d, amide NH), MALDI-MS: 18747 Da.

Synthesis of G4-PAMAM-NH—CO-Cys
(SH)-NHBoc (6)

To a stirred solution of G4-PAMAM-NH$_2$ (1) (500 mg, 0.035 mol) and Boc-Cys-NHS (5) (1432 mg, 4.50 mol) in DMSO/DMF (4:1, 25 mL), DIEA (775 µl, 4.50 mol). The reaction was continued for 24 hours at r.t. The reaction mixture was purified on dialysis with DMSO (36 hours) to remove by-products and the excess of reactants, and after dialysis the solvent was removed under lyophilization to get pure compound (6) in 77% yield (671 mg, 0.027 mol). $^1$H-NMR (DMSO-d$_6$, 400 MHz), δ 1.35 (s, 9H, Boc) 2.10-2.20 (br.s, SH), 3.25-3.40 (m, 2H, CH$_2$), 3.95-4.20 (m, 1H, CH), 7.80-8.20 (br. d, 1H, dendrimer interior amide), 8.22-8.45 (br.s, 1H, amide) MALDI-MS: 25807 Da Synthesis of G4-PAMAM-NH—CO-Cys
(SH)—NH$_2$ (7)

Boc (tert-Butoxycarbonyl) deprotection was carried out by adding G4-PAMAM-NH—CO-Cys (SH)-NHBoc (6) (500 mg, 0.019 mol) in TFA/DCM (50:50% v/v, 10 mL) for 15 minutes. Post de-protection, the solution was neutralized pH=7.0 using 1N NaOH solution. The compound was dialyzed overnight using water as solvent and lyophilized to yield G4-PAMAM-NH—CO-Cys (SH)—NH$_2$ with NH$_2$ and SH terminations. The compound (7) was obtained by lyophilization in 88% yield (326 mg, 0.017 mol). $^1$H-NMR (DMSO-d$_6$, 400 MHz), δ 1.0-1.23 (m, NH$_2$), 1.78-2.00 (br.s, 2H, OH) 3.60-3.75 (m, 1H —CH— for Cysteine) 7.97-8.10 (br. s, amide NH from Cysteine), 9.80-10.10 (br. m, amide NH from dendrimer interior amide). MALDI-MS: 19365 Da Synthesis of G3.5-PAMAM-CO—NH-Ser-OMe
(10)

To a stirred solution of G3.5-PAMAM-COOH (6) (100 mg, 0.0086 mol) and H-Ser-OMe (9) (132 mg, 1.11 mol) in water (4 ml) was added DMSO/DMF (4:1, 12 mL), DMAP (136 mg, 1.11 mol) and the reaction was stirred for 5 minutes followed by addition of EDC (213 mg, 1.11 mol) at once. The reaction was continued for 24 hours at r.t. The reaction mixture was purified by dialysis with DMSO (36 hours) to remove by-products and the excess of reactants, and after dialysis the solvent was removed under lyophilization to get pure compound (10) in 78% yield (116 mg, 0.0067 mol). $^1$H-NMR (DMSO-d$_6$, 400 MHz), δ 3.60 (S, 3H, COOMe), 6.62-3.75 (m, 2H, CH$_2$), 4.30-4.58 (m, 1H, CH), 7.77-7.95 (br. d, NH), 8.37-8.41 (s, 1H, amide), MALDI-MS: 17209 Da

Synthesis of G3.5-PAMAM-CO—NH-Ser-OH (11)

Hydrolysis of methyl ester was carried out by adding G3.5-PAMAM-CO-Ser (OH)-OMe (10) (100 mg, 0.005 mol) with LiOH (5 mg, 2.26 mol) in THF/H$_2$O (9:1 10 mL) for 5 hours after completion of reaction, the compound was dialyzed overnight using water as solvent and lyophilized to yield G3.5-PAMAM-CO—NH-Ser-OH (11) with COOH and OH terminations. The compound (11) was obtained by lyophilization in 88% yield (81 mg, 0.0.005 mol) $^1$H-NMR (DMSO-d$_6$, 400 MHz, δ in ppm) 1.40-1.50 (m, 2H, NH$_2$), 1.92-2.05 (br. s, 1H, OH), 3.33-3.42 (br.s, 1H, —CH—, Serine), 8.15-8.40 (br. d, amide NH), 8.75-8.90 (br. s, amide NH), $^{13}$C-NMR (DMSO-d$_6$, 400 MHz), 14.97, 26.45, 33.94, 36.80, 37.56, 45.12, 50.29, 52.87, 56.02, 155.60, 170.10, 172.91. FTIR spectrum shows absorptions at 1720, 2950, 3550 cm$^{-1}$ assigned for C=O, C—H, O—H stretch of serine, MALDI-MS: 15959 Da.

Synthesis of G4-PAMAM-O—CO-Cys(SH)-NHBoc (13)

To a stirred solution of Boc-Cys-OH (5) (1487 mg, 6.72 mol) and G4-PAMAM-OH (12) (500 mg, 0.035 mol) in DMSO/DMF (3:1) was added DMAP (366 mg, 3.0 mol), EDC (899 mg, 4.51 mol)) and the reaction was allowed to proceed overnight for 18 hours. The product so obtained was purified by dialysis using spectrapor dialysis membranes in DMSO as a solvent, to remove the by-products and the excess of reactants. After dialysis the solvent was removed under lyophilization to get pure compound (13) in 80% yield (732 mg, 0.144 mol). $^1$H-NMR (DMSO-d$_6$, 400 MHz), δ, 1.25 (br. s, 1H from Cysteine SH), 1.35 (br. s, 9H, tert-Butoxycarbonyl from Cysteine), 2.10-2.25 (br.s, 1H, —SH from Cysteine), 4.55-4.75 (br. d —CH— from Cysteine), 7.80-8.10 (br. d, NH from dendrimer interior amide), 8.20-8.30 (br. s, NH from Cysteine amide), $^{13}$C-NMR (DMSO-d$_6$, 100 MHz), 28.59, 28.78, 33.86, 37.51, 38.02, 42.12, 50.23, 52.80, 54.19, 56.94, 60.55, 66.50, 79.76, 108.10, 143.20, 155.90, 156.69, 169.61, 172.01, 172.32, 172.56, MALDI-TOF/MS: 25068 Da.

Synthesis of G4-PAMAM-O—CO-Cys(SH)—NH$_2$ (14)

Boc (tert-Butoxycarbonyl) deprotection was carried out by adding G4-PAMAM-O—CO-Cys (SH)-NHBoc (13) (500 mg, 0.019 mol) in TFA/DCM (50:50% v/v, 10 mL) for 5 minutes. Post de-protection, the solution was neutralized pH=7.0 using 1N NaOH solution. The compound was dialyzed overnight using water as solvent and lyophilized to yield G4-O-Cys(SH)—NH$_2$ with NH$_2$ and SH terminations. The compound (14) was obtained by lyophilization in 87% yield (334 mg, 0.017 mol). $^1$H-NMR (DMSO-d$_6$, 400 MHz), δ, 2.12-2.24 (m, 2H, —CH$_2$—, Cysteine), 4.70-4.78 (m, 1H, —CH—, Cysteine), 7.76-7.89 (br. d, NH from dendrimer interior amide), 7.91 (br. s, NH from Cysteine amide). MALDI-MS: 19262 Da.

Synthesis of G4-PAMAM-O—CO-Asp(COOH)-NHBoc (16)

To a stirred solution of BOC-Asp-OH (15) (2500 mg, 10.7 mol) was added G4-PAMAM-OH (12) (1000 mg, 0.070 mol) in DMSO/DMF (3:1) and DMAP (729.9 mg, 5.975 mol), EDC (1783 mg, 8.95 mol) and PyBOP (1993 mg, 3.83 mol) and the reaction was allowed to proceed overnight for 18 hours. The product was purified by dialysis using spectrapor dialysis membranes in DMSO as solvent to remove by-products and the excess of reactants, and after dialysis the solvent was removed under lyophilization to get pure compound (16) in 80% yield (1503 mg, 0.058 mol). $^1$H-NMR (DMSO-d$_6$, 400 MHz), δ, 1.30 (s, 9H), 4.28-4.38 (br. s, 1H), 7.75-7.90 (br.s, amide NH), 7.92-8.10 (br. d, amide NH). $^{13}$C-NMR (DMSO-d$_6$, 100 MHz), 28.77, 33.46, 37.39, 38.13, 50.04, 50.76, 52.79, 63.76, 79.08, 79.12, 95.10, 155.91, 170.66, 171.82, 172.23. MALDI-MS: 25740 Da.

Synthesis of G4-PAMAM-O—CO-Asp-(COOH)—NH$_2$ (17)

Boc (tert-Butoxycarbonyl) deprotection was carried out by adding G4-PAMAM-O—CO-Asp-Boc (16) (1000 mg) in TFA/DCM (50:50% v/v) for 5 minutes. Post de-protection, the solution was neutralized using 1N NaOH solution. The compound was dialyzed overnight using water as solvent and lyophilized to yield G4-O-Asp-OH with COOH and NH$_2$ terminations. The compound (17) was obtained by lyophilization in 90% yield (627 mg, 0.033 mol). $^1$H-NMR (DMSO-d$_6$, 400 MHz, δ in ppm) 4.22-4.35 (br.s, 1H), 7.96-8.10 (br. s, amide NH) 8.10-30 (br. d, amide, NH). MALDI-MS: 18990 Da.

Synthesis of G4-PAMAM-O—CO-Asp-(CO-Dex)-NH$_2$ (20)

To a stirred solution of G4-PAMAM-O—CO-Asp-(COOH)-NHBoc (16) (200 mg, 0.0105 mol) in a DMSO/DMF(3:1, 20 mL) was added EDC (506 mg, 2.64 mol), DMAP (160 mg, 1.31 mol) and dexamethasone (15) (520 mg, 1.32 mol) and the reaction was allowed to proceed at room temperature for 12 hours. After completion of the reaction, crude product was purified by dialysis using spectrapor dialysis membranes in DMSO (3 times for 36 hours) to remove by-products and the excess of reactants, and after dialysis the solvent was removed under lyophilization to get (20) pure compound in 82% yield (190 mg, 0.0086 mmol). Boc (tert-Butoxycarbonyl) deprotection was carried out by adding G4-PAMAM-O—CO-Asp(CO-Dex)-NHBoc (16) (1000 mg) in TFA/DCM (50:50% v/v) for 5 minutes. Post de-protection, the solution was neutralized using 1N NaOH solution. The compound was dialyzed overnight using water as solvent and lyophilized to yield G4-PAMAM-O—CO-Asp(CO-Dex)-NH$_2$. The compound (20) was obtained by lyophilization in 90% yield. $^1$H-NMR (DMSO-d$_6$, 400 MHz, δ in ppm), 0.75 (s, 3H), 0.82 (s, 3H), 1.0-1.10 (m, 2H), 1.280-1.36 (d, 2H), 1.38-1.41 (d, 2H), 1.45 (s, 3H) 4.45-4.50 (d, 1H), 4.92 (s, 1H), 5.24 (s, 1H), 6.01 (s, 1H), 6.23 (d, 1H), 7.30 (d, 1H). $^{13}$C-NMR (DMSO-d$_6$, 100 MHz) 15.98, 17.33, 23.55, 23.61, 27.94, 30.95, 32.68, 33.75, 34.21, 34.41, 35.55, 36.60, 42.10, 43.95, 48.12, 48.75, 50.15, 52.70, 60.56, 66.94, 71.18, 71.55, 90.84, 94.71, 101.06, 102.80, 124.80, 129.67, 153.53, 167.80, 186.0. MALDI-TOF/MS: 21981 Da.

Synthesis of G4-PAMAM-O-Asp (CO-Dex)-Ind (22)

To a stirred solution of indomethacin (21) (249 mg, 0.69 mol) in a DMSO/DMF (3:1, 20 mL) was added EDC (133 mg, 0.69 mol), DMAP (85 mg, 0.69 mol). The reaction mass was stirred for 15 minutes and G4-PAMAM-O—CO-Asp-(CO-Dex)-NH$_2$ (20) (80 mg, 0.0036 mol) was added to it.

Reaction was continued at room temperature for 15 hours. After completion of the reaction, crude product was purified by dialysis using spectrapor dialysis membranes in DMSO (36 hours) to remove by-products and the excess of reactants. After dialysis the solvent was removed under lyophilization to get G4-PAMAM-O-Asp(CO-Dex)-Ind (22) pure compound in 78% yield. Apart from dexamethasone protons listed for (20), the $^1$H-NMR of compound (22) shows appearance of protons corresponding to indomethacin. $^1$H-NMR (DMSO-$d_6$, 400 MHz), δ, 2.10-2.30 (m, 3H, $CH_3$), 3.62-3.80 (m, 5H, —$OCH_3$, —CO—$CH_2$—), 6.60-79 (m, 2H, Ar), 6.83-7.04 (m, 2H, Ar), 7.60-7.70 (m, 3H, Ar).

Synthesis of G4-PAMAM-O—CO-Asp(CO-Dex)-NH-FITC (24)

To a stirred solution of G4-PAMAM-O—CO-Asp-(CO-Dex)-$NH_2$ (20) (100 mg, 0.0038 mol) in a DMSO (10 mL) was added FITC (23) (17.6 mg, 0.045 mol). The reaction mixture was stirred at room temperature for 12 hours in dark. After completion of the reaction, crude product was purified by dialysis in dark using spectrapor dialysis membranes in DMSO (36 hours) to remove by-products and the excess of reactants, and after dialysis the solvent was removed under lyophilization to get (24) pure compound in 85% yield. Apart from dexamethasone protons listed for (23), the $^1$H-NMR of compound (24) shows appearance of protons corresponding to FITC. $^1$H-NMR (DMSO-$d_6$, 400 MHz), δ, 6.57-6.62 (d, 6H, Ar), 6.63-6.70 (s, 3H Ar)..

Synthesis of Boc-Cys (S-TP)-OH (27)

Boc-Cys(S-TP)-OH (27) was prepared from the reaction of 2,2$^1$-dithiodipyridine (7.96 g, 36 mol) and Boc-Cys-OH (4 g, 18 mol) in a mixture of methanol and water (1:1, 50 mL) and stirred for 24 hours at room temperature. Upon completion of the reaction (monitored by TLC), methanol was removed in vacuo and the residue was recrystallized with acetone and petroleum ether to give the pure product as a white solid in 70% yield (4.19 g, 0.012 mol). $^1$H-NMR (DMSO-$d_6$, 400 MHz), δ in ppm), 1.40 (s, 9H, tert-Butoxycarbonyl), 2.49 (solvent DMSO-$d_6$) 3.0-3.20 (m, 2H, —$CH_2$—), 3.33 ($H_2O$ peak in DMSO-$d_6$), 4.10-4.20 (m, 1H, —CH—), 7.25-7.30 (m, 1H, Ar), 7.35-7.40 (m, 1H, Ar), 7.78-7.88 (m, 2H, NH amide, and Ar), 8.42-8.52 (m, 1H, Ar), 12.88 (s, 1H, COOH). $^{13}$C-NMR (DMSO-$d_6$, 100 MHz), δ, 28.83, 53.42, 79.03, 94.69, 119.96, 121.95, 138.48, 150.29, 172.86.

Synthesis of G4-PAMAM-O—CO-Cvs(S-TP)-NHBoc (28)

To a stirred solution of Boc-Cys (S-TP)-OH (27) (1484 mg, 4.48 mol) and G4-PAMAM-OH (12) (500 mg, 0.036 mol) in DMSO/DMF (3:1) was added DMAP (273 mg, 2.23 mol), EDC (856 mg, 4.48 mol)) and the reaction was allowed to proceed overnight for 18 hours. The product was purified by dialysis using spectrapor dialysis membranes in DMSO as solvent to remove by-products and the excess of reactants, and after dialysis the solvent was removed under lyophilization to get pure compound (28) in 78% yield (764 mg, 0.028 mol). $^1$H-NMR (DMSO-$d_6$, 400 MHz, δ in ppm) 1.38 (s, 9H, from Cysteine tert-Butoxycarbonyl), 4.0-410 (m, 2H, —$CH_2$—, from Cysteine), 4.60-4.70 (m, 1H, —CH—, from Cysteine), 6.70-7.77 (m, 1H, Ar), 7.0-7.18 (br. d, 1H, NH amide), 7.25-7.35 (m, 1H, Ar), 7.38-7.45 (m, 1H, Ar), 7.60-7.68 (m, 1H, Ar), 8.15-8.24 (m, 1H, amide NH).

Synthesis of G4-PAMAM-O—CO-Cys(S-TP)-$NH_2$ (29)

Tert-Butoxycarbonyl deprotection was carried out by adding G4-PAMAM-O—CO-Cys(S-TP)-NHBoc (28) (500 mg, 0.018 mol) in TFA/DCM (50:50% v/v, 10 mL) for 5 minutes. Post de-protection, the solution was neutralized using 1N NaOH solution and pH of solution was monitored to obtain pH 7. The compound was dialyzed overnight using water as solvent. After dialysis the solvent was lyophilized to get compound (29) in 50% yield (238 mg, 0.0093 mol). $^1$H-NMR (DMSO-$d_6$, 400 MHz, δ in ppm) 1.82-1.97 (m, 2H, —$CH_2$—, from Cysteine), 4.62-4.70 (m, 1H —CH—, from Cysteine), 7.60-7.64 (d, 1H, Ar), 7.66-7.75 (m, 1H, Ar), 7.77-7.84 (m, 1H, Ar), 7.89-7.96 (m, 1H, NH amide), 8.19-8.25 (m, 1H, Ar), 8.40-8.52 (m, 1H, NH amide).

To achieve hetero-bifunctional G4-PAMAM dendrimer with high density of amine and hydroxyl functional groups at the periphery of (3), the symmetrical terminal 'amine' groups of G4 PAMAM dendrimer (1) were reacted with acid terminal of Boc-Ser-NHS (2).

This was a straightforward coupling reaction which converted the symmetrical peripheral amines (~64 theoretically) of G4-PAMAM-$NH_2$ (1) dendrimer into a total of ~116 hetero-bifunctional groups on the periphery bearing 58 of 'Boc-amine' and 58 of 'hydroxyl' functionalities respectively (Scheme-1), in a one step reaction. Schemes 1-2 are schematic representations for synthesis of G4-PAMAM-NH—CO-Ser(OH)-NHBoc (3), and G4-PAMAM-NH—CO-Cys(SH)-NHBoc (6) Compounds (3 and 6) show the conversion of symmetric peripheral amines of G4-PAMAM-$NH_2$ (1) into hetero bifunctional terminal groups 'OH+NHBoc' and 'SH+NHBoc' respectively. The compounds (3, 6) on deprotection of Boc group gave OH+$NH_2$' and 'SH+$NH_2$' respectively.

Figure 2A:
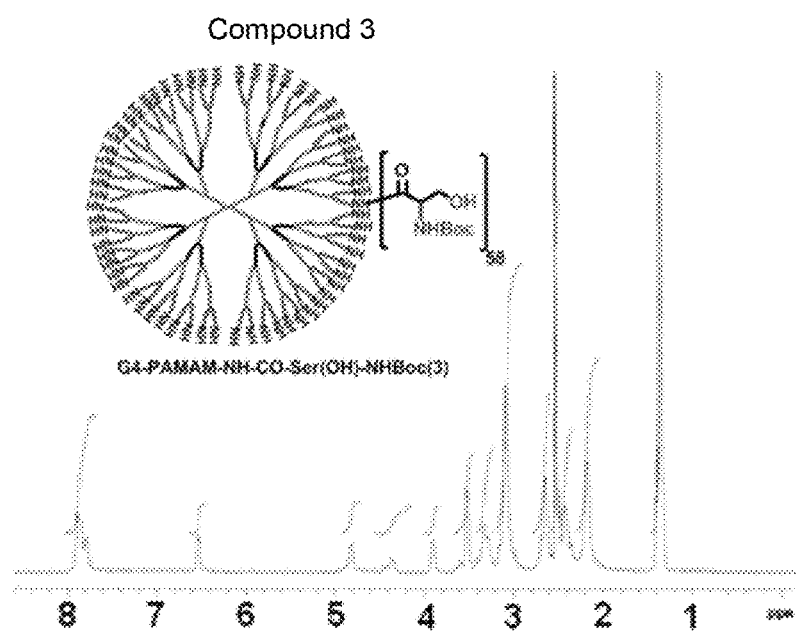
FIGS. 2A-C show $^1$H NMR (FIG. 2A), MALDI TOF/MS spectrum (FIG. 2B) and HPLC chromatogram (FIG. 2C) for G4-PAMAM-NH—CO-Ser(OH)—NHBoc (Compound 3)
Figure 2B:
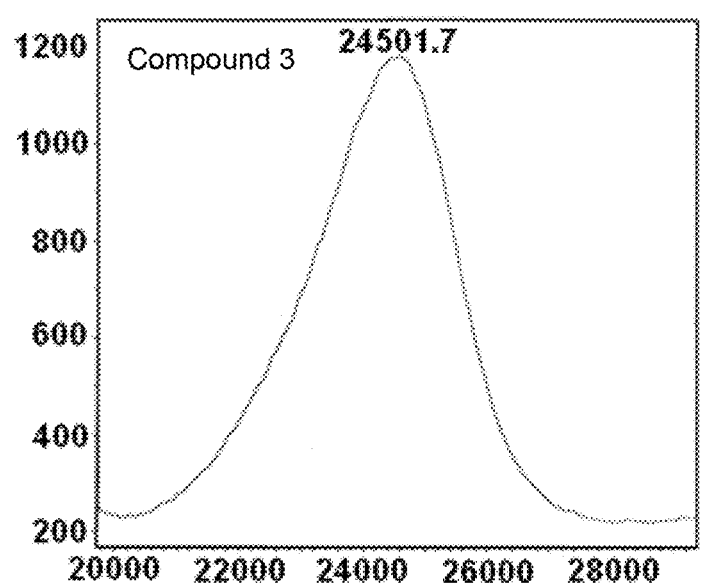
Figure 2C:
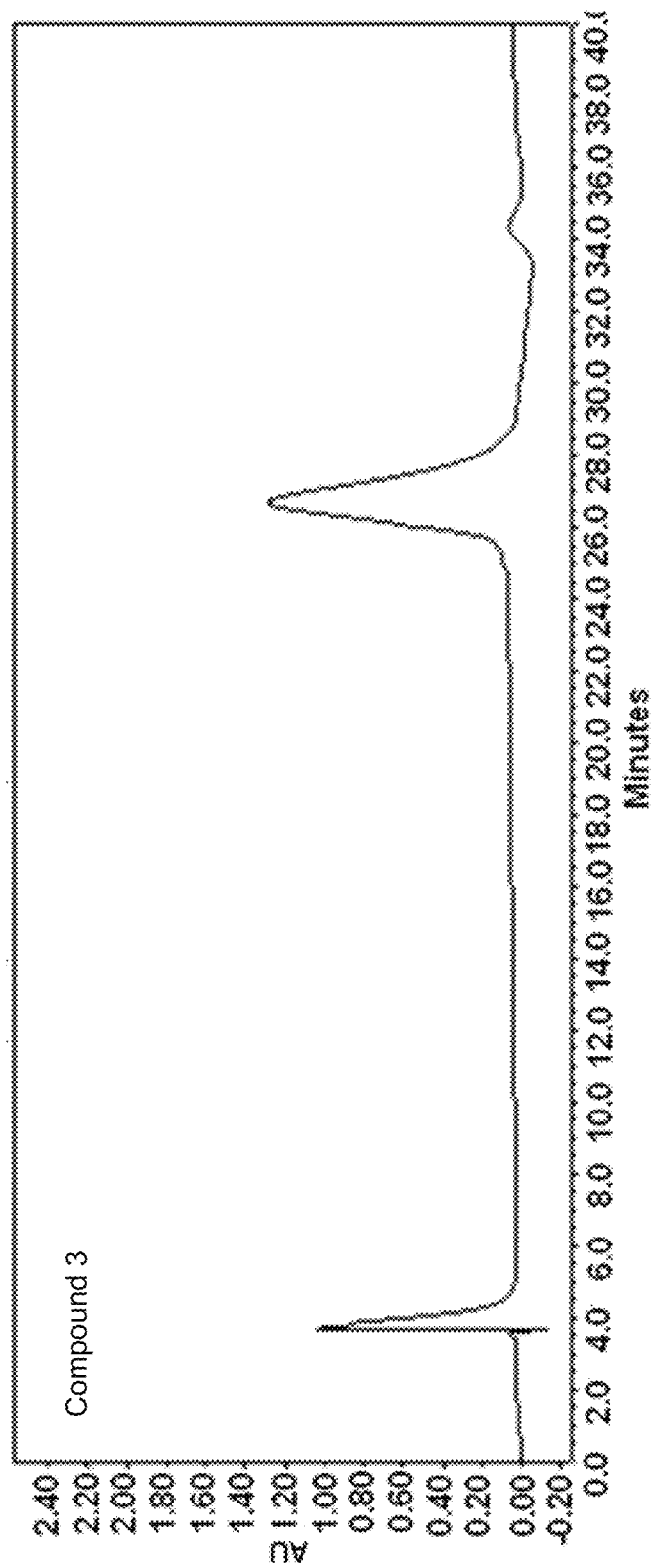

The coupling reaction between G4-PAMAM-$NH_2$ dendrimer (1) and Boc-Ser-NHS (2) was carried out in N, N-Diisopropylethylamine (DIEA) in a two component solution of DMSO/DMF. Because of the higher reactivity of the NHS group of Boc-serine-NHS (2) with amine terminations of G4-PAMAM-$NH_2$ (1), it is expected that the product will consist of Boc-Ser residues conjugated at the G4-PAMAM-$NH_2$ (1) by amide bond, the reaction was monitored by MALDI-TOF analysis to ensure complete substitution. The product so obtained was purified by dialysis using DMSO to remove the excess of unreacted Boc-Ser-NHS and other by products. The appearance of characteristic signals of Boc-Serine in the $^1$H NMR spectrum at 1.38 (s, 9H, Boc), 2.10-2.22 (br.s, OH), 3.22-3.38 (m, 1H, $CH_2$), 4.50-4.58 (m, 1H, $CH_2$) 4.80-4.90 (m, 1H, CH) 6.50-6.60 (m, 1H, NH amide), 7.78-7.97 (br. d, NH amide interior dendrimer amide), ppm of G4-PAMAM-NH—CO-Ser(OH)-NHBoc (3) (FIG. 2A) confirm the desired product. It is evident from the integral ratio of the amide protons of PAMAM-NH—CO-Ser(OH)-NHBoc at 7.78-7.97 ppm to the two methylene protons of serine at 3.22-3.38 (m, 1H, $CH_2$), 4.50-4.58 (m, 1H, $CH_2$) ppm, that each G4-PAMAM-$NH_2$ dendrimer contains approximately 58 Boc-serine molecules attached. The MALDI-TOF/Ms analysis of G4-PAMAM-NH—CO-Ser (OH)-NHBoc (3) shows the appearance of molecular mass peak at 24.5 kDa (FIG. 2B). For G4-PAMAM dendrimer the measured molecular weights (13.7 kDa) were lower than the theoretical value (14.21 kDa). The corresponding increase in mass from 13.7 kDa (G4-PAMAM-NH) to 24.5 kDa for G4-PAMAM-NH—CO-Ser(OH)-NHBoc (3), confirms attachment of 58 Boc-serine molecules since the molecular weight of serine is 205 Da. This further supports the NMR data which showed attachment of 58 molecules. The conversion of symmetrical terminal amines of G4-PAMAM to hetero-bifunctional 'OH' and 'NHBoc' terminal groups was 84%. The results show that a high degree of surface functionalization has occurred. The PAMAM dendrimers have predominant structural defects in the starting compounds themselves and these were previously known to preclude the complete conversion. The HPLC chromatogram (210 nm) shows a single peak corresponding to G4-PAMAM-NH—CO-Ser(OH)-NHBoc (3), confirming the purity of the product (FIG. 2C).

Figure 3A:
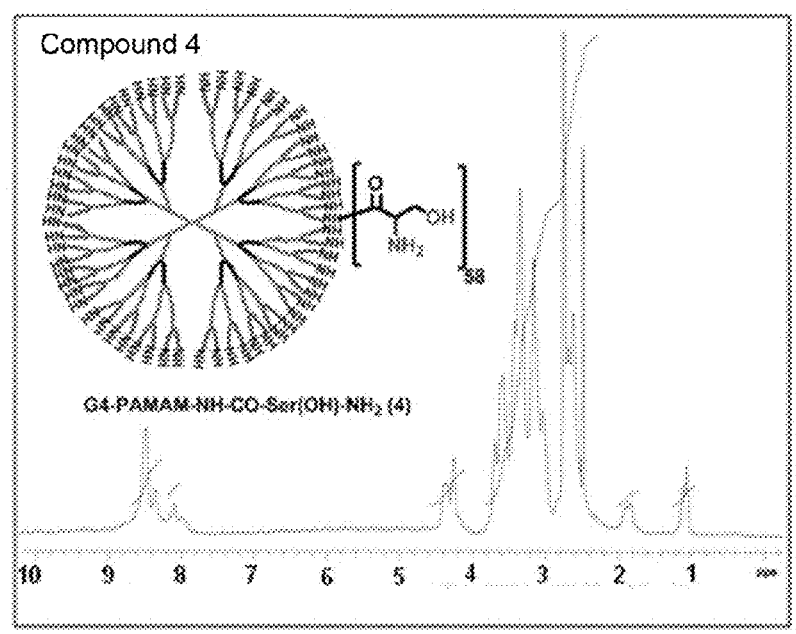
FIGS. 3 A-C show $^1$H NMR (FIG. 3A), MALDI TOF/MS spectrum (FIG. 3B) and HPLC chromatogram (FIG. 3C) for G4-PAMAM-NH—CO-Ser(OH)—NH$_2$ (Compound 4).
Figure 3B:
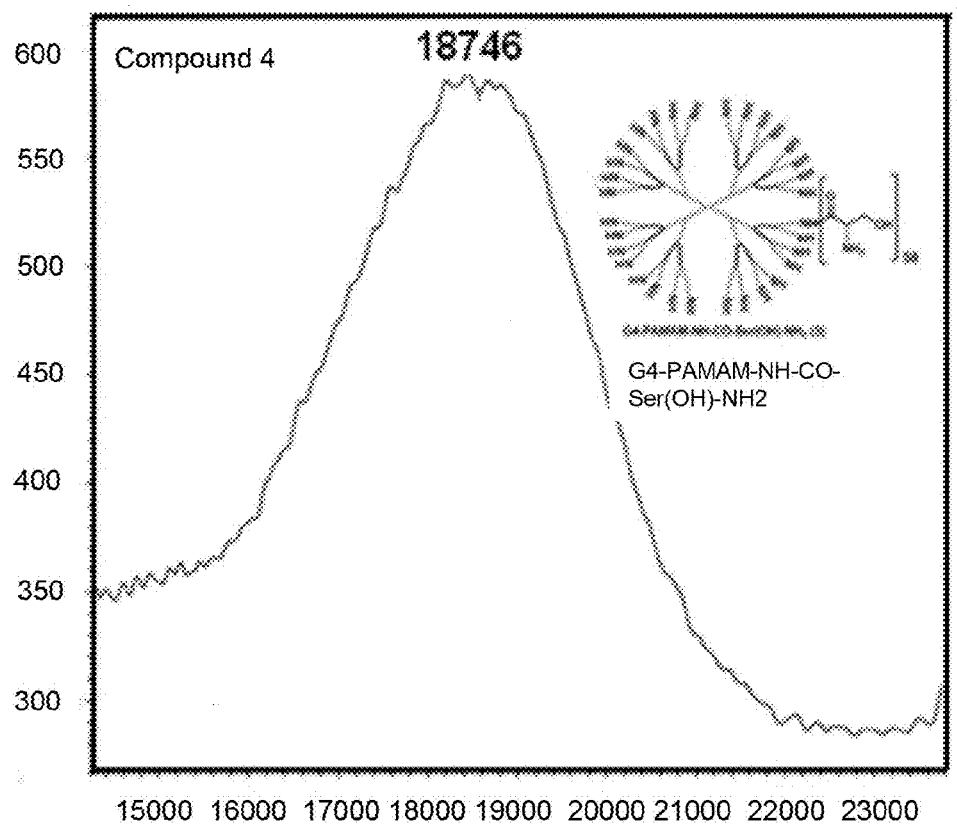
Figure 3C:
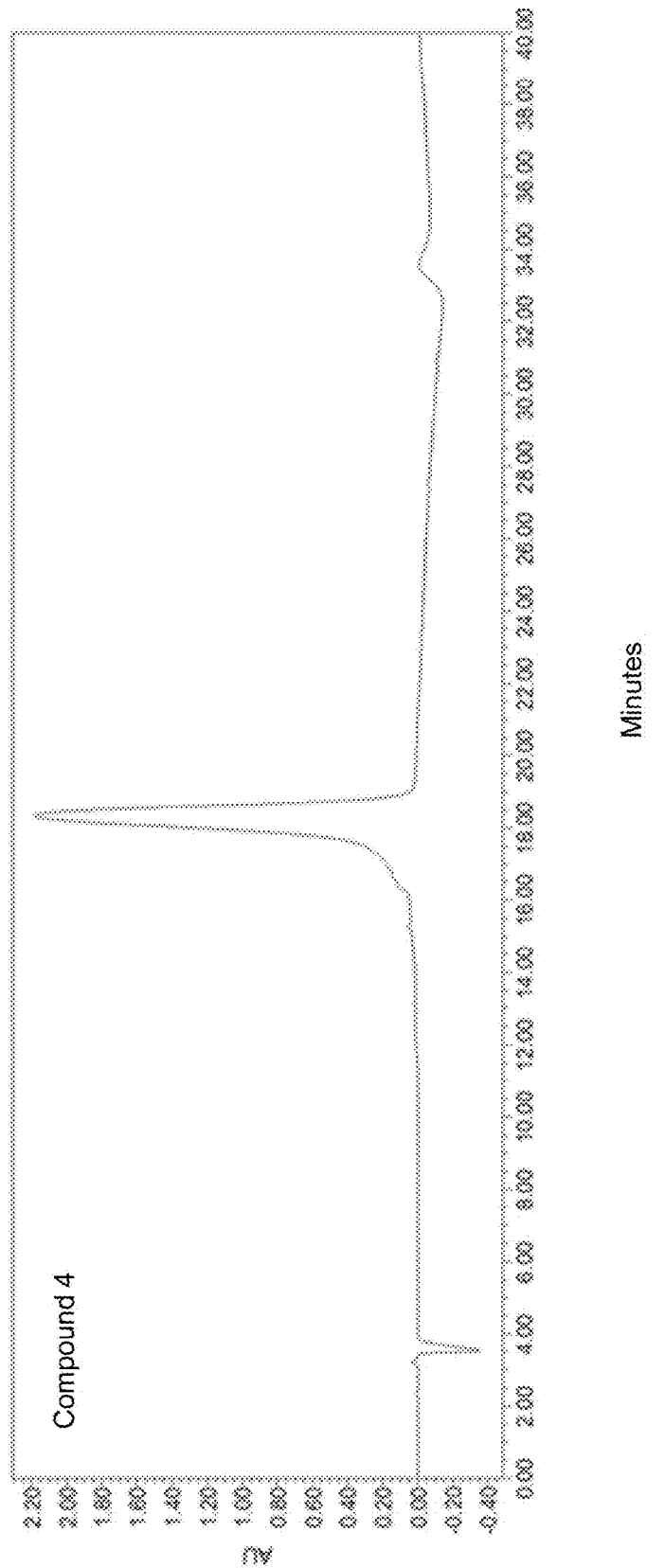

Achieving 'near complete' attachment of the Boc-serine moieties on the dendritic core was challenging. One of the probabilities was steric hindrance avoids the conjugation of the bulky molecules. When the attachment of cysteine with one protecting group (6, 13) and two protecting groups (28) was compared, to G4-PAMAM-OH (12), a drastic reduction in number of cysteines (28) attached to dendrimer was observed. This shows that presence of thiopyridyl and tert-Butoxycarbonyl protecting groups makes the cysteine (28) molecule bulky and hence causes stearic hindrance leading to lower number of cysteines (28) attached to the dendrimer vis a vis cysteine (5) with one protecting group. A single broad peak was observed in MALDI-TOF/Ms spectrum (FIG. 2B) and the peak corresponding to dendrimer (starting compound) at ~14.2 kDa was not observed in this spectrum indicating that the peak at 24.5 kDa belongs to the obtained G4-PAMAM-Ser-(OH)-NHBoc (3) compound. Further, the spectrum did not show multiple peaks confirming the absence of other by products. The $^1$H NMR spectra and MALDI-TOF/Ms for G4-PAMAM-Ser-(OH)-NHBoc dendrimer (3) collectively suggest attachment of 58 molecules of Boc-Serine to G4-PAMAM-NH$_2$. The evaluations suggested that the 2-fold excess of serine was sufficient to achieve the complete end capping of the G4-PAMAM-NH$_2$ dendrimer (1) to provide G4-PAMAM-Ser-(OH)-NHBoc dendrimer (3). The above compound so obtained was further used to get amine terminations at the periphery attained by global deprotection of the tert-Butoxycarbonyl (Boc) groups using trifloroacetic acid (scheme-1) and the resulting hetero-bifunctional dendrimer (4) can be then utilized in a variety of subsequent conjugation reactions. The characteristic signals of tertbutyl groups appearing at 1.30 (s, 9H) in $^1$H NMR spectrum of (4) disappear on deprotection but the other peaks corresponding to serine are seen at $^1$H NMR spectrum at δ, 1.0-1.19 (m, 2H, NH$_2$), 1.80-1.98 (br. s, 1H, OH), 4.21-4.26 (s, 1H), 8.0-8.15 (br. d from amide NH), 8.30-8.60 (br. d, amide NH) ppm of G4-PAMAM-NH—CO-Ser(OH)—NH$_2$ (4) (FIG. 3A) confirm the desired product. It is evident from the integral ratio of the amide protons of PAMAM-NH—CO-Ser(OH)-NHBoc at 8.30-8.60 ppm to the two methylene protons of serine at 3.50-3.68 (m, 2H, CH$_2$) ppm, that each PAMAM-NH$_2$ dendrimer contains approximately 58 serine molecules attached. After deprotection, the molecular weight decreased from 24.5 kDa for (3) to 18.7 kDa for (4) (FIG. 3B). The mass of G4-PAMAM-NH$_2$ dendrimer is 13.7 kDa and this increase to 18.7 kDa corresponds to 58 molecules of serine attached since the molecular weight of serine is 105 Da. The HPLC chromatogram (210 nm) shows a single peak corresponding to G4-PAMAM-NH—CO-Ser(OH)—NH$_2$ (4), confirming the purity of the product (FIG. 3C). The diverse end groups so obtained are amenable for post-functionalization modifications or reactions. The high density of diverse end groups is achieved through a choice of the end termination of parent scaffold and the reacting amino acid. Different permutations of the end group functionality of the dendrimers were explored and several amino acids to develop a library of hetero-bifunctional dendrimers (Table 1 (Library of Amino Acid Surface Modified Dendrimers) and Table 2 (Molecular weight estimation of amino acid functionalized dendrimers)).

Other hetero-bifunctional dendrimers (6, 10, 13, 16, 28) bearing 'SH+NHBoc' and 'COOMe+OH' terminal groups were synthesized by reacting G4-PAMAM-NH$_2$ dendrimer (1), G3.5-PAMAM-COOH dendrimer (8) and G4-PAMAM-OH (12) with Boc-Ser-NHS (2), Boc-Cys-NHS (4) and Boc-Ser-OMe respectively (Scheme 2-5, 7).

Schemes 3-4 are schematic representations for synthesis of G3.5-PAMAM-CO—NH-Ser(OH)—COOMe (10) and G4-PAMAM-O—CO-Cys(SH)-NHBoc (13) Compounds (10 and 13) show the conversion of symmetric peripheral acid of G3.5-PAMAM-NH$_2$ (8) into hetero bifunctional terminal groups 'COOMe+OH' and 'SH+NHBoc' respectively. The compounds 10, 13 was further hydrolysis of methyl ester and Boc gave compounds 'COOH+OH' and 'SH+NH$_2$' respectively.

Scheme 5 is a schematic representation for the post-functionalization reactions of hetero-bifunctional dendrimers showing conjugation of multiple drugs and or imaging agents in immediate succession. G4-PAMAM-O-Asp (COOH)—NH$_2$ (17) dendrimer bearing COOH and NH$_2$ termini was synthesized. Dexamethasone was conjugated to G4-PAMAM-O-Asp(COOH)—NH$_2$ (16) and indomethacin was added to achieve G4-PAMAM-O-Asp(CO-Dex)-NH-Ind (22). Similarly, FITC was conjugated in immediate succession to G4-PAMAM-O-Asp(CO-Dex)-NH$_2$ (20) to yield G4-PAMAM-O-Asp(CO-Dex)-NH-FITC (24).

Scheme 6 is a schematic representation for the post-functionalization reactions of hetero-bifunctional dendrimers showing conjugation of drug (e.g. dexamethasone) to one functional handle while the other functional handle is used for hydrogel formation (26) with N-hydroxysuccinmide terminated 8-arm-polyethylene glycol (25).

Scheme 7 is a schematic representation for the formation of hydrogel involving one of the functional handles of the G4-PAMAM-O—CO-Cys(S-TP)-NH$_2$ dendrimer while the 'NH$_2$' handle is available for further modifications. The thiol terminated 8arm PEG (20 kDa) formed gel at pH 7.4 by reacting with the dithiopyridine terminations of the G4-PAMAM-O—CO-Cys(S-TP)-NH$_2$ resulting in disulfide linkages.

Scheme-8. G4-NH—CO-Cys(S-TP) cross linked with 8-arm-PEG-SH to form dendrimer-PEG nanogel (or nanopartcles)

Scheme-9. G4-NH-PDP cross linked with 8-arm-PEG-SH to form G4-FITC encapsulated dendrimer-PEG nanogel (or nanopartcles)

Scheme-10: FITC-G4-NH-PDP cross linked with 8-arm-PEG-SH to form dendrimer-PEG nanogel (or nanopartcles)

Scheme-11: HBVS cross linked with G4-O-Cys(SH)—NH—FITC and 8-arm-PEG-SH to form dendrimer-PEG nanogel (or nanopartcles)

Scheme-12: FITC-G4-NH-Mal cross linked with 8-arm-PEG-SH to form dendrimer-PEG nanogel (or nanopartcles)

Scheme-13: G4-O—CO-Cys(S-Tp)-NH$_2$ cross linked with Meo-PEG-SH to form dendrimer-PEG nanogel (or nanopartcles)

Scheme-14: G4-O—CO-Cys(SH)—NH$_2$ cross linked with PDP-PEG-PDP to form dendrimer-PEG nanogel (or nanopartcles)

The compounds 3, 6, 13, 16, 28 on global deprotection of Boc groups with trifloroacetic acid and dichloromethane gave 7, 14, 17, 29 and compound 10 on hydrolysis of methyl ester with lithium hydroxide in tetrahydrofuran/water (THF/H$_2$O) gave compound 11. The Table 1 gives the PAMAM dendrimer scaffold and the respective amino acids used to functionalize the periphery. The % conversion, and number of amino acids attached to the dendrimer is given in Table 2. In the past, it has been reported that attachment of 64 groups of phenylalanine on G4 dendrimer resulted in a significant reduction in the water solubility of the compound. Herein, all the compounds with significantly high end group modifications of G4-PAMAM dendrimers with amino acids resulted in highly water soluble compounds (4, 7, 11, 14, and 17).

Conjugation of Drugs and Imaging Agent on One Terminal Group and Formation of Hydrogel Using the Other.

The orthogonal and chemoselective nature of the peripheral end groups in the hetero-bifunctional dendrimers was demonstrated by conjugation of (i) two drugs viz dexamethasone and indomethacin (ii) indomethacin, and an imaging agent (FITC) on the aspartic acid surface modified PAMAM dendrimer (16) (Scheme-5). In addition, the in-situ hydrogel formation using only one functional handle of the hetero-bifunctional dendrimer is demonstrated, while the second functional handle is used for drug conjugation as shown in Scheme-6.

Figure 4A:
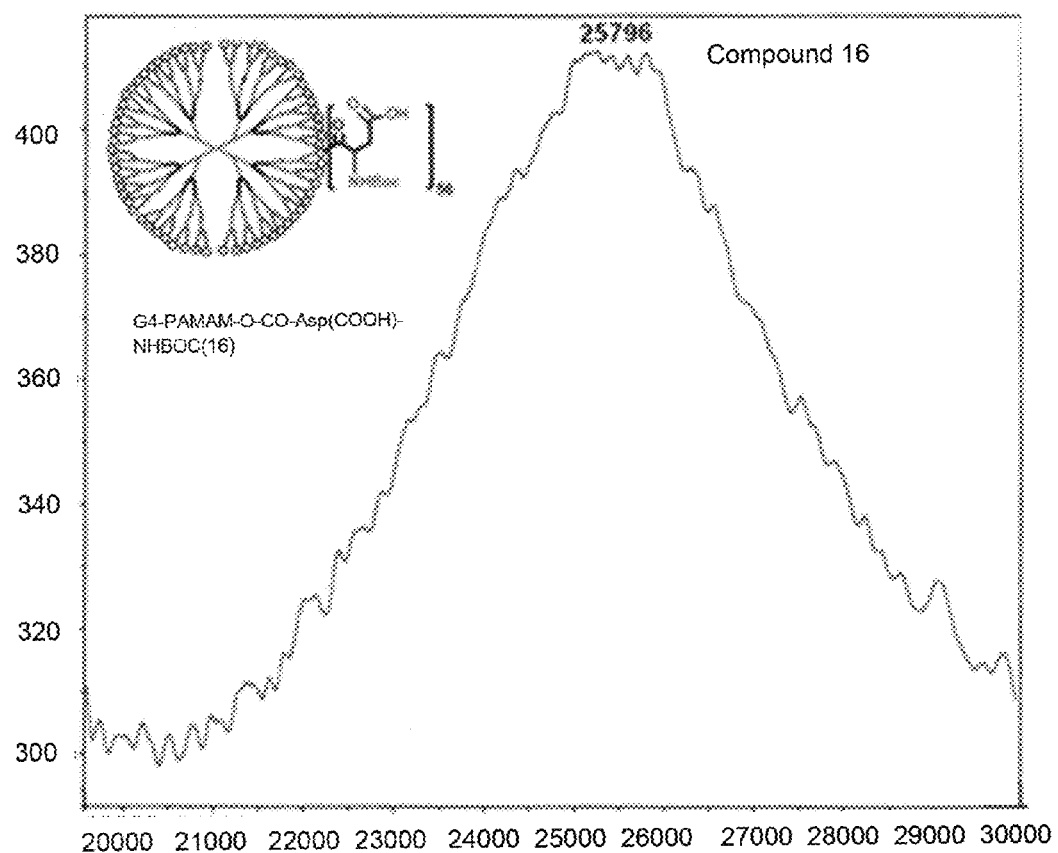
FIG. 4A) showing mass of 25.7 kDa. On deprotection of Boc groups G4-PAMAM-O-Asp(COOH)—NH$_2$ (Compound 17.
Figure 4B:
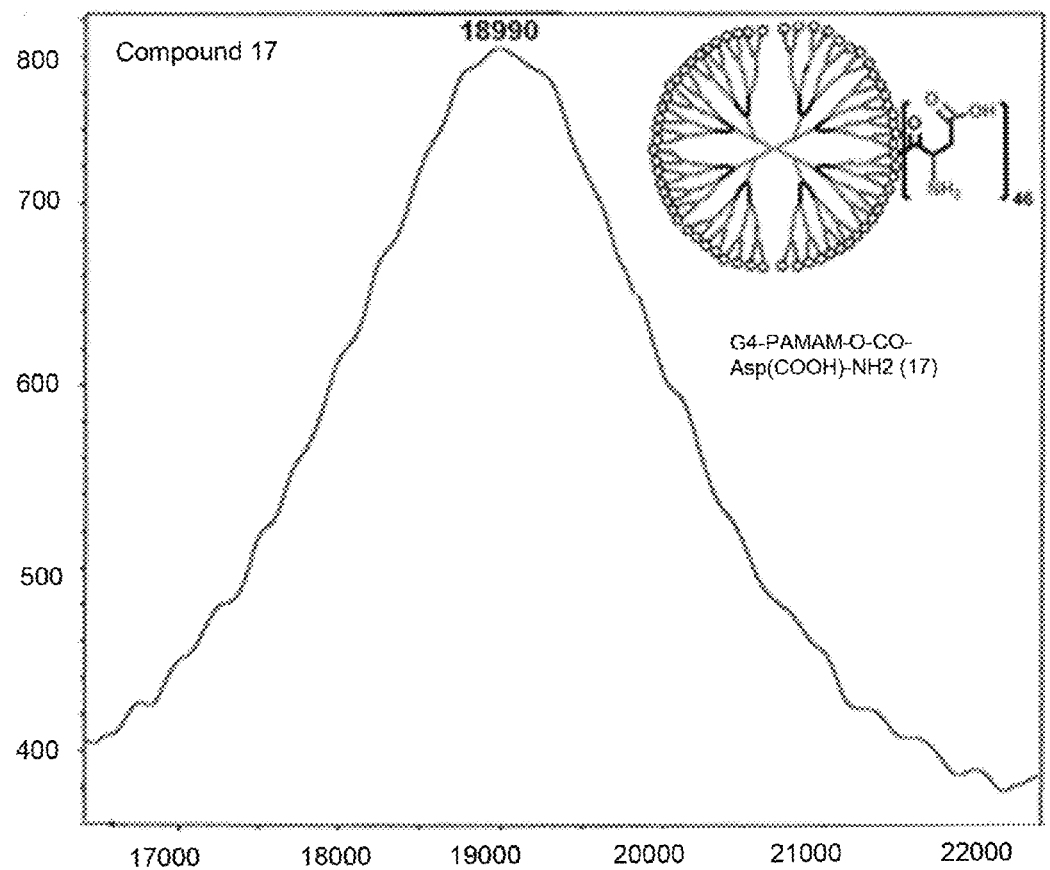
FIG. 4B) dendrimer showed a mass of 18.9 kDa. The conjugation of dexamethasone to (Compound 16) decreases after Boc deprotection the mass to 21.9 kDa (Compound 20.
Figure 5A:
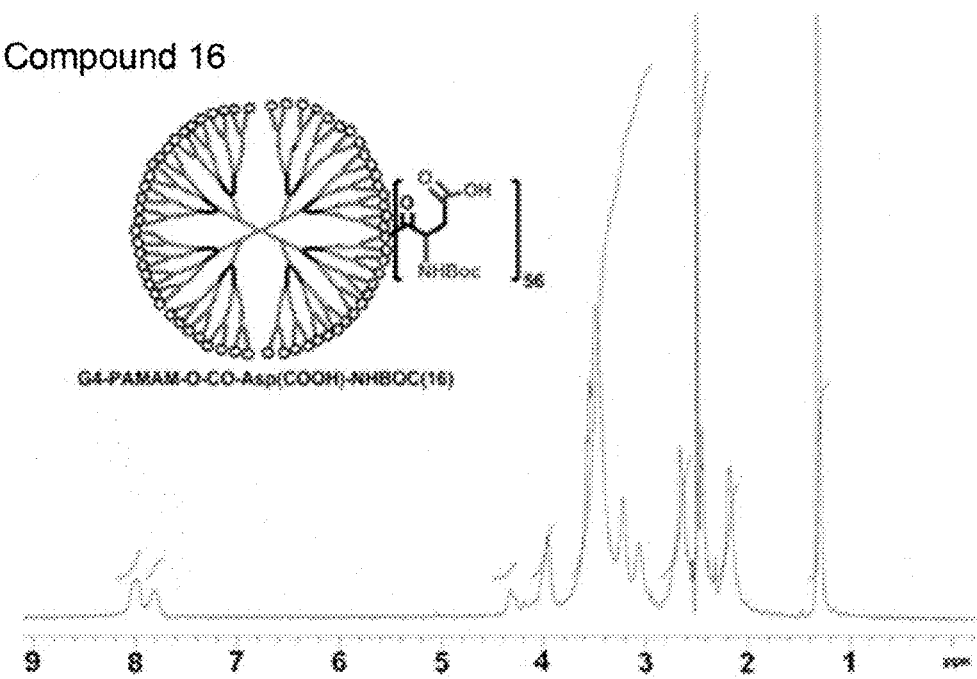
FIG. 5A), after deprotection of tert-Butoxycarbonyl groups G4-PAMAM-O-Asp(COOH)—NH$_2$ (Compound 17.
Figure 5B:
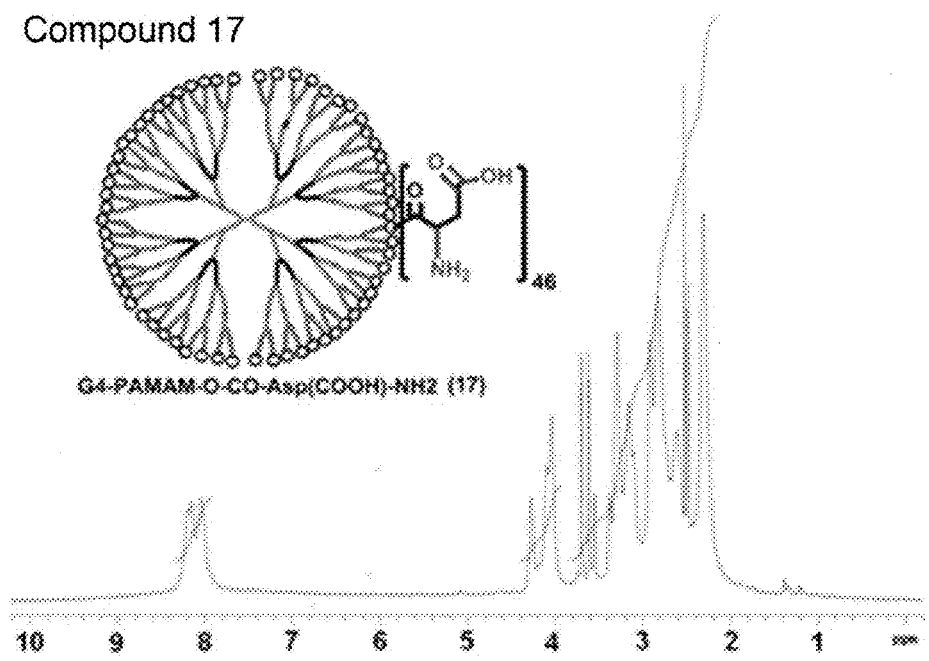
FIG. 5B), the conjugation of dexamethasone to give G4-PAMAM-O-Asp(CO-Dex)-NH$_2$ (Compound 20) and further the attachment of indomethacin G4-PAMAM-O-Asp(CO-Dex)-NH-Ind (Compound 22.
Figure 6A:
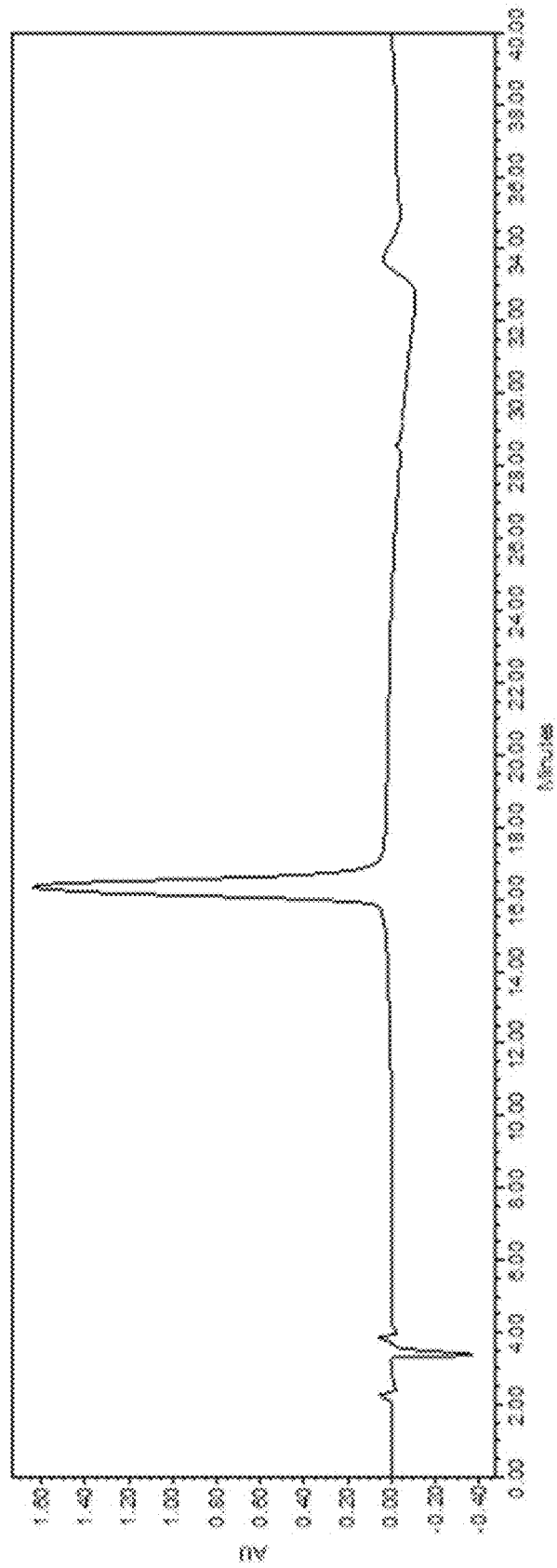
(FIG. 6A) G4-PAMAM-Asp-(COOH)—NHBoc showing retention time 16.5 minutes, (FIG. 6B) G4-PAMAM-Asp-(COOH)—NHBoc spiked with dexamethasone, the dexamethasone appears at 22.8 minutes, (FIG. 6C) G4-PAMAM-Asp-(CO-Dex)-NH$_2$ showing retention time 20.5 minutes, (FIG. 6D) G4-PAMAM-Asp-(CO-Dex)-NH-Ind spiked with indomethacin, the unconjugated indomethacin appears at 25.8 minutes, (FIG. 6E) G4-PAMAM-Asp-(CO-Dex)-NH-Ind appears at 22.7 minutes.
Figure 6B:
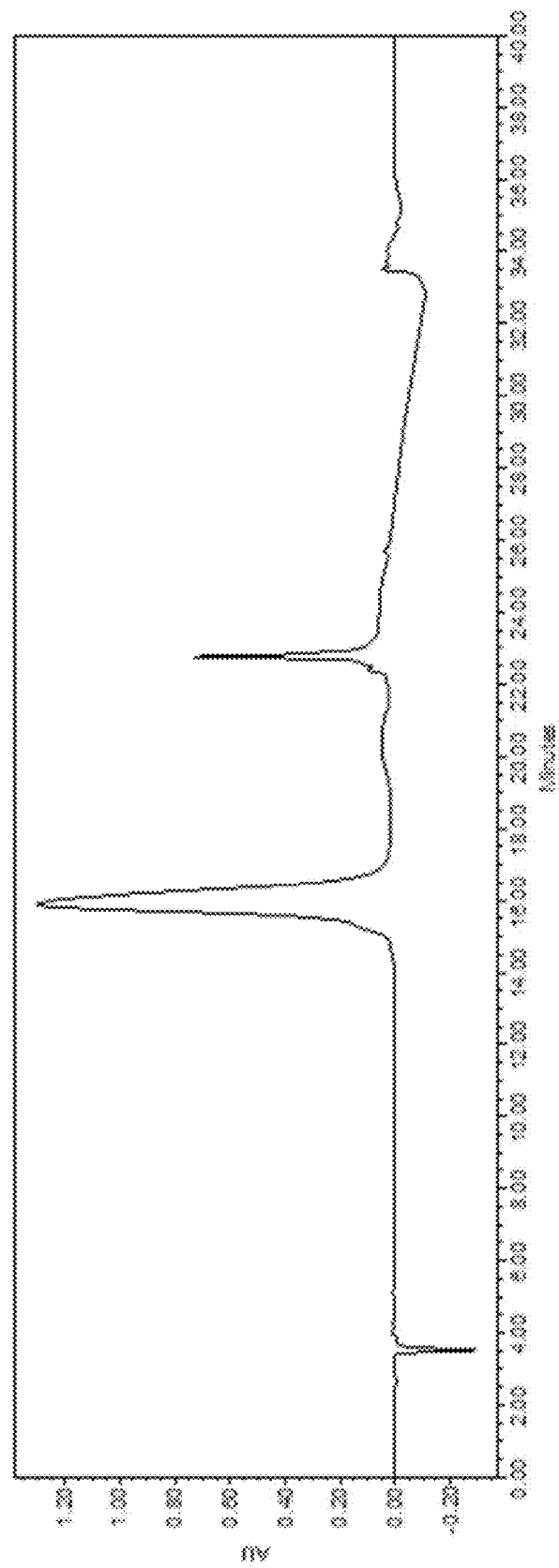
FIG. 6 shows the HPLC chromatograms absorbance at 210 nm (arbitrary AU units) for G4-PAMAM-Asp-(COOH)—NHBoc and its postfunctionalization products.

A hetero-bifunctional G4-PAMAM dendrimer bearing 'carboxylic' and 'Boc-amine' peripheral terminations, to facilitate the diverse post-functionalization reaction was obtained by reacting the 'hydroxyls' of G4-PAMAM-OH (12) with Boc-aspartic acid (15). The coupling reaction of G4-PAMAM-OH dendrimer (12) with Boc-aspartic acid (15) was carried out using EDC/DMAP (scheme-5) to obtain G4-PAMAM-O-Asp(COOH)-NHBoc (16). MALDI-TOF/Ms of the functionalized dendrimer (16) reveals the mass peak at 25.7 kDa as seen from the mass spectrum (FIG. 4A). The molecular weight of Boc-Aspartic acid is 233 Da and so the increase from ~14 kDa for G4 PAMAM-OH (12) to 25.7 kDa corresponds to 56 molecules of Boc-aspartic acid (15) attached to G4-PAMAM-O-Asp(COOH)-NHBoc (16). The appearance of characteristic signals of Boc-Asp-OH in the $^1$H NMR spectrum at 1.30 (s, 9H), 2.10-2.20 (m, 2H), 4.50-4.60 (br. s, 1H), 7.19-7.24 (br.s, amide NH), of G4-PAMAM-O—CO-Asp(COOH)-NHBoc (16) (FIGS. 5A and 5B) confirm the desired product. It is evident from the integral ratio of the amide protons of PAMAM-O—CO-Asp(COOH)-NHBoc at 7.70-8.05 (br. d, amide NH) to the two methylene protons of Boc-Asp-OH 2.10-2.20 (m, 2H) that each PAMAM-OH dendrimer contains approximately 56. It is estimated that the extent of surface functionalization is 80% by taking the average of the MALDI/MS and NMR data and purity of the compound confirmed by RP-HPLC (FIG. 6A). On repeating the synthetic procedure several times 56 molecules could be conjugated, rather than the theoretical ~64 that are available, resulting in a total of 112 end functionalities (56+56 each). The structural defects in the starting compounds themselves (PAMAM dendrimers) could attribute for the observed effect. Both the MALDI and NMR, analysis do not account for the small structural imperfections. The results show a high degree of conversion (80%) of 'OH' terminal groups into 'COOH and Boc-NH' groups. In addition to carboxylic groups the amine terminations at the periphery are attained by global deprotection of the tert-Butoxycarbonyl (Boc) groups using trifloroacetic acid (scheme-5) and the resulting hetero-bifunctional dendrimer (17) can then be utilized in a variety of subsequent conjugation reactions. The characteristic signals of tert-butyl groups appearing at 1.30 (s, 9H) in $^1$H NMR spectrum of (17) disappear on deprotection but the other peaks corresponding to aspartic acid are seen at 2.20-2.38 (m, 2H), 4.22-4.31 (br.s, 1H), 7.96-8.10 (br. s, amide NH). 8.10-30 (br. d, amide, NH). After deprotection, the molecular weight decreased from 25.7 kDa for (16) to 18.9 kDa for (17) (FIGS. 4A and 4B), since the molecular weight of aspartic acid is 133 Da the mass of 15 corresponds to 46 molecules of the aspartic acid appended on the dendrimer thereby yielding a total of 92 end functionalities (46+46 each). Yet there is a merit in this scaffold as it has a high density of diverse end groups as compared to G4-PAMAM-OH dendrimer.

Figure 4C:
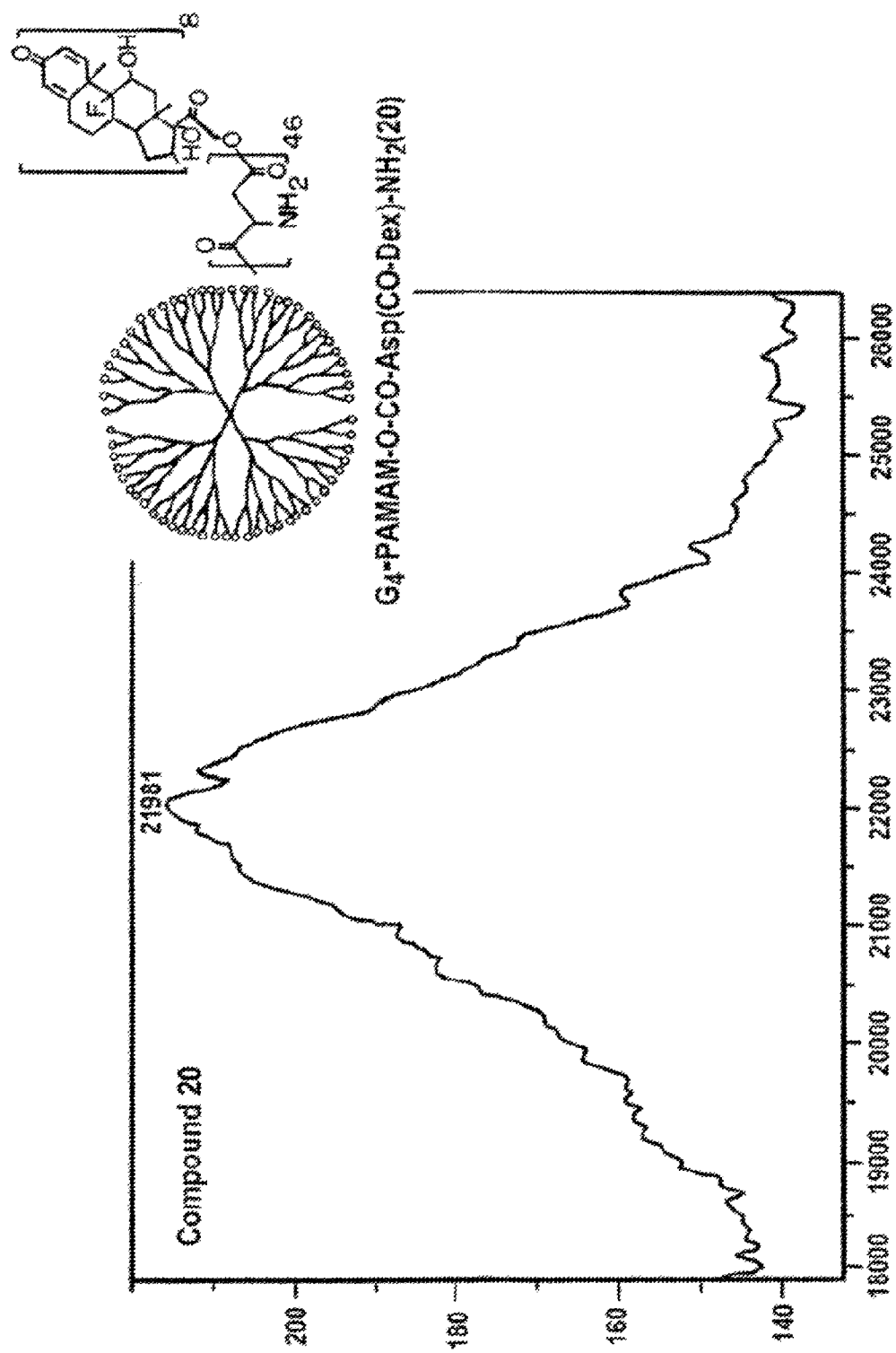
FIG. 4C). Further the attachment of indomethacin on (Compound 20) increases the mass to 30.1 kDa on formation of G4-PAMAM-O-Asp(CO-Dex)-NH-Ind (Compound 22.
Figure 5C:
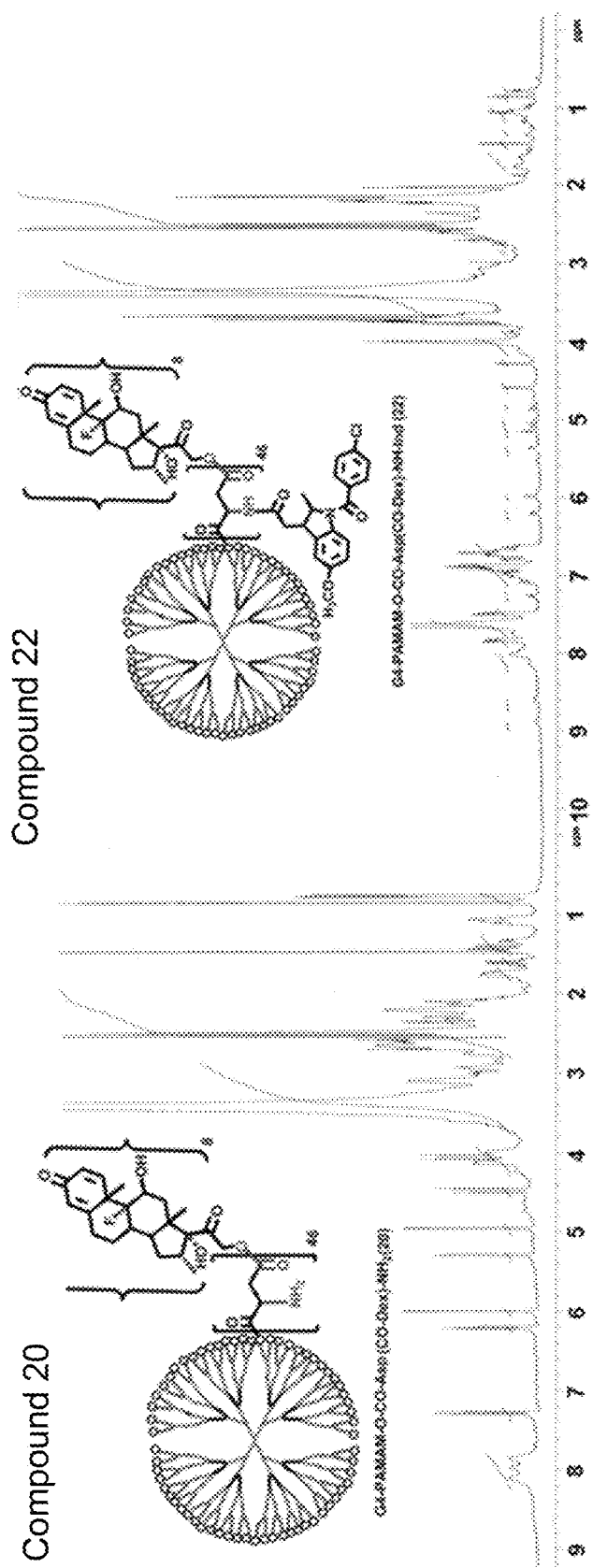
FIG. 5C).
Figure 6C:
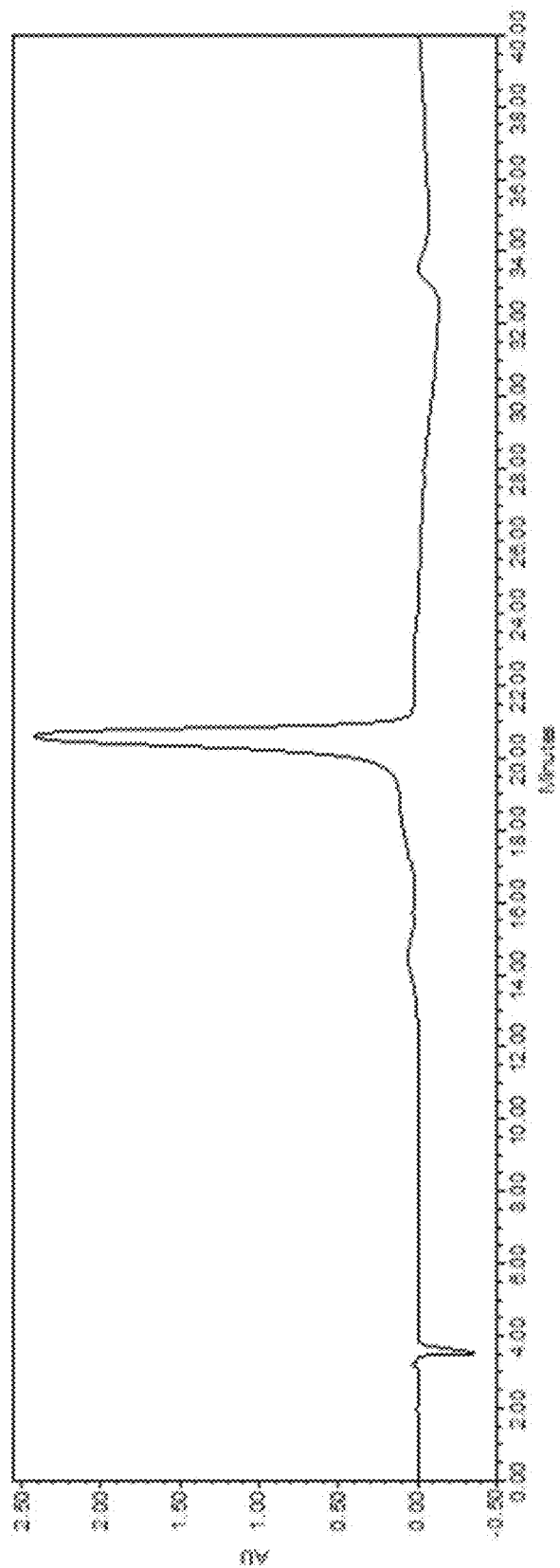
Figure 6D:
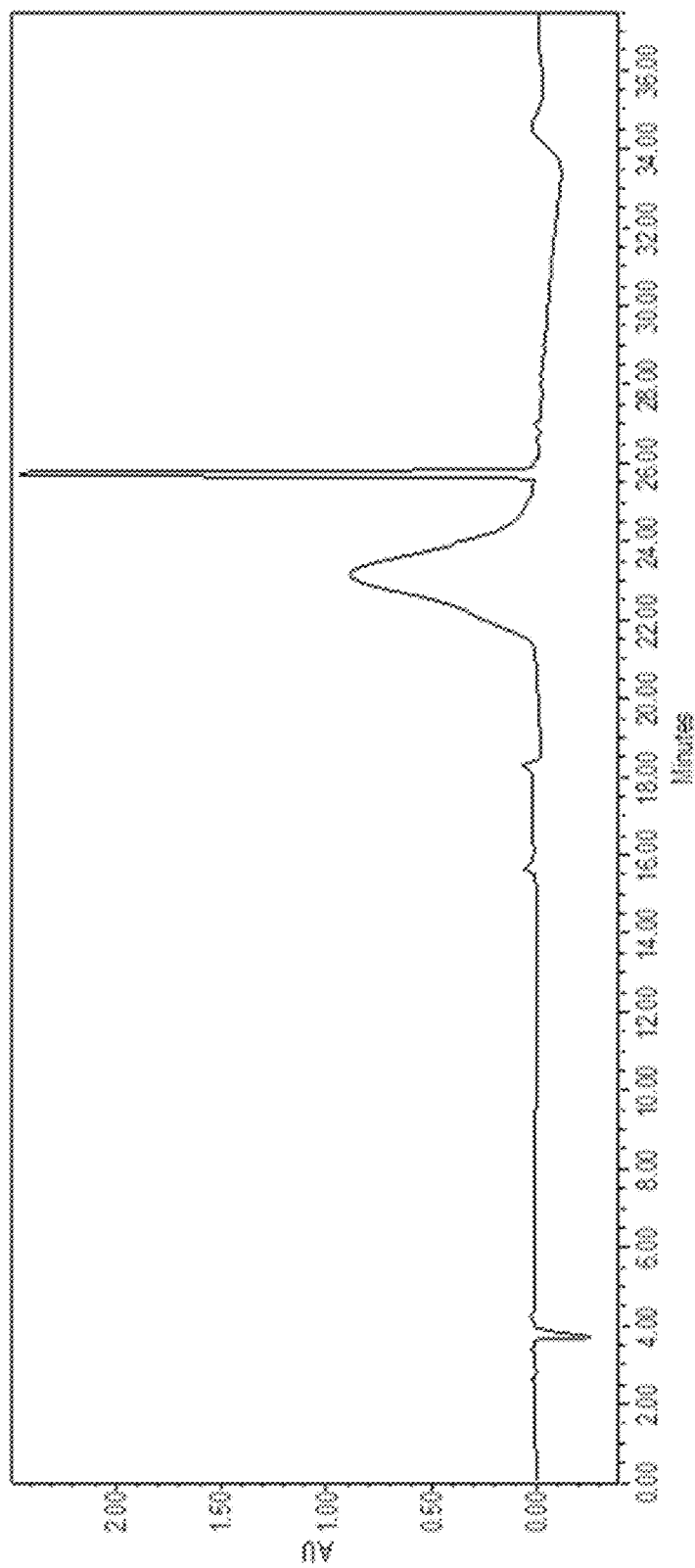

To test if the terminal groups are amenable to further modification, the G4-PAMAM-O-Asp(COOH)-NHBoc (16) was reacted with dexamethasone (18) as a model steroidal anti-inflammatory drug involving the carboxylic end groups on dendrimer to link the drug by ester bond using EDC/DMAP as coupling reagents (Scheme-5). Compound (19) was used without further characterization to get amine terminations at the periphery by global deprotection of the tert-Butoxycarbonyl (Boc) groups using trifloroacetic acid (scheme-5) and the resulting (20) can be then utilized in a variety of subsequent conjugation reactions. The formation of G4-PAMAM-O-Asp(CO-Dex)-NH$_2$ (20) conjugate was validated by $^1$H NMR analysis. The appearance of dexamethasone methyl protons at 0.75 (s, 3H), 0.82 (s, 3H) and 1.45 (s, 3H), double bond protons at 6.01 (s, 1H) 6.23 (d, 1H) and 7.30 (d, 1H), confirm the conjugation between G4-PAMAM-O-Asp(COOH)-NHBoc (16) and Dexamethasone (18) (FIGS. 5A, 5B, and 5C). The attachment of multiple copies of dexamethasone to G4-PAMAM-O-Asp(COOH)-NHBoc (16) dendrimers was determined by MALDI-TOF/Ms and purity of the compound confirmed by RP-HPLC (FIG. 6C). The attachment of dexamethasone followed by Boc deprotection shifted the mass of G4-PAMAM-O-Asp(CO-Dex)-NH$_2$ dendrimer from 25.7 kDa to 21.9 kDa (FIGS. 4A and 4C). Dexamethasone (18) has a molecular weight of 392 Da, therefore, the incremental mass corresponds to average of 8 molecules of dexamethasone molecules per dendrimer (number attained from 3 independent experiments).

Figure 4D:
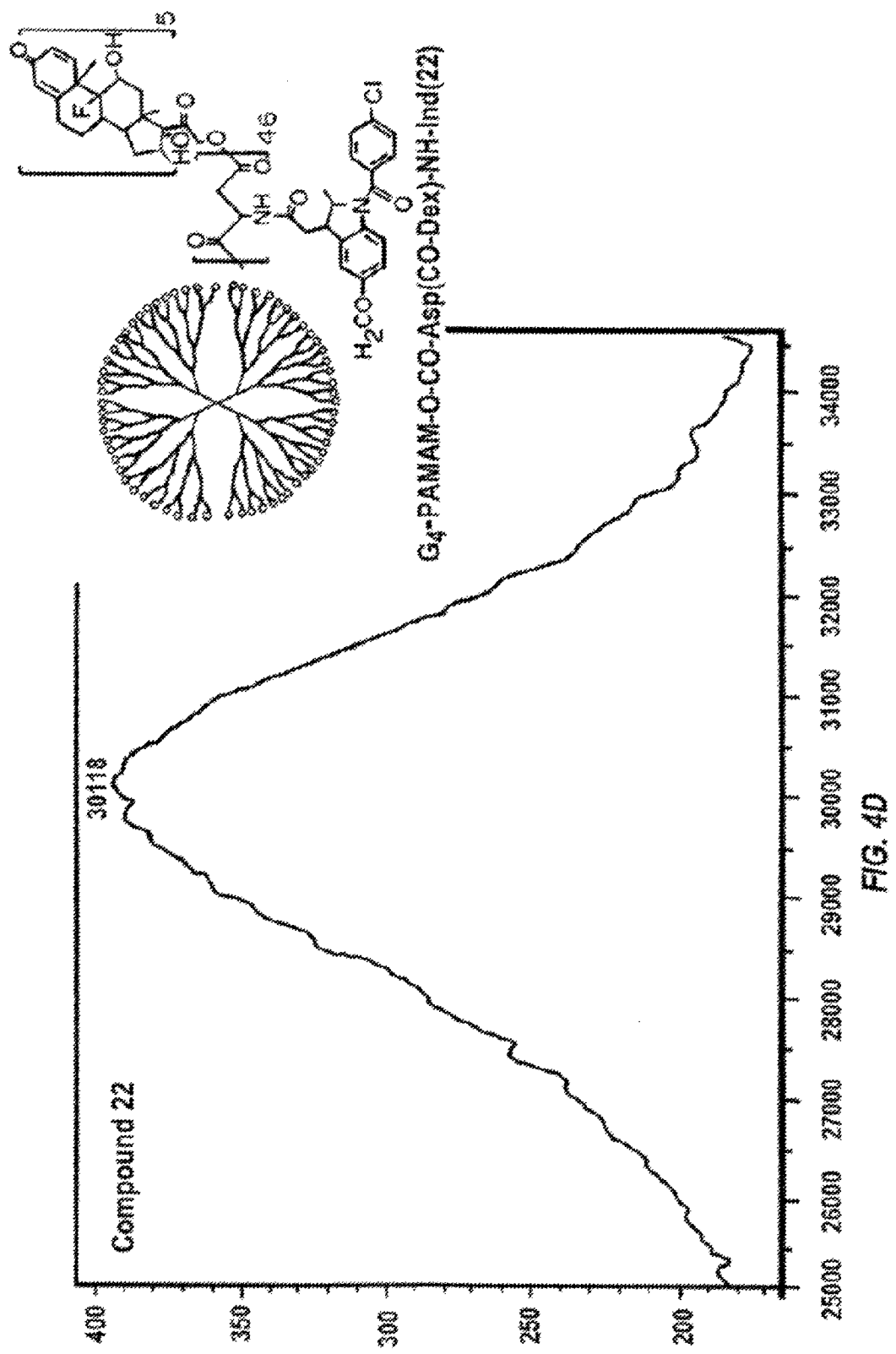
FIG. 4D).
Figure 6E:
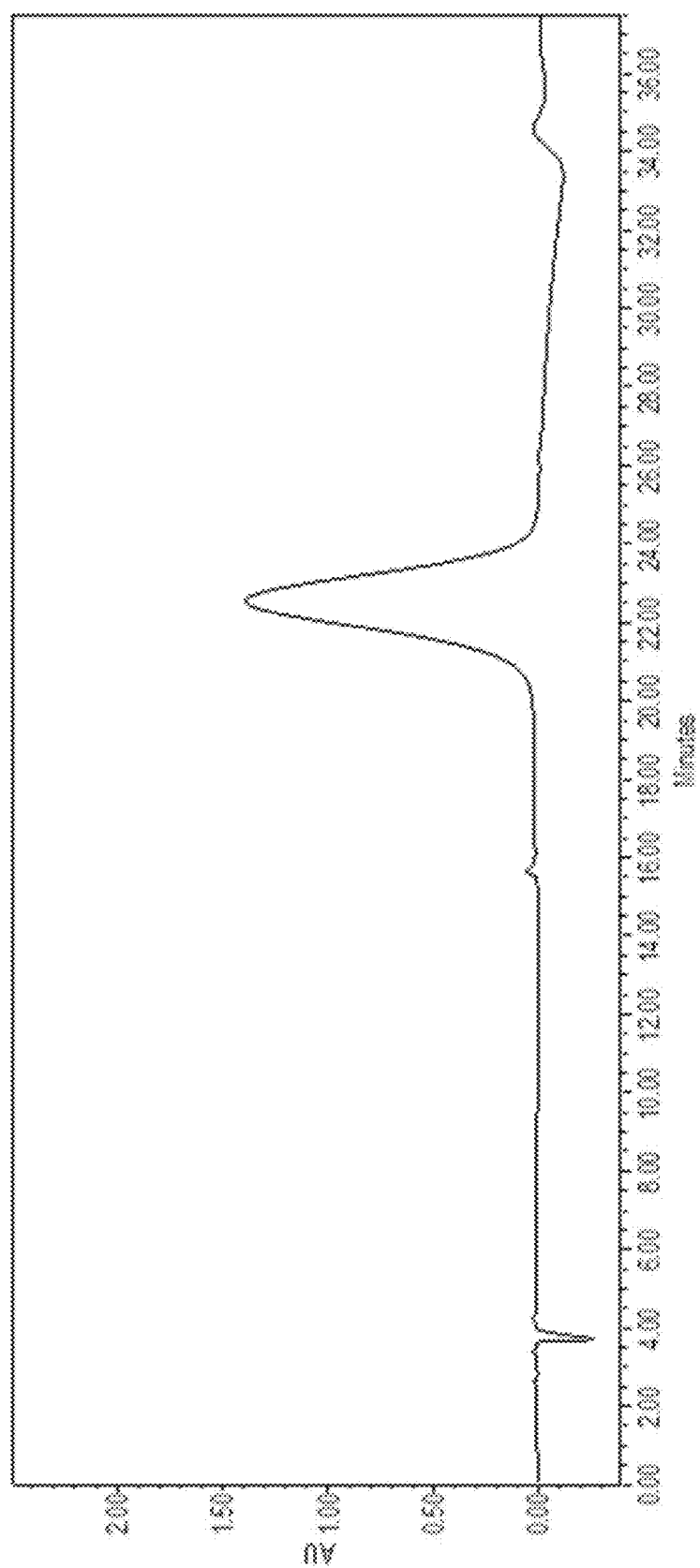

To examine this further, the possibility of the conjugation of second drug to the hetero-bifunctional dendrimer (20) in immediate succession, the G4-PAMAM-O-Asp-(CO-Dex)-NH$_2$ (20) was reacted with indomethacin (21) without the need to attach additional spacer or linker molecules. Indomethacin was chosen as another model drug which belongs to a class of anti-inflammatory drugs. The conjugation was carried out in presence of EDC/DMAP as coupling reagents (Scheme-5). The $^1$H NMR analysis shows that the aromatic protons corresponding to indomethacin appear at 2.10-2.30 (m, 3H, CH$_3$) 3.62-3.80 (m, 5H, —OCH$_3$, —CO—CH$_2$—) 6.60-6.79 (m, 2H, Ar), 6.63-7.04 (m, 2H, Ar), 7.60-7.70 (m, 3H, Ar) confirming the conjugation of indomethacin to G4-PAMAM-O-Asp(CO-Dex)-NH$_2$ (20) to yield G4-PAMAM-O-Asp(CO-Dex)-NH-Ind (22) (FIG. 5C). The purified dendrimer conjugate was subjected to MALDI-TOF analysis and the obtained mass exhibited an increase from 21.9 kDa (for 20; FIG. 4C) to 30.1 kDa (for 22; FIG. 4D) as expected and purity of the compound confirmed by RP-HPLC (FIG. 6E). The increase in molecular weight corresponds to an average of 24 indomethacin molecules per dendrimer molecule, since indomethacin has a molecular mass of 357 Da, suggesting an overall 36 loading of dexamethasone and indomethacin (number attained from 3 independent experiments). The $^1$H NMR analysis showed that any undesired side products were not observed suggesting the clean attachment of two drugs (both dexamethasone and indomethacin).

Polymeric scaffolds used in drug delivery are often tagged with imaging agents and radio nucleotides to investigate their distribution pattern in-vitro and in-vivo. This attachment could be direct on to the scaffold or mediated through an appropriate linking chemistry, which may at times require a suitable spacer molecule. As shown herein, the carboxylic terminations G4-PAMAM-O-Asp-(CO-Dex)-NHBoc (20) were consumed for esterification with Dexamethasone (18), but the presence of Boc-amine groups bestowed flexibility to explore after Boc deprotection for direct attachment of fluorescent imaging dye (FITC) (23) by thiourea bond. This demonstrated the ability of the hetero-bifunctional dendrimers to attach to drug and an imaging agent in immediate succession without any further modification thereby excluding the additional synthetic steps to append a suitable spacer to the dendrimer scaffold. G4-PAMAM-O-Asp-(CO-Dex)-NH$_2$ (20) conjugate was tagged with FITC (23) (scheme-5) in one step by adding FITC (23) to a solution of G4-PAMAM-O-Asp-(CO-Dex)-NH$_2$ (20) in DMSO and the reaction was stirred at room temperature in dark. The FITC-labeled G4-PAMAM-O-Asp(CO-Dex)-(NH-FITC) (23) was purified by dialysis using spectrapor membrane (cutoff 1000 Da) against DMSO in dark. The dialyzed product was dried under vacuum to obtain the conjugate (24). Purity of G4-PAMAM-O-Asp(CO-Dex)-(NH-FITC) (24) conjugate was confirmed by HPLC using florescent detector (Xex=495 nm/Xem=521 nm) (data not shown). Further, the appearance of aromatic protons at 6.57-6.62 (d, 6H, Ar), 6.63-6.70 (s, 3H, Ar) in $^1$H-NMR spectrum confirm the attachment of FITC and the integral ratio of amide protons of G4-PAMAM-O-Asp(CO-Dex)-NH$_2$ (20) appearing at 8.10-8.30 ppm to the aromatic protons at 6.57-6.62, 6.63-6.70 confirms the attachment of 6 molecules of FITC in G4-PAMAM-O-Asp(CO-Dex)-(NH-FITC) conjugate (24). The MALDI-TOF/MS of G4-PAMAM-O-Asp-(CO-Dex)-NH$_2$ (20) showed a mass of 21.9 kDa and a further increase in mass to 23.2 kDa affirmed the attachment of 6 molecules of FITC (data not shown).

Figure 7A:
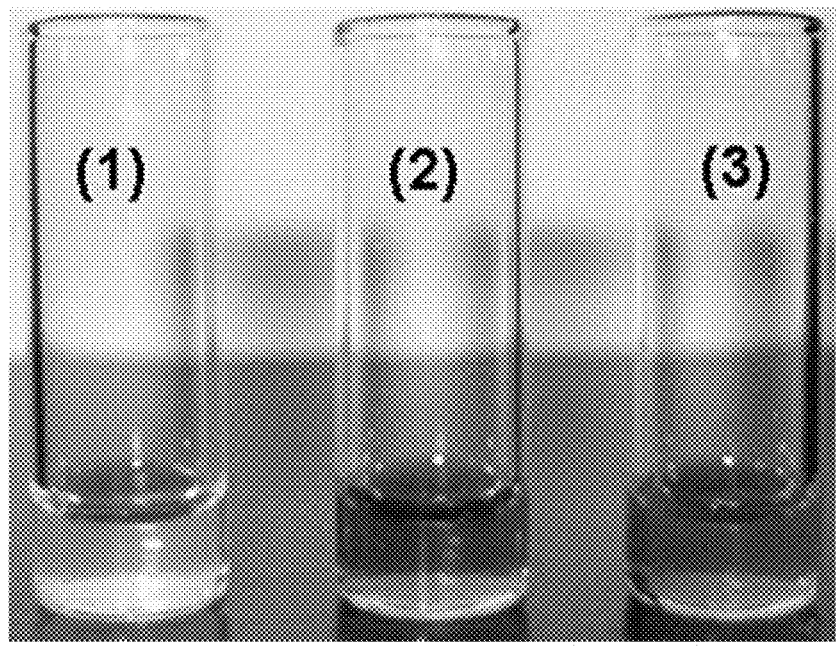
FIGS. 7A and 7B show the in-situ gel formation by crosslinking of G4-PAMAM-Asp-(CO-Dex)-NH$_2$ (20) with N-hydroxy-succinimide terminated PEG (PEG-NHS) (25). The gel (3) formed by reaction of 'NH$_2$' groups of G4-PAMAM-Asp-(COO-Dex)-NH$_2$ (20) with PEG-NHS (25) (colorless), while the 'COOH' groups are used for conjugating dexamethasone by ester linkage. The hydrogel (2) physically entrapping blue dextran is seen in blue color, while the hydrogel (3) formed by linking FITC to few NH$_2$ groups of G4-PAMAM-Asp (CO-Dex)-NH$_2$ (20) while the remaining NH$_2$ groups crosslink by formation of amide bond on reaction with PEG-NHS (yellow). The SEM image shows the gel network (in 200 μm) for the Dexamethasone conjugated (FIG. 7C) and FITC conjugated (FIG. 7D) dendrimer G4-PAMAM-Asp-(CO-Dex)-NH$_2$ crosslinked with PEG-NHS.
Figure 7B:
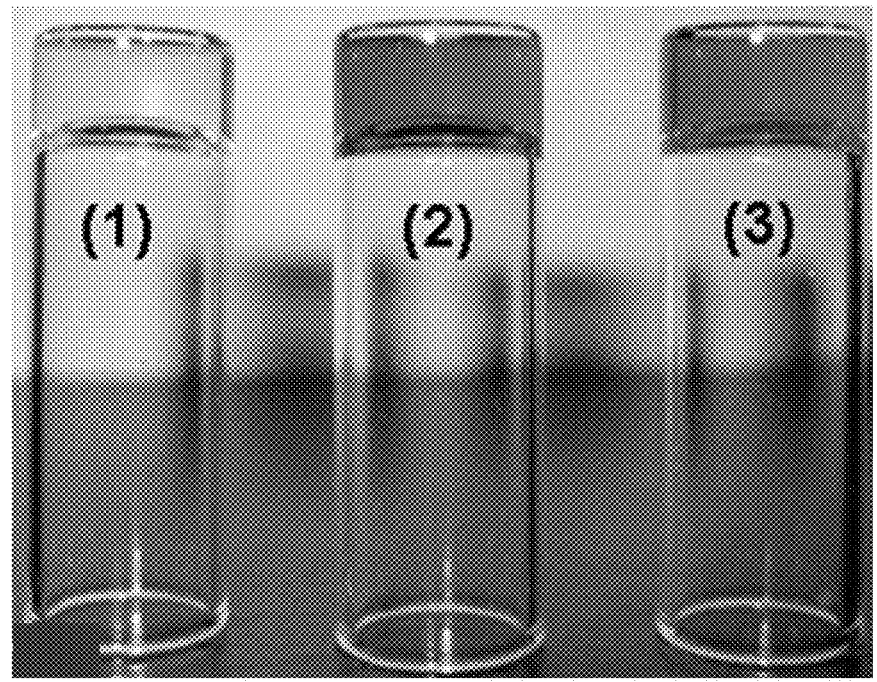
Figure 7C:
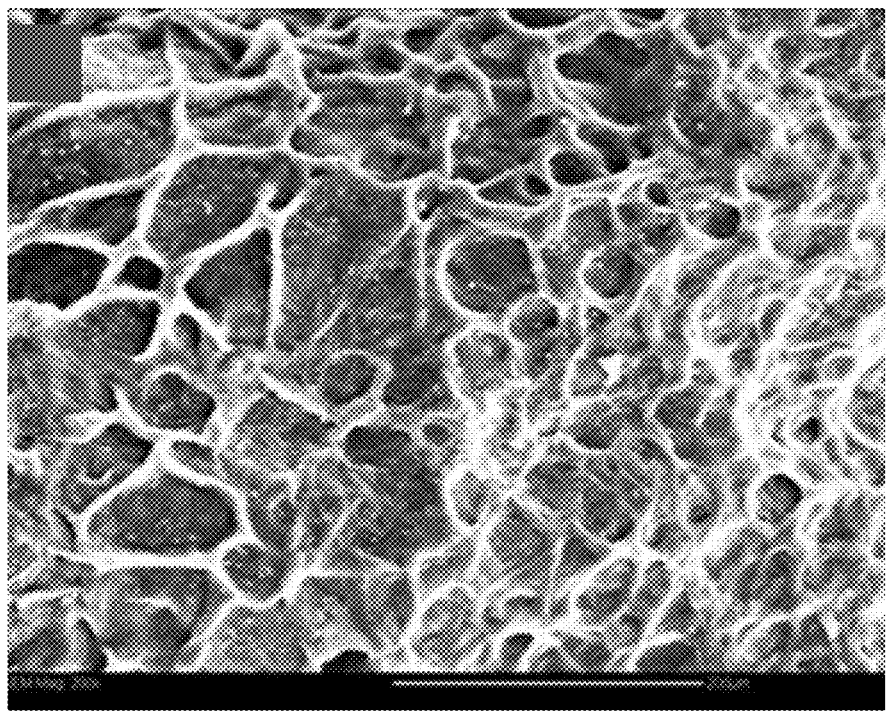
Figure 7D:
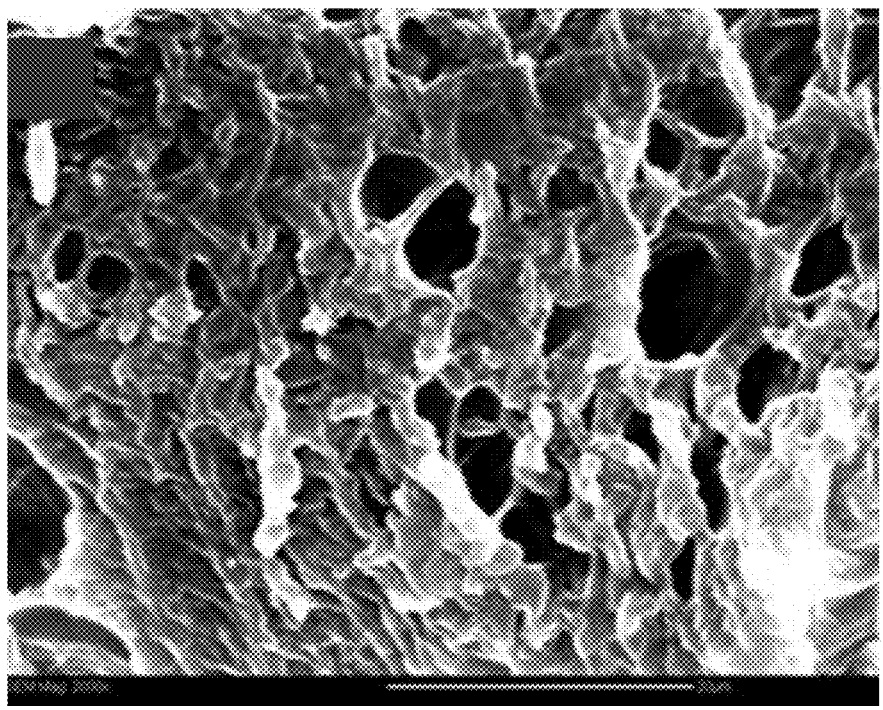

The presence of two functional handles led the inventors to develop in-situ forming hydrogels using only one of the functional handles for chemical reaction forming the gel, while the other handle can be used for conjugating the drugs (Scheme 6). The ability of the NH$_2$ groups of G$_4$-PAMAM-O-Asp-(CO-Dex)-NH$_2$ (20) for hydrogel formation was tested by its reaction with N-hydroxy-succinimide terminated 8-arm-PEG polymer (25) and blue dextran (Mw 5000) was physically entrapped in this gel. Hydrogel formation was determined by the "inverted tube method" and hydrogels were considered to have formed once the solution ceased to flow from the inverted tube (FIG. 7B). The gelation times for these hydrogels ranged 30-50 seconds and these open new vistas for the drug delivery application of these hereto-bifunctional dendrimers. Of the amine and the COOH terminal groups of G$_4$-PAMAM-O-Asp-(CO-Dex)-NH$_2$, (20) the COOH groups were involved in conjugation of drug dexamethasone (18) by ester linkage, while the NH$_2$ groups were involved in gel formation by amide linkages on reaction with N-hydroxy-succinimide terminated 8-arm-PEG (25) polymer (Scheme 6). This provides a new approach to design of hydrogels where the rate of drug release can be further slowed since the drug release involves two steps (i) release from covalent linkage of dendrimer after the degradation or hydrolysis of the bond (ii) diffusion of the drug from the hydrogel. Different concentrations of the polymer solution were tested in the stoichiometric ratio 1:1 and the gel formation was observed at 3, 5 and 8% w/w. Further, FITC (23) was attached to few NH$_2$ groups (3 end groups) of the G$_4$-PAMAM-O-Asp-(CO-Dex)-NH$_2$ (20) and this dendrimer also formed hydrogel by amide linkages on reaction with N-hydroxy-succinimide terminated 8-arm-PEG polymer (25), this gel is shown in FIGS. 7A and 7B. The SEM image shows the gel network formed by reaction of PEG-NHS (25) with G$_4$-PAMAM-O-Asp-(CO-Dex)-NH$_2$, (20; FIG. 7C) and G$_4$-PAMAM-O-Asp-(CO-Dex)-NH-FITC (24; FIG. 7D).

The above conjugation reactions show the ability of robust post-functionalization modifications in these heterobifunctional dendrimers, a hallmark of synthetic efficiency which further confirms that these peripheral end groups exhibit chemoselectivity based on their asymmetric or orthogonal nature. With these results there was demonstrated the ability to achieve a large number of asymmetric end groups (112) on G4 PAMAM dendrimer as compared to 64 symmetric end groups available traditionally, in just one step one pot reaction. Dexamethasone and indomethacin were conjugated to G4-PAMAM-O-Asp(COOH)-NHBoc (16) using an ester and after Boc deprotection amide linkage respectively. Further, FITC and dexamethasone were attached on G4-PAMAM-O-Asp(COOH)-NHBoc by thiourea and ester linkage respectively. The in-situ gelling hydrogels with the ability to physically entrap and covalently attach the drugs was demonstrated. The diverse nature of these hetero-bifunctional groups on dendrimers additionally confer the flexibility to append several functional groups in immediate succession, without the need for protection deprotection steps or need to append specific linker, all contributing the drastic reduction in the synthetic and purification steps.

In-Situ Hydrogel Formation by Crosslinking of Hetero-Bifunctional Dendrimers Bearing 'S-TP' and 'NH$_2$' Terminations Hydrogels have been used as vehicles for sustained drug delivery. The rich end functionalities prepared using the current approach could enable a new class of multifunctional hydrogels. There is disclosed herein an approach where a dendrimer based degradable hydrogel comprising redox sensitive bond is disclosed. The hydroxyl-terminated G4-PAMAM-OH dendrimer (12) was end capped with Boc-Cys(S-thiopyridyl)-OH (27) to yield 70% hetero-bifunctional end groups comprising 42 thiol protected and 42 amine terminations in protected form (Scheme-7). The thiol groups in Boc-cysteine were protected using 2-aldrithiol before modifying the dendrimer to yield G4-PAMAM-O—CO-Cys(S-thiopyridyl)-NHBoc (28). The thiol protection reaction was carried out in mild reaction conditions using methanol/water as solvent at room temperature for 24 hours. The product was obtained by recrystallization in acetone and hexane. The tert-Butoxycarbonyl (Boc) protecting groups were removed by using trifloroacetic acid in dichloromethane to yield amine functionality. G4-PAMAM-O—CO-Cys(S-thiopyridyl)-NH$_2$ (29) so obtained was mixed with the solution of 8arm-polyethylene glycol with thiol terminations (ratio 1:4 w/v respectively), resulting in in-situ forming hydrogel. This reaction is simple and occurs in physiological pH 7.4 phosphate buffer saline by the formation of disulfide crosslinks (Scheme-7). Apparently the disulfide crosslink reactions occur rapidly and hence the gelation time for these gels was less than 45 seconds. Over a period of time (20 days) physiological (pH 7.4, 37° C.) condition these gels undergo a gel to sol transformation suggesting the degradation or breakdown of the gels. It has been reported that disulfide exchange reactions occur slowly in milieu under physiological conditions which contribute for the degradation of the hydrogel. With these studies there is demonstrated the potential of these hetero-bifunctional dendrimers for in-situ forming hydrogels. These hydrogels can be further explored for physical encapsulation of drug or covalent linkage of drug to the other functional group for providing sustained release of drugs in a similar way as disclosed for the gels formed between G4-PAMAM-Asp-(CO-Dex)-$NH_2$ (20) with PEG-NHS (25). An interesting feature of this reaction is that both the tert-Butoxycarbonyl and thiopyridyl groups are orthogonal in nature and under the acidic conditions trifloroacetic acid in dichloromethane used for deprotection of tert-Butoxycarbonyl groups the thiopyridyl groups are extremely stable. With the introduction of two protecting groups in cysteine it was observed that the total number of copies of cysteine attached drastically reduced to 38 (59% conversion) as compared to other amino acids used without protecting groups or with single protecting group showing 87% to 91% conversion. The $^1$H-NMR, MALDI-TOF characterization of G4-PAMAM-O—CO-Cys(S-thiopyridyl)-NHBoc (28) and its tert-Butoxycarbonyl deprotection are provided in supporting information.

Example 2

Preparation of Dendrimer-PEG-Nanogel

Nanogel composed of the dendrimer-PDP (or dendrimer drug conjugate) and the PEG-SH (8 arm or liner) were synthesized. In brief, To a solution of 8-arm-PEG-SH (polymer) (100 mg) in PBS(1 ml) (pH=7.4) in $1^{st}$ 50 ml round bottom flask. Dendrimer-PDP (100 mg) in PBS (1 ml) (pH=7.4) in $2^{nd}$ 50 ml of round bottom flak. In $3^{rd}$ round bottom flask containing water phase(50 ml) consisted of a 2.5% (w/v) aqueous solution of the surfactant polyvinyl alcohol (PVA, MW 13,000-23,000, 87-89% hydrolyzed). The above $1^{st}$ polymer and $2^{nd}$ dendrimer-PDP was slowly added to the water phase with high-speed blending (24,000 rpm) for two minutes and the mixture formed a cloudy white emulsion. The emulsion was then allowed to stir in an uncovered beaker for several hours (24 hours) in a vacuum hood. The emulsion was centrifuged at 10,000 rpm for 30 minutes. The supernatant was lyophilized and stored for analysis of dendrimer-drug conjugate concentration to be determined by spectrophotometry. The white, nanoparticles were twice resuspended in deionized water following ten minute centrifugation at 10,000 rpm. They were finally resuspended in a minimal amount of deionized water and freeze-dried overnight. A fine white powder of dendrimer-PEG nanoparticles were then obtained and analyzed using scanning electron microscopy (SEM).

Example 3

Particle Size and Zeta Potential

The impact of surface modification of the dendrimers on particle size, zeta potential, blood retention and in vivo organ distribution has been previously reported. The complete surface modification of the dendrimers with amino acids on an average increased the particle size by 1-2 nm as seen from Table 3 (Particle size and zeta potential hetero-bifunctional dendrimers). The end capping of the cationic G4-PAMAM-$NH_2$ dendrimer with serine and cysteine resulted in drastic reduction in the zeta potential from +11.5 to −1.83 and 4.80 mV respectively. The interesting part is that both these constructs retain equal number of surface $NH_2$ termini as compared to unmodified G4-PAMAM-$NH_2$, yet exhibit reduced charge and are therefore expected to reduce the cytotoxicity. The hydroxyl terminated G4-PAMAM dendrimers are nontoxic due to the neutral surface charge and end capping it with aspartic acid and cysteine did not increase the charge significantly (Table 3). Again, both these constructs have $NH_2$ termini in addition to other groups yet exhibit low charge. By end capping of the hydroxyl terminated dendrimer, hydrogels can be attained and attachment of several functional groups, without eliciting the cytotoxicity. The unusual and unexpectedly high zeta potential was exhibited by the carboxylic acid terminated dendrimer end capped with serine (+8.83 mV). The increase in zeta potential was consistent with the increased cytotoxicity of this construct.

Example 4

Biocompatible Nature of the Components

Hemolytic and In-Vitro Cytotoxicity

Figure 8:
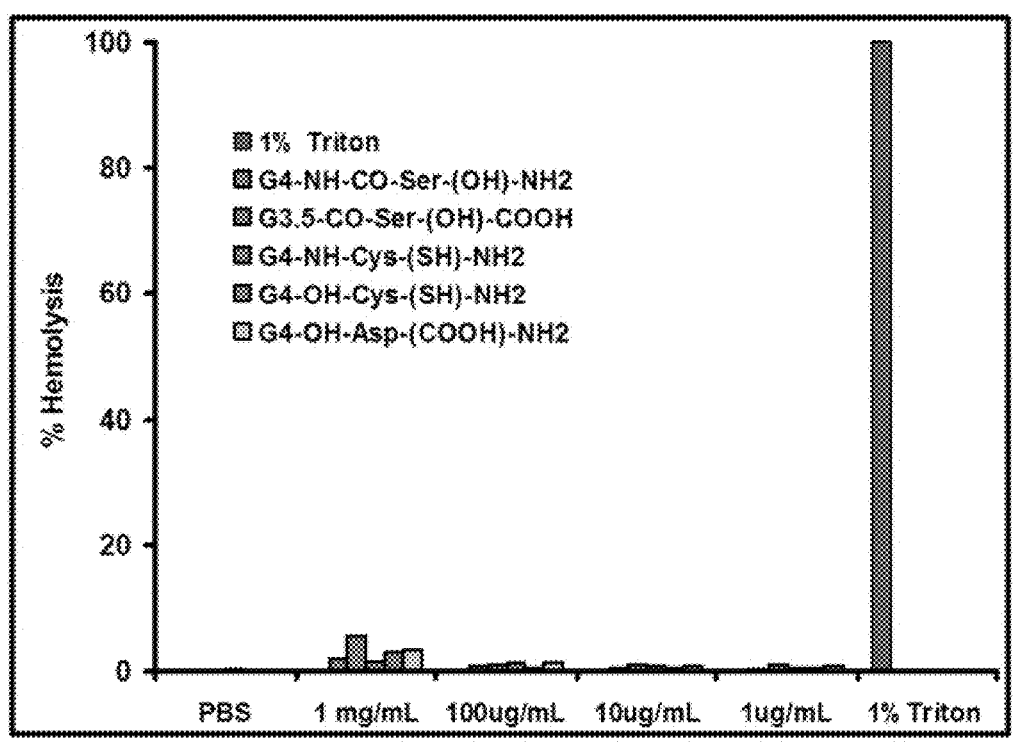
FIG. 8 shows the in-vitro hemolytic activity of new hetero-bifunctional dendrimers.

Red blood cell (RBC) lysis is a simple quantitative measure of hemoglobin (Hb) release widely used to study polymer-membrane interaction. Both cationic and anionic PAMAM dendrimers at 1 mg/ml concentration and exposure of 1 hour induce marked morphological changes evidenced by clumping of RBCs. The study showed a zero hemolysis and 100% hemolysis on incubating the RBCs with PBS (negative control) and 1% Triton X-100 (hemolytic agent-positive control) respectively. All the hetero-bifunctional dendrimers synthesized were non hemolytic in the concentration range 1-100 μg/ml on exposure for 3 hours (FIG. 8). At concentration of 1 mg/ml and exposure for 3 hours about 1.5%-3.0% was observed for all the compounds except the G3.5-PAMAM-CO-Ser(OH)—COOH which showed a hemolysis of 5% in 3 hours. Consistent with the hemolysis study, the in-vitro cytotoxicity study showed that the new compounds were nontoxic (FIG. 8) in the concentration range 10-100 μg/ml and few were nontoxic even at 1 mg/ml concentrations.

Dendrimer cytotoxicity is strongly influenced by the nature of surface group and dendrimers bearing $NH_2$ termini display concentration and generation dependant cytotoxicity. The amine-terminated dendrimers are known to exhibit cytotoxicity due to high cationic charge while the hydroxyl dendrimers are non-cytotoxic due to the neutral surface charge. The G4-PAMAM-$NH_2$ dendrimers exhibited cytotoxicity at 5 μg/ml concentration after 5 hours exposure to B16F10. The cell viability fell to <10% for the V79 chinese hamster lung fibroblasts cells after 24 hours exposure to PAMAM dendrimers generations G3 (1 nM), G5 (10 mM) and G7 (100 nM). A previous study showed that G4-PAMAM-OH and G3.5-PAMAM-COOH were nontoxic to A549 cells at concentrations 10-1000 μg/ml while G4-PAMAM-$NH_2$ dendrimer was nontoxic at 10-100 μg/ml and exhibited toxicity at 1000 μg/ml after 72 hours treatment. These results were consistent with those reported by Duncan et al.

Figure 9:
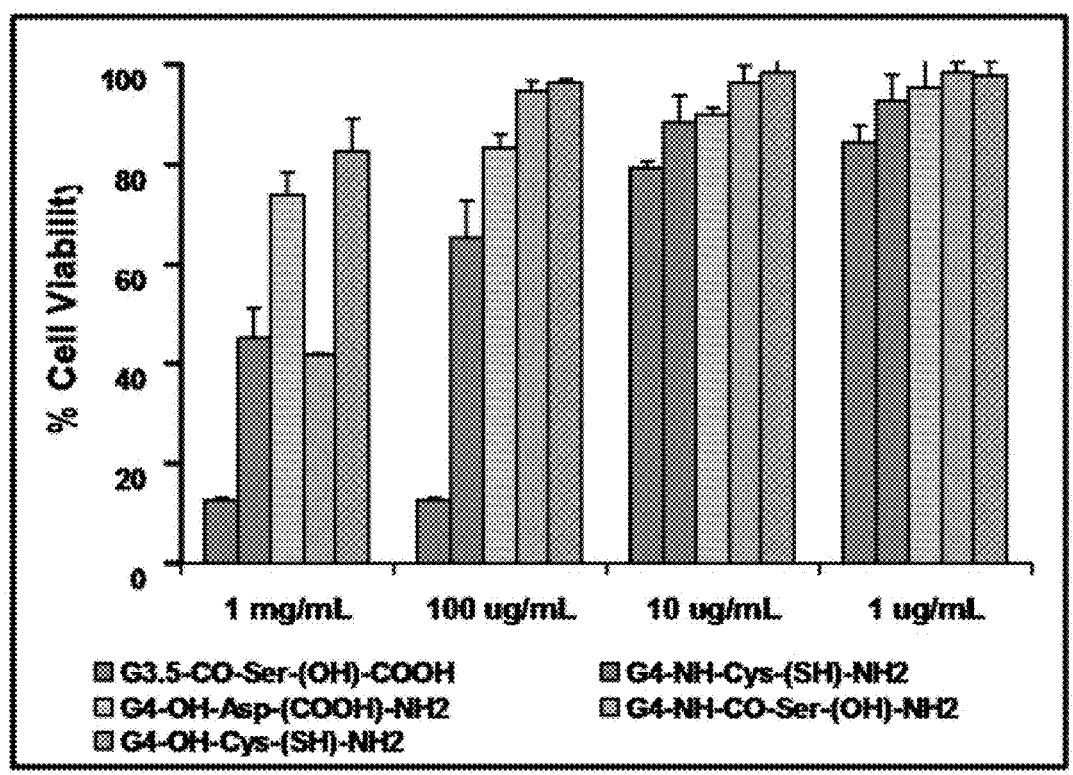
FIG. 9 shows the in vitro cytotoxicity of new bifunctional dendrimer in A549 cell.

The cytotoxicity of all the hetero-bifunctional dendrimers synthesized using human lung carcinoma cells (A549) and mouse microglial cells (BV-2) were evaluated, both cells with clinical implications for dendrimer use in cancer and neuroinflammatio. MTT assay showed that the compounds G4-OH-Cys-(SH)—NH$_2$ and G4-OH-Asp-(COOH)—NH$_2$ were not toxic to A549 cells in the concentration range of 1 µg/mL-1 mg/mL after 24 h exposure (FIG. 9). It is interesting to note that both these compounds have NH$_2$ termini and yet they were non-toxic at higher concentrations (in contrast to G4-PAMAM-NH$_2$ dendrimers with the same end groups) and retained the behavior similar to the neutral, non-toxic G4-PAMAM-OH dendrimers. This was consistent with the zeta potential measurements for both these compounds which showed that the zeta potential did not increase significantly from that of G4-PAMAM-OH (Table 3). While, modifying the surface of G4-PAMAM-NH$_2$ with serine and cysteine, the compounds; G4-PAMAM-NH-Ser(OH)—NH$_2$ and G4-PAMAM-NH-Cys(SH)—NH$_2$ were nontoxic at concentrations 1-100 µg/ml after 24 hours. Both the compounds had NH$_2$ termini after surface modification yet they were non-toxic at the concentrations evaluated. Further, more than 40% of cells were viable after exposure to high concentration of 1 mg/ml for 24 hours for these two compounds indicative of marked reduction in cytotoxicity when compared to G4-PAMAM-NH$_2$ alone. It has been reported that COOH terminated dendrimers G1.5 to 9.5 are nontoxic up to 5 mg/ml concentrations to B16F10, CCRF and HepG2. It was observed that on modifying G3.5-PAMAM-COOH with serine, the compound was nontoxic at 1-10 µg/ml concentration but exhibited marked toxicity at 100 µg/ml, and this can be expected since this compound exhibited a very high zeta potential +8.83 mV. From these results some promising candidates for drug delivery appear to be G4-OH-Cys-(SH)—NH$_2$ and G4-OH-Asp-(COOH)—NH$_2$ which showed post-functionalization ability, applicability in hydrogel formation and as carriers for multiple functional groups such as drug and imaging agents.

There was demonstrated that by appropriate choice of G4-PAMAM dendrimer end groups (NH$_2$, OH, COOH) and amino acids for surface modifications, a library of multivalent, multifunctional dendrimers bearing OH and NH$_2$, COOH and NH$_2$, NH$_2$ and SH, COOH and OH at the peripheries can be achieved. High yields were achieved in the coupling reactions since an excess of amino acid could be used, and the unreacted material could later be removed by a simple dialysis process. Conversions 70-90% of heterobifunctional dendrimers were obtained by carrying out the reactions in mild simplistic conditions such as water/dimethylsulfoxide/dimethyl formamide or in some cases dimethylsulfoxide/dimethyl formamide. The orthogonal peripheral handles of the resulting dendrimers are available for the eventual attachment of drugs, imaging agents or radiolabels and for the biological evaluation of these carriers.

One of the key features is the use of biocompatible amino acids used to achieve these diverse end functionalities. The objective was to use compounds that would not elicit undesirable interactions of dendrimers with cell surfaces, enzymes, and proteins in the blood serum. Further, the degree of drug loading could be easily adjusted. The amino acids are known to provide catalytic pockets for the enzymatic cleavage, hence the byproducts obtained by the cleavage of drug products are expected to be nontoxic. By decorating the dendrimer periphery with amino acid motifs, an enhanced solubility, reduced cytotoxicity, reduced hemolytic toxicity, while retaining the chemoselective reactivity and conferring flexibility to conjugate varied functional groups such as drugs and or imaging agents could be achieved.

Example 5

Local intravaginal drug therapy is preferred for treatment of ascending genital infections during pregnancy. There is disclosed herein an in-situ forming biodegradable hydrogel for sustained release of amoxicillin in the cervicovaginal region is described. Amino terminated, ethylenediamine-core generation-4 poly(amidoamine) dendrimer with 15 peripheralthiopyridyl groups (G4-NH$_2$—NHPPD) was crosslinked with 8-arm polyethylene glycol (PEG) bearing thiol terminations. The hydrogels were formulated and tested in-vivo in pregnant guinea pig model for volume, retention times, biodegradation, tolerability and transport across fetal membrane. The physicochemical characterization of the hydrogels was carried out using differential calorimetry, SEM, and confocal imaging. The hydrogels offer dual antibacterial activity arising from sustained release of amoxicillin followed by the release of amine terminated PAMAM dendrimer from the degrading gels. The in-vivo studies in guinea pig showed that 100-200 µL of gel sufficiently covered the cervicovaginal region with a residence time of at least 72 hours and gel was primarily retained in the maternal tissues without crossing the fetal membranes into the fetus. The dendrimer gels were stable up to 72 hours and the in-vivo biodegradation of gel occurred after 72 hours and this correlated well with the in-vitro degradation pattern. The pH of the vagina was not altered on application of the gel and none of the animals aborted up to 72 hours after application of gel. The histological evaluation of the cervical tissues showed absence of edema in epithelial cell layer, no sloughing of the epithelial or superficial mucous layer, absence of necrosis and infiltration of inflammatory cells in the submucosal layers confirmed that tissues were tolerant to the gel.

The immunohistofluorescence images showed the localization of the gel components on the superficial mucified epithelial layer. The crosslinking density and swelling of hydrogels was impacted by the polymer content and the 10% hydrogels exhibited highest crosslink density. The in-vitro drug release studies carried out using Franz diffusion cells showed that amoxicillin release from 6 and 10% gels was sustained for 240 hours as compared to 3% gels. As the polymer concentration increased to 10% the release pattern from gels approached diffusion controlled mechanism with diffusional exponent n=0.49. In conclusion, studied biodegradable in-situ forming hydrogels offer a therapeutic option to provide sustained localized delivery of amoxicillin intracervically to the pregnant woman for the treatment of ascending genital infections.

Herein, there was investigated the in-situ forming biodegradable hydrogels obtained by crosslinking of thiopyridyl functionalized G4-NH$_2$-PDP PAMAM dendrimer with 8-arm polyethylene glycol (20 kDa) for sustained intravaginal delivery of amoxicillin to treat ascending genital infections during pregnancy. Multiple thiopyridyl surface functionalities of the dendrimer and the star-PEG are utilized to create a biodegradable gel with disulfide linkages. This offers the potential for the dendrimer and drug to be released, as the hydrogel degrades. Further dendrimers offer the potential to target selectively inflammatory cells. The hydrogels were investigated for biodegradation, retention, tolerability and volume of distribution by intravaginal application in the pregnant guinea pig model. In the past hydrogels containing dendritic materials obtained by photocrosslinking, radiation, thermal gelation, ion interactions and freeze thaw cycles of polymers have been described. The hydrogels discussed herein are formed in-situ by chemical crosslinking resulting from simple mixing of the G4-NH$_2$—NHPDP dendrimer and the PEG polymer solutions in buffer through the formation of disulfide bonds and these hydrogels posses the properties of both the PEG hydrogels and the dendrimer.

The cervical infections in pregnant women caused by pathogens such as *Streptococcus* group B, *E. coli* and *Gardnerella vaginalis* are responsible for the premature rupture of the fetal membranes, chorioamnionitis and prematurity. Amine terminated PAMAM dendrimers exhibit antibacterial activity against *E. coli*, *P. aeruginosa* and *S. aureus* by inducing formation of nanoscale holes in lipid bilayers of bacterial cell membrane causing cell lysis and death. The partially pegylated amine terminated PAMAM dendrimers demonstrate antibacterial activity against *E. Coli* bacteria, *P. aeruginosa*. The pegylation of dendrimers reduces their cytotoxicity and yet retains the antibacterial activity. The poly(amidoamine) generation 4 amine terminated PAMAM dendrimer has been partially modified with thiopyridine moieties and chemically bound to 8arm PEG via disulfide bridges to form the hydrogel while number of the primary amine groups remained unmodified. The covalent linking of PEG to dendrimer while gel formation was expected to overcome the cytotoxicity. Further, the investigated amoxicillin loaded hydrogels were expected to exhibit dual antibacterial mechanism, arising from sustained release of the antibiotic and activity exhibited by the amine terminated dendrimer released from the degrading gel.

Materials and Methods

Materials

Amine terminated, ethylenediamine-core poly(amidoamine) dendrimer (G4-NH$_2$) (diagnostic grade generation-4 with —NH$_2$ groups) was purchased from Dendritech and 8-arm-PEG-SH (20 kDa) (5) was purchased from NOF America Corporation, USA. Other reagents were obtained from assorted vendors in the highest quality available. Of these, amoxicillin, N-Succinimidyl 3-(2-pyridylthio)-propionate (SPDP), polyvinylpyrrolidone (PVP 30 kDa), PEG 600, glycerol, glutathione (GSH), dimethyl sulfoxide (DMSO), fluorescein isothiocyanate (FITC), dimethylformamide (DMF), Ethanol, phosphate buffer saline (PBS, pH, 7.4), and HPLC-grade solvents were obtained from Sigma-Aldrich.

Synthesis of G4-NH$_2$—NHPDP (4)

G4-NH$_2$ (2) dendrimer was dissolved in PBS buffer pH 7.4 (20 mL) and the solution of SPDP (3) in ethanol (10 mL) was added to it under stirring to provide sufficient modification whilst preventing loss of product due to the insolubility of highly modified dendrimer. Reaction was stirred at room temperature for 2 hours. After completion of the reaction, solvent was removed under reduced pressure to get a solid compound. The crude product obtained from the reaction mixture was dialyzed against water using spectrapor dialysis membranes (MW cut-off 1000 Da) (pH=5 obtained by addition of 1% HCl) to remove by-products and the excess of reactants. After dialysis, the solvent was removed using lyophilization. Solid was reconstituted in desired amount of PBS (pH 7.4) and used for hydrogel formulation.

Preparation of -G4-NH$_2$-FITC-NHPDP

FITC (0.082 g M=389.38 $2.10 \times 10^{-4}$ mol) was added to the solution of G4-NH$_2$ dendrimer in DMSO (20 mL) under stirring and the reaction was continued in dark for 18 hours. To remove unreacted FITC, the reaction mixture was dialyzed (molecular weight cut off of membrane 1000 Da) in DMSO for 24 hours (solvent was changed every 8 hours). After dialysis the DMSO was lyophilized to get pure G4-NH$_2$-FITC conjugate as dark orange color solid. The G4-NH$_2$-FITC conjugate was dissolved in methanol and precipitated in acetone. Absence of free FITC in the conjugate was verified by TLC using chloroform and methanol (ratio 1:1) as mobile phase. After purification of the G4-NH$_2$-FITC conjugate, the above described procedure was used to synthesize -G4-NH$_2$-NHPDP-FITC for hydrogel formulation for in vivo applications Hydrogel Formation Hydrogels were prepared by crosslinking of the branched thiol terminated PEG polymer (8-arm-PEG-SH, 20 kDa) with G4-NH$_2$—NHPDP (or G4NH$_2$FITC-NHPDP). Hydrogels containing 10, 6 and 3% w/v of polymers were prepared by mixing equal volumes (1:1 v/v, 100 µL each) of the 10, 6 and 3% w/v polymer solutions of G4-NH$_2$—NH-PDP and 8-arm-PEG-SH in PBS (pH=7.4) as shown in Table 4. The ratio of PDP to thiol functionalities in these hydrogels was 2:1. The hydrogels resulted in 10-30 seconds of mixing the two polymer solutions. The gelation time was determined by the vial tilting method. When the sample showed no flow, it was regarded as a gel. These hydrogels were further investigated to determine the degree of swelling, drug loading efficiency, in vitro release studies, and in vivo applications.

Morphology of the Hydrogel

Scanning Electron Microscopy (SEM) analyses were performed to investigate the morphology of hydrogel. The 10, 6 and 3% w/v hydrogels were prepared for electron microscopy at room temperature, followed by dehydration using lyophilization. It was observed that the hydrogel volume was reduced by ~75% during the dehydration process. The samples were critical point dried, sputter-coated with 9 nm of gold/palladium, and imaged using SEM (HITACHI S-2400 Scanning Electron Microscope) at 20 kV. The cross sections of the hydrogels were observed using confocal microscopy, to determine the crosslink density. The gels were formed by crosslinking of -G4-NH$_2$-FITC NHPDP with 8-arm-PEG-SH in PBS (pH=7.4). The 10, 6 and 3% w/v gels were embedded in OCT media (Tissue-Tek®) and frozen at −80° C. until they were sectioned. Gels sections (20µ thick) were cut using a cryostat (Leica Microsystems; Nuchloss, Germany). Images of the sectioned gels were captured on a Leica TCS SP5 laser scanning confocal microscope (Leica Microsystems GmbH, Wetzlar, Germany).

Equilibrium Swelling of Hydrogels

The 10, 6 and 3% w/v hydrogel discs were obtained by crosslinking of G4-NH$_2$—NH-PDP and PEG (1:1 v/v, 100 µL each) in a cylindrical glass vial (12×35 mm). These hydrogel discs were weighed and subsequently immersed in 5 mL of pH 7.4 phosphate buffered saline (PBS) solution at 37° C. in 30 mL scintillation vials. The swollen hydrogels were removed from PBS and weighted at various time intervals until a swelling equilibrium had been reached. All experiments were carried out in triplicate and the results are expressed as means±standard deviations.

The degree of swelling was calculated from the formula previously reported where $W_s$ is the weight of the swollen hydrogel at time t and $W_0$ (wet) is the initial weight.

$$\% \text{ Swelling} = \frac{(W_s - W_o)}{W_o} \times 100$$

Formulation of Hydrogel

The prototype vaginal gels were made using excipients; glycerin (5%, v/v), PVP (4%, w/w) and PEG 600 (5%, v/v), which were included in hydrogel formulation to improve the emollient, adhesion, retention and spreadability properties of hydrogels. These excipients were dissolved in the PBS buffer at the concentrations as shown in Table 4 and this solution was used as a vehicle to dissolve separately the G4-NH$_2$—NHPDP (or G4-NH$_2$-FITC-NHPDP) and 8-arm PEG-SH. The hydrogel formulation was obtained by mixing the solution of G4-NH$_2$—NHPDP and 8-arm PEG-SH in the solvent vehicle at the ratio 1:1 v/v. The gelling time was recorded for the different compositions of vehicle and polymers. The optimal concentration of additives was determined by measuring the crosslinking time and retention time of hydrogel formulation on targeted area.

Reverse Phase HPLC Characterization

In vitro drug release and characterization of conjugates was carried out with waters HPLC instrument equipped with one pump, an auto sampler and dual UV, RI, and fluorescence detector interfaced to millennium software instruments molds should included. The mobile phase used was acetonitrile (both 0.14% TFA by w.) and water phase had a pH of 2.25. Mobile phases were freshly prepared, filtered and degassed prior to the use. Supelco Discovery BIO Wide Pore C5 HPLC Column (5 μm particle size, 25 cm×4.6 mm length×I.D.) equipped with C5 Supelguard Cartridge (5 μm particle size, 2 cm×4.0 mm length×I.D.) was used for characterization of the conjugates as well as in vitro drug release studies. Gradient method was used for analysis and the method used was water: acetonitrile (100:0) to water-acetonitrile (60:40) in 25 minutes followed by returning to initial conditions for 5 minutes. The flow rate was 1 mL/min. Calibration curves were prepared for amoxicillin, based on UV absorbance peak area at 229 nm. These calibrations were used to measure of in vitro drug release from cellulose membrane in Franz diffusion cell.

Differential Scanning Calorimetry (DSC) Analysis of Hydrogels

The neat and modified polymers and hydrogels were subjected to thermal analysis using TA Instruments DSC Q2000 V24.4 Build 116 Module DSC Standard Cell RC. The experiments were conducted in crimped sealed aluminium pans and the weight of each sample was in the range 1-2 mg. All the samples were analyzed using the heat cool heat cycles. The samples were equilibrated at –50° C. for 2 minutes and were heated to 150° C. at a heating rate of 5° C./min under nitrogen flow. The samples were quench cooled to –50° C. and equilibrated for 2 minutes and again heated to 150° C. at a heating rate of 5° C./min.

Degradation of Hydrogels

In vitro degradation of hydrogel was performed in glutathione (GSH) solutions at pH 4 and simulated vaginal fluid up to 72 hours. The simulated vaginal fluid (SVF) was prepared as described previously by addition of GSH. Briefly, the SVF was prepared by 350 mg of NaCl, 140 mg of KOH, 22 mg of Ca(OH)2, 18 mg of bovine serum albumin, 200 mg of lactic acid, 100 mg of acetic acid, 16 mg of glycerol, 40 mg of urea, 500 mg of glucose, 20 mg of GSH and the pH was adjusted to 4±0.02 using 0.1 M HCl. Hydrogel discs obtained by crosslinking of G4-NH$_2$—NHPDP and 8-arm PEG-SH (1:1 v/v, 100 each) were immersed into the 5 mL GSH solution at pH 4 and simulated vaginal fluid at pH 4 in 30 mL scintillation vials in triplicate and observed for degradation.

Drug Loading into the Hydrogels

Antibiotic (amoxicillin) was physically entrapped into the hydrogels. The drug was (0.5 mg) added to the PEG solution (100 μL) in vehicle and the solution of G4-NH$_2$-NHPDP (100 μL) in vehicle was added to this PEG solution to form the dendrimer-PEG hydrogel (200 μL).

DRUG loading efficiency

The amount of amoxicillin entrapped in the dendrimer-PEG hydrogels (10%, 6% and 3%) was determined by breaking the gel into small pieces and transferring into 1 mL eppendorf tube filled with PBS (pH 7.4) and sonicated for 10 minutes and washed the hydrogel pieces three times to extract drug. The washings were collected and filtered with 0.2 μm millipore filter and quantified by a reverse phase (RP) HPLC analysis, using UV detection at a wavelength of 229 nm. Water: acetonitrile were used as mobile phase at a flow rate of 1 mL/min. The difference between the amount of drug taken initially and the drug content in the washings is the amount of drug entrapped.

In Vitro Drug Release Using Franz Diffusion Cell

For the in-vitro drug release study, jacketed Franz diffusion cells with flat ground joint were used. The membrane was clamped between the donor and receiver chambers of the Franz diffusion cell apparatus with a diameter of 5 mm and a diffusional area of 0.64 cm$^2$ and the receptor chamber volume of 5 mL. Nitrocellulose acetate membranes (Millipore, America) with an average pore size of 0.45 μm were used. The receptor chambers filled with PBS (pH=7.4) were maintained at 37° C. in order to ensure the body temperature. Drug (Amoxicillin) is well soluble in the chosen receptor medium. Each cell contained a magnetic bar and was stirred (600 rpm) during the experiment. The cells were equilibrated for 1 hour before the samples were mounted. 200 μL samples were taken at predetermined time points and replaced with equal amount of fresh receptor medium to maintain sink condition. The samples were kept frozen at 4° C. prior to analysis, to quantify the drug release by reverse phase high performance liquid chromatography (RP-HPLC). All samples were run in triplicates for statistical analysis.

Evaluation of Hydrogel in Pregnant Guinea Pig Model

Pregnant Dunkin-Hartley strain guinea pigs (n=15) (Charles River) at 55 days of gestation (third trimester) were anesthetized by inhalation of 5.0% Isoflurane in 100° A) oxygen at a flow rate of 2 L/min in an approved rodent anesthesia chamber. Surgical-level of anesthesia was maintained with 1.5 and 2.0% Isoflurane in 100% oxygen at a flow rate of 1-2 L/min via a nose cone. An endoscope was used to visualize the cervix. FITC labeled dendrimer-PEG hydrogel (100-500 μL) was injected into the cervix using i.v. catheter (BD Angiocath, Infusion, Therapy systems Inc. Sandy Utah, 16 GA 5.25 IN, 1.7×133 mm). The pH of the vagina was intermittently tested by wiping the vaginal fluid using cotton swabs. After single vaginal application, the vaginal cavity was observed for any signs of possible irritation of the vaginal mucosa (edema or redness of tissue). The observations were scored and recorded as follows: no erythema, slight erythema (light pink) and moderate to severe erythema (dark pink or light red). After 5, 12, 24 and 72 hours intervention, guinea pigs were euthanized with pentobarbital sodium (120 mg/kg) and midline laparotomy was performed to expose cervicovaginal region for further evaluation. The retention times, biodegradation and tolerability were studied in-vivo using the guinea pigs. The vaginal and cervical tissues were used for histopathological evaluation.

Immunofluorescence Histochemistry

An immunofluorescence studies were performed to investigate biodistribution of the FITC-dendrimer-PEG hydrogel in the cervicovaginal tissues of guinea pig after 24 and 72 hours of treatment. Double immunofluorescent staining was performed on 20 μm thick, paraffin sections of tissues placed on silanized slides. The mucified epithelial cells were identified based on the positive staining for cytokeratin. The immunoflurorescent staining was performed using Ventana Discovery autostainer for controlled and optimised reaction environment using the automation-optimized reagents from Ventana Medical Systems Inc. Briefly, paraffin wax sections were loaded onto the Ventana Discovery platform and following steps were completed automatically, these included dewaxing by EZ prep buffer (Ventana Medical Inc.), pretreatment in Tris/EDTA pH 8.0 antigen retrieval solution (Ventana mCC1) or protease solution for 1 hour (Ventana protease 2). Endogenous peroxidase was inactivated using an enhanced inhibitor provided in the staining kit and nonspecific antibody binding was blocked by treatment with blocking solution for 10 minutes. The blocking solution was removed and the sections were washed three times with PBS/Tween solution incubated with primary antibodies for 1 hour using the liquid cover slip (Ventana Medical Inc). The primary antibody used was monoclonal mouse anti-human cytokeratin (1:200, M7018, Dako Carpinteria, Calif., USA). The sections were again washed three times with PBS/Tween solution incubated with secondary antibodies, Alexa Fluor® 594 goat anti-mouse IgG (1: 500, A11005, Invitrogen) for 1 hour using the antibody diluent from Ventana. The sections were washed with PBS/Tween, counterstained and mounted with DAPI prolong Gold antifade and cover slipped. Images were captured from Leica TCS SP5 Laser Scanning Confocal Microscope (Leica Microsystems GmbH, Wetzlar, Germany). All study specimens were analyzed by a pathologist blinded to the clinical information.

Results and Discussion

Synthesis of G4-NH$_2$—NHPDP

To incorporate the thiol reactive terminal groups on the dendrimer to form hydrogel with 8-arm PEG-SH, the SPDP linkers were covalently attached to the dendrimer surface to yield thiopyridine functionalities. It was achieved by reacting amine terminated generation 4 PAMAM dendrimer (for short G4-NH$_2$) with the heterobifunctional cross-linker SPDP (Scheme 15). The N-succinimidyl activated ester groups of SPDP were coupled to the terminal primary amines to form amide-linked 2-pyridyldithiopropanoyl (PDP) groups (G4-NH$_2$—NHPDP) (Scheme 15). The $^1$H NMR spectra of G4-NH$_2$—NHPDP showed presence of protons corresponding to the aromatic ring of thiopyridyl groups and protons related the dendrimer. The aromatic protons of thiopyridine emerged at 7.20-2.26 (m, 1H, Ar), 7.74-7.82 (br. d, 1H, Ar), and 8.15-8.22 (m, 2H, Ar) ppm while the other protons appeared at 2.42-2.50 (m, 4H, —CH$_2$—CH$_2$—).

Figure 10:
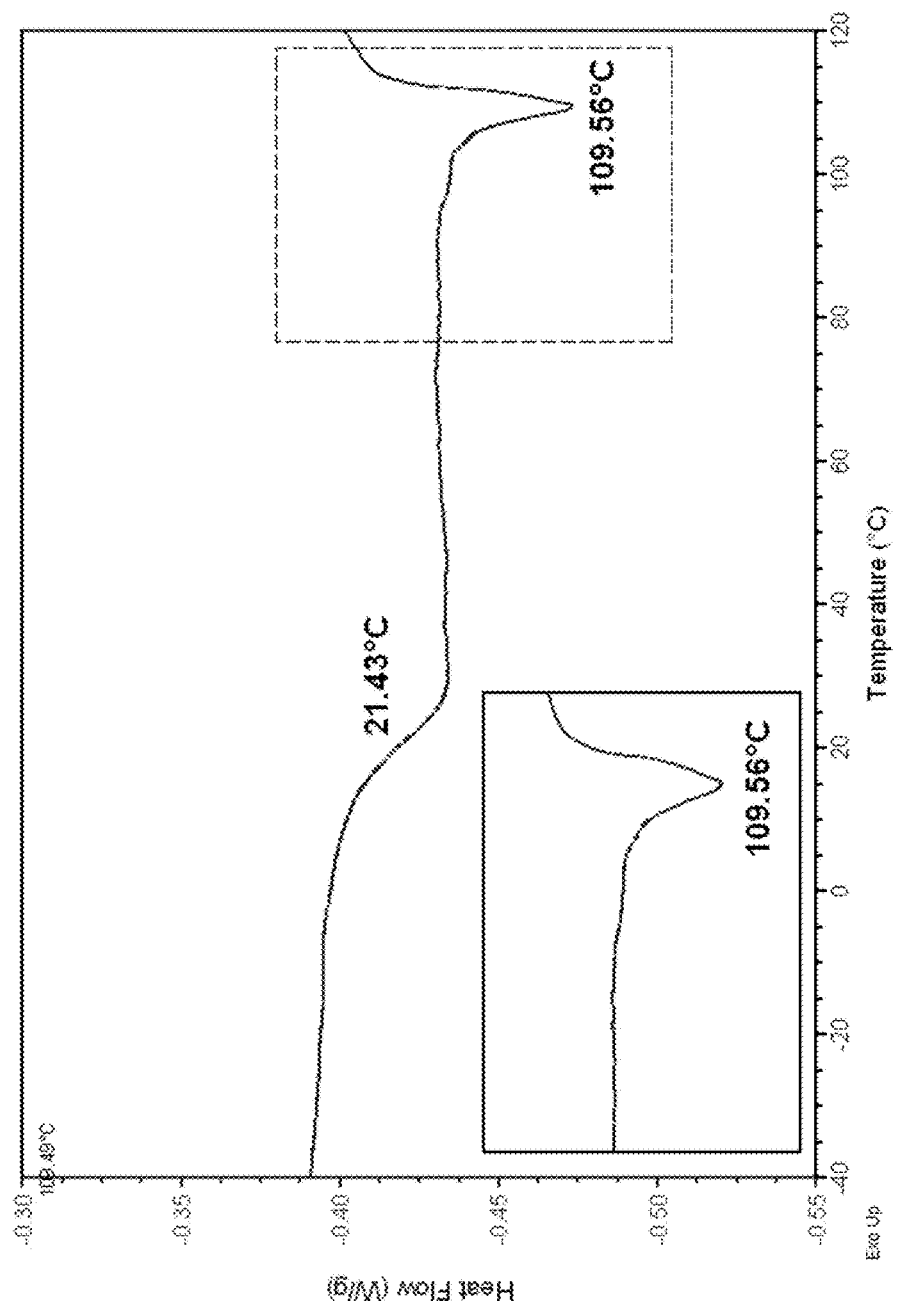
FIG. 10 is a DSC thermogram of G4-NH-PDP that shows the $T_g$ at 21.4° C. and an endotherm at 109.6° C. The increase in $T_g$ to 21.4° C. from −28° C. is indicative of the addition of PDP groups on to the dendrimer.

Scheme 15 is a schematic representation of the hydrogel formation. The thiol terminated 8-arm PEG (20 kDa) formed gel at pH 7.4 by reacting with the dithiopyridine terminal groups of the G4-NH$_2$—NHPDP resulting in disulfide linkages from PDP, 2.67-2.72 (m, 2H, —CH$_2$— from interior dendrimer) 2.86-2.92 (m, 1H, —CH$_2$— from interior dendrimer), 3.03-3.12 (m, 1H, —CH$_2$— from interior dendrimers) 8.38-8.45 (br. d, 1H, NH, from interior amide protons), and 8.52-8.59 (br. d, 1H, NH, from interior amide protons) ppm as seen in the $^1$H NMR spectra of G4-NH$_2$—NHPDP. Data indicates the presence of thiopyridine (PDP) groups in the G4-NH$_2$—NHPDP dendrimer. These results are consistent with $^{13}$C NMR data, further affirmed by DSC analysis of the G4-NH-PDP. The G4-NH$_2$ dendrimer showed a T$_g$ at −28° C., which is in good agreement with previously reported values. G4-NH$_2$—NH-PDP exhibited T$_g$ at 21.4° C. and an endotherm at 109.6° C. (FIG. 10). The difference in the T$_g$ values between G4-NH$_2$ and G4-NH$_2$—NH-PDP can be attributed to the PDP groups covalently bound to the dendrimer. The endotherm observed in case of G4-NH$_2$—NH-PDP conjugate further confirms successful modification of dendrimer with PDP functionalities, which is consistent with previous reported results. The G4-NH$_2$-NHPDP conjugate equipped with PDP crosslinkers was used to fabricate dendrimer-PEG hydrogel with 8-arm-PEG-SH (G4-NH$_2$—NHPDP-SSPEG). The partial modification of primary amines of G4-NH$_2$ dendrimer resulting in formation of G4-NH$_2$—NH-PDP was carried out to enable the linking of PEG chains to the dendrimer by formation of disulfide bonds.

FIG. 10 shows the DSC thermogram of G4-NH$_2$—NH-PDP shows the T$_g$ at 21.4° C. and an endotherm at 109.6° C. The increase in T$_g$ to 21.4° C. from −28° C. indicates modification of dendrimer with PDP groups.

Hydrogel Formation

Figure 11:
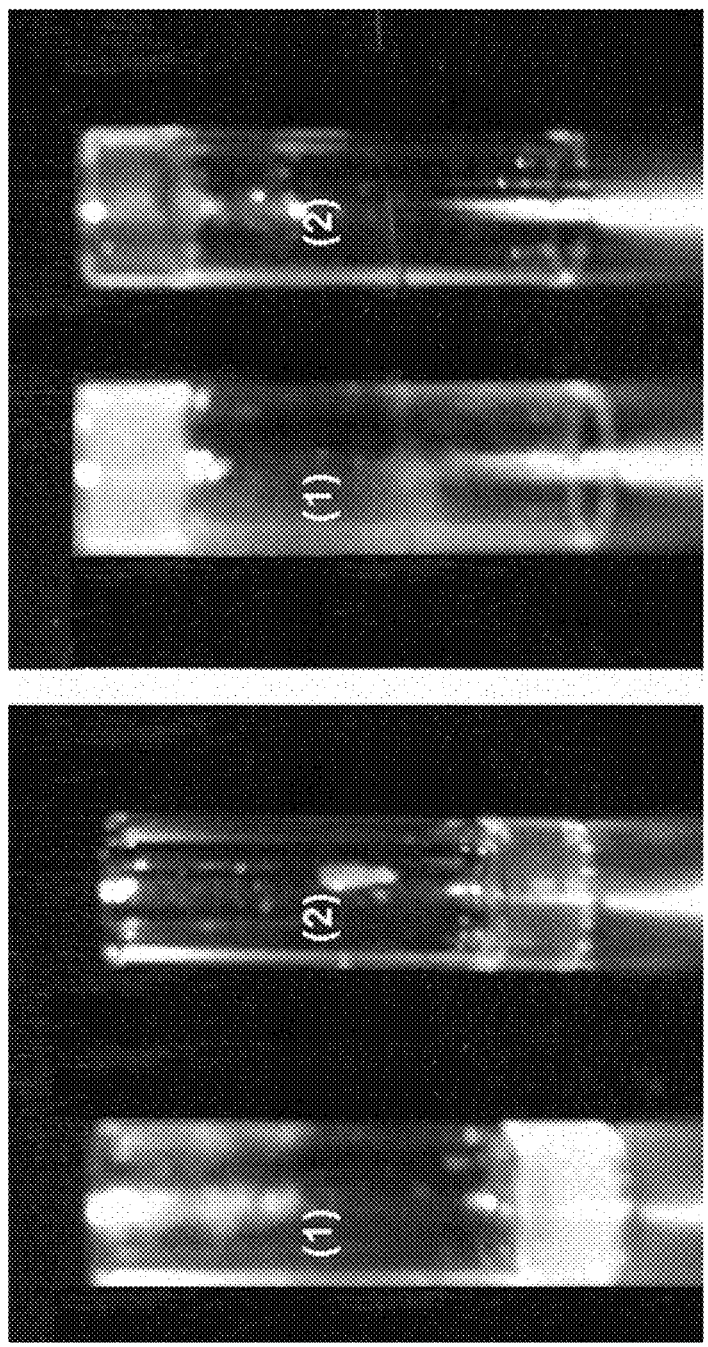
FIG. 11 show the in-situ forming hydrogel by crosslinking of G4-NH-PDP with 8-arm-PEG-SH. The gel formed by reaction of 'PDP' groups of G4-NH-PDP (5) with 8-arm-PEG-SH. The hydrogel (1) physically entrapping blue dextran is seen in (2).

In-situ forming hydrogels with disulfide crosslinks were investigated for intravaginal amoxicillin delivery. These hydrogels were designed for local delivery of antibacterial agents to treat the ascending genital infections. Hydrogels composed of 3, 6 and 10% w/v of the polymers were formed by mixing the solutions of G4-NH$_2$—NH-PDP and 8-arm PEG-SH, resulting in covalent disulfide crosslinks arising from the interaction of thiol groups of the PEG-SH with the thiopyridine functionalities present on the dendrimer surface (G4-NH$_2$—NH-PDP) (Table 4). The hydrogel results from intermolecular crosslinking as shown in Scheme 15. For the formation of hydrogels, the crosslinking agent (G4-NH$_2$—NH-PDP) was used in an excess of molar ratio (in terms of the functional groups) relative to PEG-SH (Table 4). The hydrogels were formed in 10-30 seconds of mixing the dendrimer conjugate and PEG-SH solutions as seen from the inverted tube method, and obtained gels were not pourable (FIG. 11). Higher polymers concentration resulted in increase of the rate of gel formation FIG. 11 shows the in-situ forming hydrogel by crosslinking of G4-NH$_2$—NH-PDP with 8-arm-PEG-SH. The gel was formed by reaction of 'PDP' groups of G4-NH$_2$—NH-PDP with 8-arm-PEG-SH (1) and (2) hydrogel (1) physically entrapping blue dextran. (Table 4). The rapid formation of hydrogels with the increased concentration of polymers might be due to rapid creation of intense crosslinking networks, reducing the time for gelation. For example 10% hydrogel formed in 10 seconds, while formation of 3% hydrogel takes 30 seconds. Hydrogels appeared to be transparent, with uniform surface. The hydrogels were designed to facilitate linking of PEG-SH chains to the partially modified G4-NH$_2$—NH-PDP dendrimer. The linking of PEG chains by disulfide bonds was expected to eliminate cytotoxicity of the primary amine terminated dendrimer. Pegylated dendrimers have been shown to be biocompatible Table 4 shows hydrogel compositions and stoichiometric ratio between thiopyridine and thiol groups

| % of Hydrogel | Hydrogel volume | Weight of polymer and ratio (1:1) | Stoichiometric ratio of thiopyridine groups to thiol groups | Gelation Time (s) | Total Polymer content |
|---|---|---|---|---|---|
| 3% | 200 µL | G4-NH$_2$-NHPDP(3 mg) + PEG-SH(3 mg) (1:1) | (2:1) | 30 | 3% |

| % of Hydrogel | Hydrogel volume | Weight of polymer and ratio (1:1) | Stoichiometric ratio of thiopyridine groups to thiol groups | Gelation Time (s) | Total Polymer content |
|---|---|---|---|---|---|
| 6% | 200 μL | G4-NH$_2$-NH-PDP(3 mg) + PEG-SH(3 mg) (1:1) | (2:1) | 20 | 6% |
| 10% | 200 μL | G4-NH$_2$-NH-PDP(3 mg) + PEG-SH(3 mg) (1:1) | (2:1) | 10 | 10% | and the in-vivo studies, discussed herein, show that the gels were well tolerable without any toxic effects.

Morphology of the Hydrogel

Scanning electron microscopy (SEM) experiments were performed to study the surface morphology of dendrimer-PEG hydrogel (FIG. 12). SEM micrographs of critical point dried gels show a uniform dense structure with striations. The SEM experiments were performed on a dehydrated sample that exhibited significant reduction in volume compared to the hydrated state. It is likely that the water hydrated dendrimer-PEG hydrogel adopts a dense structure with regular cross linking network throughout the gel. The cross section of the hydrogels was investigated by crosslinking the G4-NH$_2$-FITC-NHPDP and 8-arm PEG-SH. The cross section observed under the confocal microscopy shows an isotropic hydrogel that exhibits a classic uniform morphology with pores seen in FIG. 13. A characteristic change in morphology based on changes in polymer content in the hydrogel was observed (FIG. 13). The 3% hydrogel does not form a dense crosslinked network as seen for the 6 and 10% gels. By introducing the different concentration PEG and dendrimer in the hydrogels, the porosity of the network changed, pore size is gradually decreased by increasing the concentration of polymer. These results suggest that dehydration of gels for SEM leads to artifact in the highly water-saturated gels, their morphology can be better viewed by cryo-sectioning the gels with the presence of fluorescein isothiocynate (FITC).

Figure 12A:
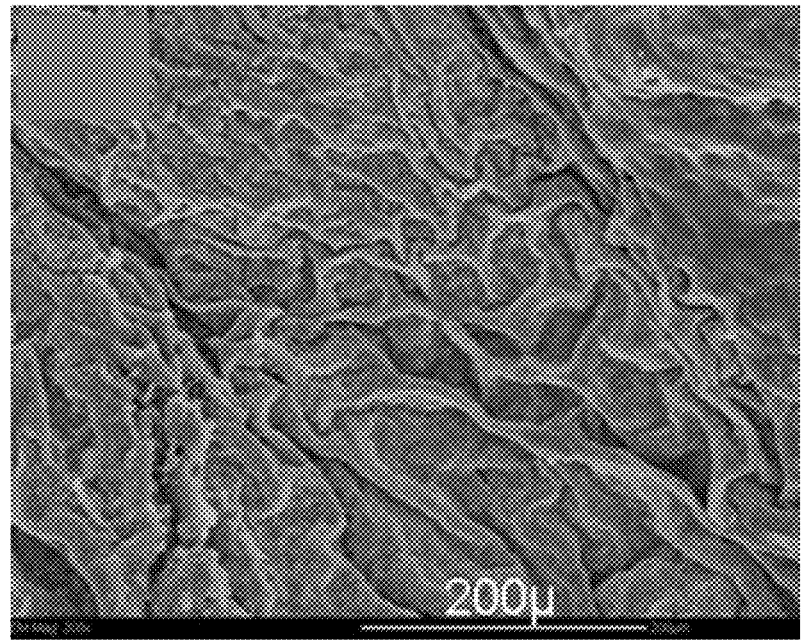
FIGS. 12A-C show the SEM images of dendrimer G4-NH-PDP crosslinked with 8-PEG-SH gel. These gels were dehydrated by lyophilization. 200 μm (FIG. 12A), 50 μm (FIG. 12B), 20 μm (FIG. 12C).
Figure 12B:
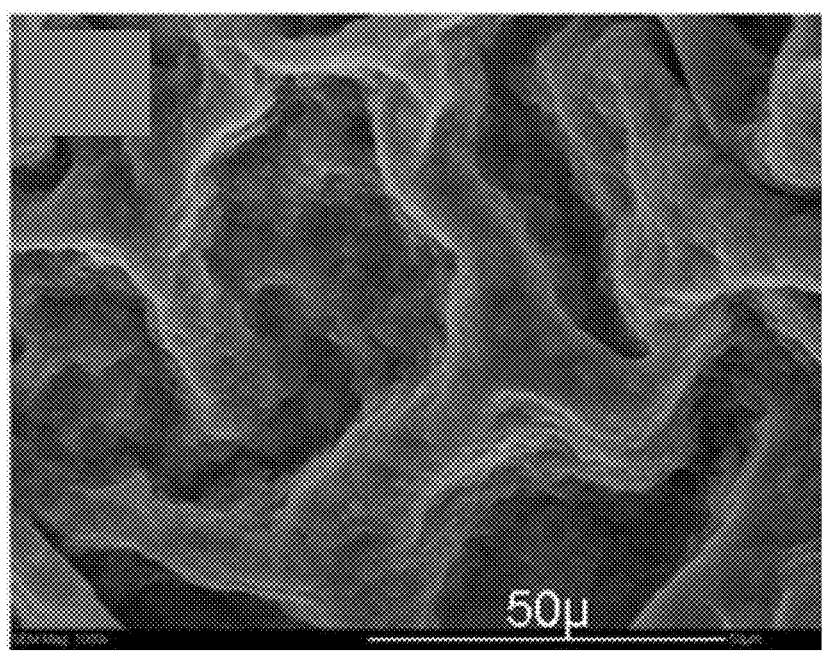
Figure 12C:
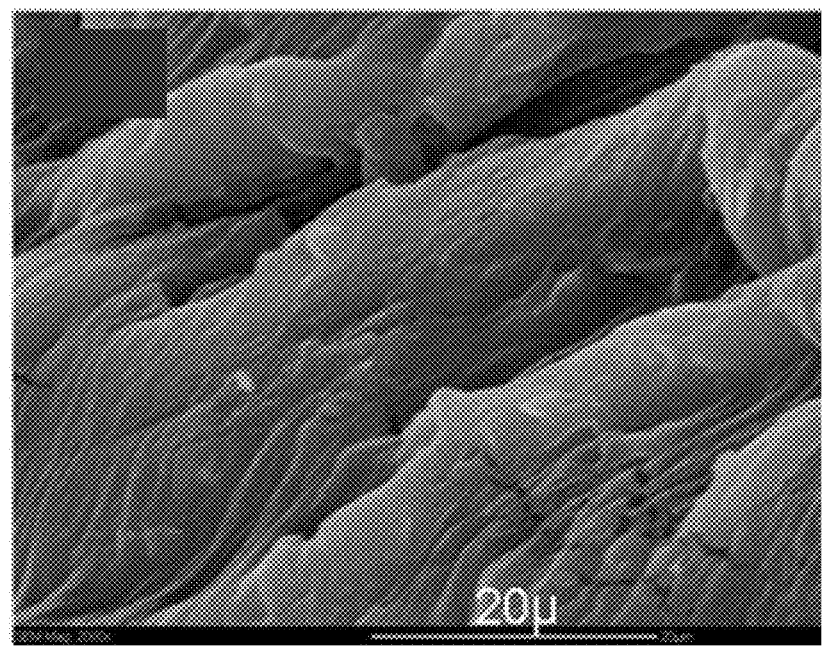

FIG. 12 shows the SEM images of dendrimer G4-NH$_2$—NHPDP crosslinked with 8-PEG-SH gel (FIG. 12A) 200μ (FIG. 12B) 50μ (FIG. 12C) 20μ. These gels were dehydrated by lyophilization.

Figure 13A:
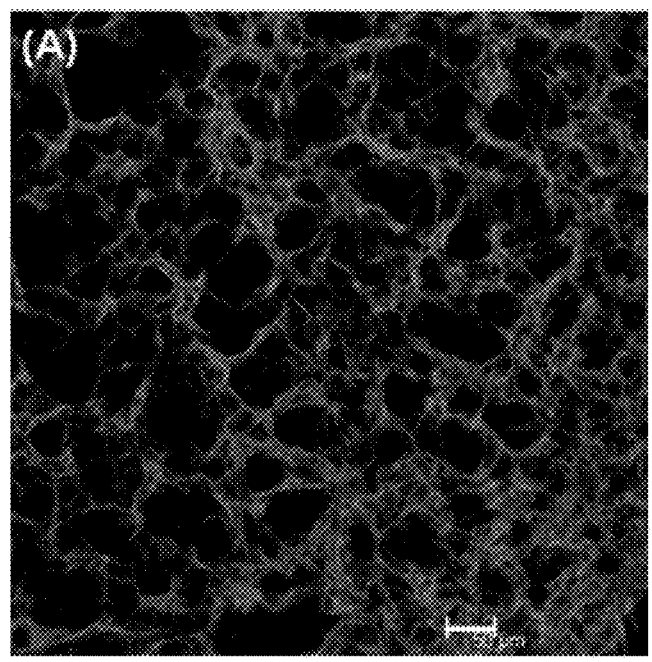
FIGS. 13A-C show hydrogel labeled with FITC to demonstrate the pore structure of the gel. By introducing the different concentration of polymer in the hydrogels, crosslinking density gradually increased by increasing the concentration of polymer. 3% hydrogel (FIG. 13A), 6% hydrogel (FIG. 13B), 10% hydrogel (FIG. 13C) shows the cross linking net work changes on increasing polymer concentration, scale bar represents 50μ.
Figure 13B:
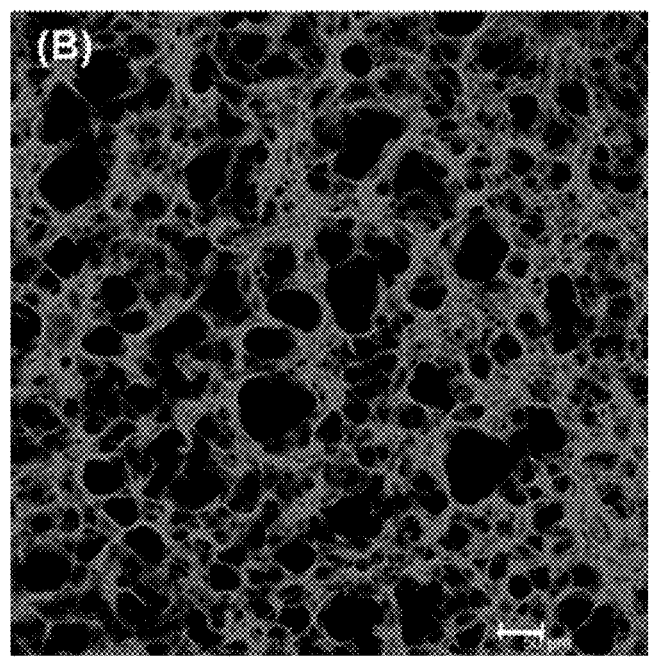
Figure 13C:
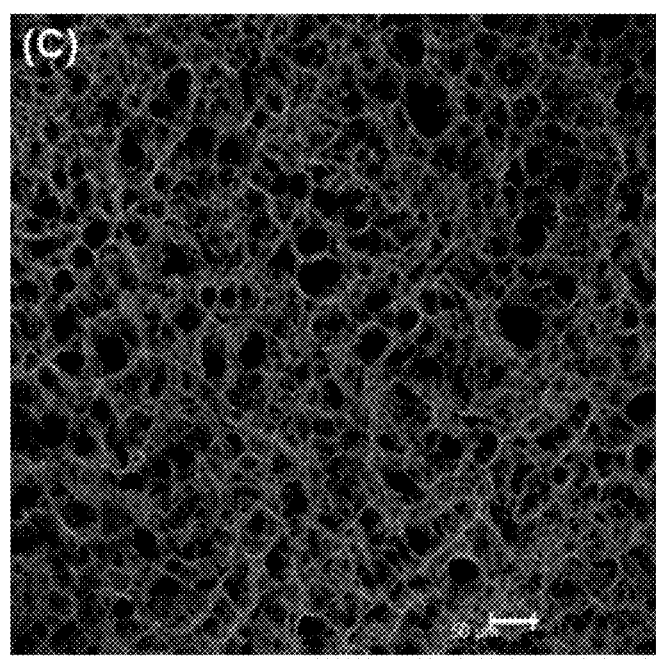

FIG. 13 shows hydrogel labeled with FITC to demonstrate the pore structure of the gel. By introducing the different concentration of polymer in the hydrogels, crosslinking density gradually increased by increasing the concentration of polymer. 3% hydrogel (FIG. 13A), 6% hydrogel (FIG. 13B) 10% hydrogel (FIG. 13C) shows the cross linking net work changes with increasing polymer concentration, scale bar represents 50μ.

Effect of Formulation Additives

The G4-NH$_2$—NHPDP and 8-arm-PEG-SH crosslinked hydrogels were formulated with glycerin (5%, v/v), PVP (4%, w/w) and PEG 600 (5%, v/v). The vaginal musoca is moist and at any given time the volume of the vaginal fluid is less than 1 mL and there is a possibility of fluid being reabsorbed. The studied hydrogels were placed in a vaginal environment with relatively low water content. The formulation additives were incorporated in the hydrogel to prevent it from becoming brittle and dehydrated. Glycerin and PEG 600 was incorporated in the hydrogels since they act as humectant and help maintain gels in plasticized supple form. The humectant properties of glycerin and PEG 600 are well known. PVP was incorporated in the gel to provide mucoadhesive property and to increase viscosity of the gel forming solutions to prevent their leak outside the cavity during instillation and formation of crosslinked hydrogels. Use of PVP in vaginal gels for enhancing the mucoadhesive properties is well known. The optimal concentration of the additives to prevent brittleness and increase retention time on vaginal mucosa for prolonged periods of time was found to be glycerin (5%, v/v), PVP (4%, w/w) and PEG 600 (5%, v/v).

Thermal Analysis

Figure 14A:
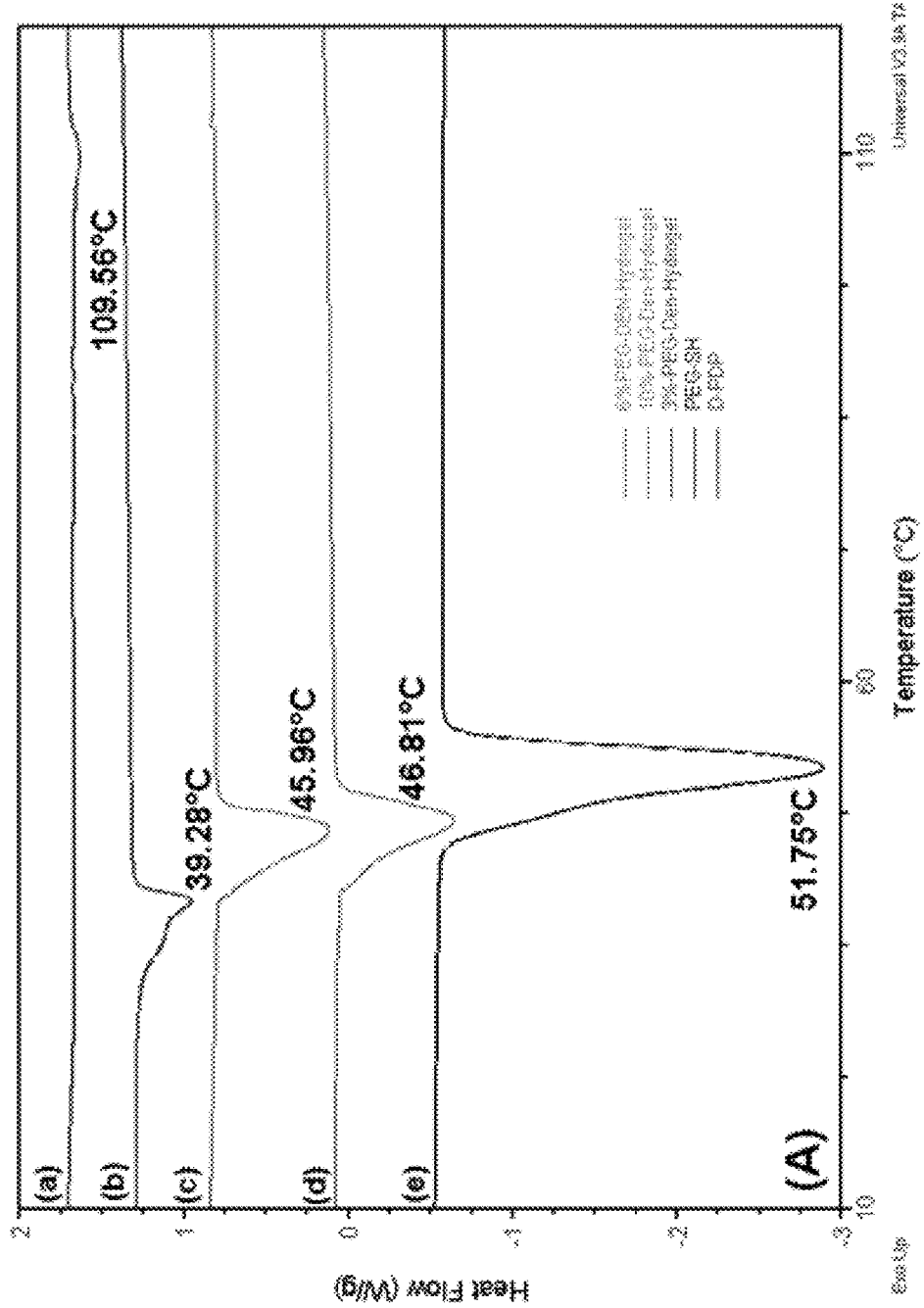
FIGS. 14A and 14B show the DSC thermograms for the 3, 6 and 10% dendrimer-PEG hydrogels.
Figure 14B:
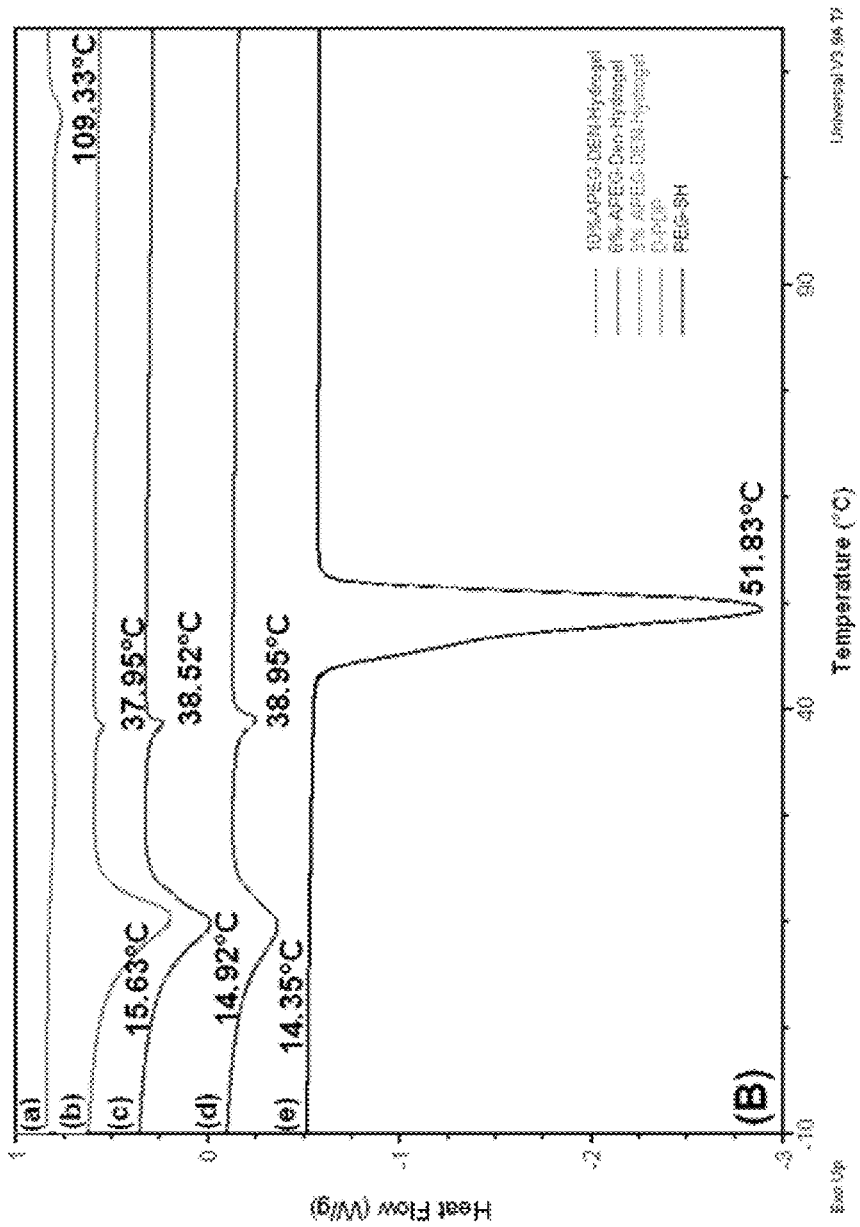

The thermal behavior of the dendrimer-PEG hydrogel components and the hydrogel was investigated by DSC analysis. The DSC thermograms of dendrimer-PEG hydrogels, G4-NH$_2$—NHPDP, 8-arm-PEG-SH, are shown in FIG. 14A. 8-arm-PEG-SH exhibits an endotherm at 51.7° C. (FIG. 14A (e)). The T$_g$ of G4-NH$_2$ dendrimer was −28° C. and G4-NH$_2$—NHPDP showed the presence of an endothermic peak at 109.3° C. with a T$_g$ at 21.4° C. (FIG. 14A (a)). The DSC profiles show that after dendrimer was converted to its PDP derivative, the T$_g$ shifted, indicating an altered polymer microstructure. When comparing the profiles of G4-NH$_2$—NHPDP and 8-arm-PEG-SH, the crosslinking of the two polymers clearly produced a new material having a microstructure different from either of its two components. In case of hydrogels the T$_g$ was found to be higher than that observed for the G4-NH$_2$—NHPDP, e.g. the 3% hydrogel exhibited at T$_g$ of 34.7° C. and the 10% and 6% hydrogels displayed a T$_g$ at 35.3° C. The 3, 6 and 10% hydrogels exhibited the endotherms at 39.2, 45.9 and 46.8° C. respectively which was lower than that observed for the 8-arm PEG-SH (51.7° C.). The intermolecular crosslinking of the polymer chains results in reduced mobility (resulting in increased T$_g$), and these polymer chains cannot reorient to form a highly ordered crystalline structure (lowered melting point). The addition of glycerin, PVP and PEG 600 lowered the endotherms of 3%, 6% and 10% hydrogels when compared to hydrogels without additives (FIG. 14B). The hydrogels with PEG 600 showed a characteristic endotherm between 15.6 to 14.3° C. in addition to the endotherm (37.9 to 38.9° C.) corresponding to 8-arm PEG-SH (FIG. 14B). The structural characteristics of both PEG hydrogel and dendrimer are seen in the dendrimer-PEG hydrogels.

FIG. 14 showed the DSC thermograms for the 3, 6 and 10% dendrimer-PEG hydrogels. (FIG. 14A) Hydrogels without formulation additives (absence of glycerin, PVP and PEG600), The 8-arm PEG-SH (e) shows an endotherm at 51.7° C., which is lowered upon crosslinking with G4-NH$_2$—NH-PDP as seen in curves (b), (c) and (d) for 3, 6 and 10% hydrogels respectively (FIG. 14B) Hydrogels with formulation additives (glycerin, PVP and PEG 600). In addition to the endotherms corresponding to 8armPEG-SH (37.9 to 38.9° C.) in hydrogels, an endotherm for PEG 600 is seen between 15.6 to 14.3° C.

Degradation of Hydrogels

The hydrogels investigated in the current study are biodegradable in nature. Their degradation was evaluated in simulated vaginal fluid and buffer since they were designed for intravaginal and intracervical application. The disulfide crosslinks in the hydrogels were used to lead to its slow degradation and easy self washout from the body orifice. The female reproductive tract secretions are rich in glutathione and glutathione transferase. GSH levels range between 28-284 mg in human cervical secretions. The disulfide linkages or crosslinks present in the gel are cleavable in presence of GSH. Thiol-disulfide exchange is a chemical reaction in which a thiolate group S⁻ attacks one of the sulfur atom of a disulfide bond —S—S—. Under basic or mild acidic conditions GSH is known to act as thiolate moiety and it gets oxidized while cleaving disulfide bonds. These reactions are facilitated at higher basic pH. Since vaginal pH is low (3.8-4.5) it was expected that disulfide bonds present in the hydrogels would undergo a slow degradation in vaginal environment. The in-vitro experiments showed that hydrogels were stable up to 3 days upon exposure to GSH solution at a pH 4.0, and in simulated vaginal fluid, and did not show any signs of degradation as seen in FIG. 15. After 72 hours the gels started to degrade and erode in both the solutions. This is consistent with the in-vivo degradation pattern, which is discussed in the subsequent sections. The chromatograms (what kind of SEC or HPLC) of the GSH solutions containing hydrogels did not show generation of any peaks until 50 hours (data not shown). After 65 hours the presence of few small peaks could be seen, which is attributed to breakdown of the gel into the smaller polymer components. The slow degradation of hydrogel is expected over time and would release the polymer components. The G4-$NH_2$ dendrimers exhibit antibacterial activity by altering bacterial cell walls. The G4-$NH_2$—NHPDP dendrimer is present in hydrogels has unmodified amine groups and was therefore expected to act as antibacterial agents. The antibacterial activity of partially pegylated amine terminated dendrimers is well known. Hence the hydrogels of the present study exhibit dual antibacterial mechanism attributed to the slow release of the amoxicillin followed by release of partially amine terminated G4 dendrimer.

Figures 15A, 15B:
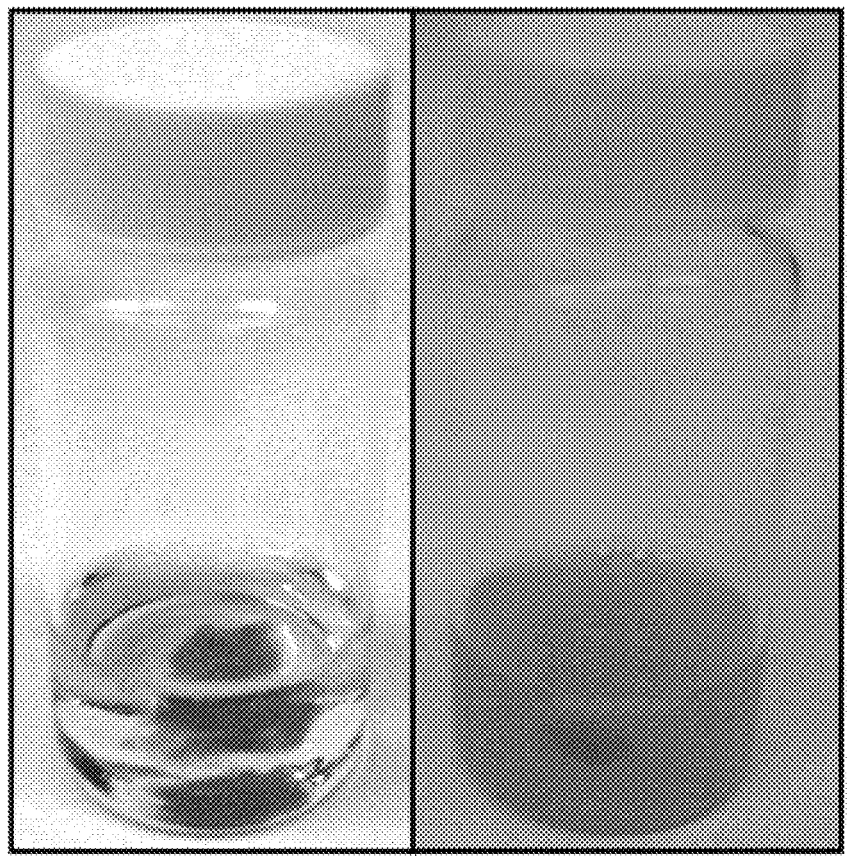
FIGS. 15A and B shows the dendrimer-PEG hydrogels exposed to the GSH solutions at pH 4.0 are stable up to 72 hours.
FIG. 15B shows the gel in simulated vaginal fluid with GSH.

FIG. 15 shows the dendrimer-PEG hydrogels exposed to the GSH solutions at pH 4.0 are stable up to 72 hours. FIG. 15A shows the intact gel after 72 hours of treatment with GSH solution at pH 4, FIG. 15B the gel in simulated vaginal fluid with GSH.

Degree of Swelling

The degree of hydrogels swelling was measured gravimetrically, calculating the equilibrium swelling obtained by comparing the ratios of the weights of the dry and water-swollen hydrogels over the time course. The degree of hydrogels swelling influences the pore size which affects the mechanical strength of the hydrogels and the drug release properties. The 3% hydrogel showed higher swelling when compared to 6% and 10% gels. The equilibrium swelling state was reached for the 3, 6 and 10% hydrogels at 10, 7 and 6 hours respectively. The observed pattern is attributed to the increased cross-linking density in hydrogels containing higher polymer concentration. In the confocal microscopy studies it was observed that the crosslinking density in 3% hydrogel was low as compared to the 6 and 10% and the swelling results in good agreement with this observation Drug Loading Efficiency Amoxicillin was physically entrapped in the in-situ forming gels. Amoxicillin was dissolved in the 8-arm PEG solution and mixed with the G4-$NH_2$—NHPDP solution to form the gel. The theoretical amounts of drug used for entrapment were 0.50 mg in 200 μL of hydrogel formulation (3, 6 and 10%). The drug extracts from the hydrogel were quantified by reverse phase (RP) HPLC analysis with UV detection at a wavelength of 229 nm using water: acetonitrile as mobile phase. The amount of drug entrapped in the 3, 6 and 10 w/v hydrogels was 52, 45 and 41% respectively. The 3% gels showed relatively higher drug loading efficiency compared to the 6 and 10% gels. This difference could be attributed to higher crosslinking density in gels with higher polymer concentration and reduced pores size.

In Vitro Drug Release

The in vitro drug release profiles from three different hydrogel formulations were studied using Franz diffusion cells. The plot of cumulative amount of drug released (mg/cm²) as a function of time (hours) from the three different types of hydrogels is presented in FIG. 16A. The drug release plot shows that amoxicillin release was sustained for 260 hours with a release of 72%, 63%, 51% from 3%, 6% and 10 hydrogels respectively. A relatively slower drug release was observed from 10% hydrogel when compared to 3% hydrogel. This result is consistent with the lower swelling of the 10% hydrogel, which is attributed to the high crosslinking density in polymer network obtained for higher polymer concentrations, leading to smallerpores size. The plot of percentage drug released verses time was used to determine the release mechanism (FIG. 16B). The data (first 60% of the amount release) was fitted to explain the release mechanism and pattern using the Peppas equation as follows:

$$\frac{M_t}{M_\infty} = kt^n \qquad \text{(eq. I)}$$

Where $M_t/M_\infty$ is the fraction of drug released, 'k' is a kinetic (proportionality) constant dependent on the system, 't' is the time period for release, and 'n' is the diffusion exponent indicative of the release mechanism for matrices of various shapes and swelling patterns. In the case of Fickian release, the exponent 'n' has a limiting value of 0.50, 0.45, and 0.43 from slabs, cylinders, and spheres, respectively. The values of 'n' and 'k' are inversely related, and a higher value of 'k' suggests a burst release of drug from matrix. The values of diffusional exponent are shown in Table 5. At higher polymer concentration (10%) the drug release mechanism seems to approach the Fickian diffusion with n=0.49, while the lower polymer concentrations exhibit non Fickian release mechanism.

TABLE 5

Determination of flux, diffusional exponent (n) and permeability coefficient for hydrogels

| % w/v Hydrogels | Flux (J) (mg cm⁻² s⁻¹) × 10⁻⁷ | Diffusion exponent (n) | Permeability Coefficient (P) (cm · h⁻¹) × 10⁻⁶ |
|---|---|---|---|
| 3% | 4.72 | 0.20 | 1.81 |
| 6% | 4.16 | 0.25 | 1.85 |
| 10% | 3.88 | 0.49 | 1.89 |

Permeation parameters were obtained from the cumulative amounts of drug permeated (mg cm⁻²) as a function of time (hours). The steady state flux (J) representing the absorption rate per unit area was determined from the slope of the linear portion of the plots. In all experiments same number of data points was taken to calculate the steady state flux. The permeability constant (P) was calculated according to Fick's first law of diffusion, based on the steady state flux and the applied drug concentration (Ci) on the donor side. The permeability coefficients were deduced, dividing the flux by the initial drug load (Ci) as shown in equation:

$$J = \frac{dQ}{dt \cdot A} \qquad \text{(eq. II)}$$

$$P = \frac{J}{Ci} \qquad \text{(eq. III)}$$

Figure 16A:
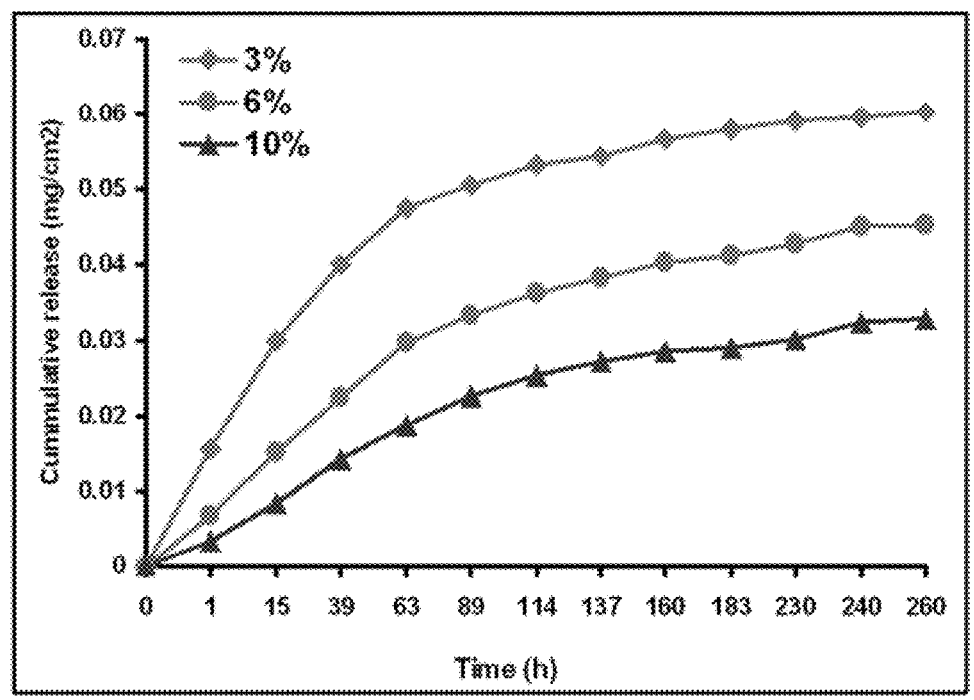
FIG. 16A shows the cumulative amount of amoxicillin released with respect to time (h) across per cm$^2$ area for 3, 6 and 10% hydrogels
Figure 16B:
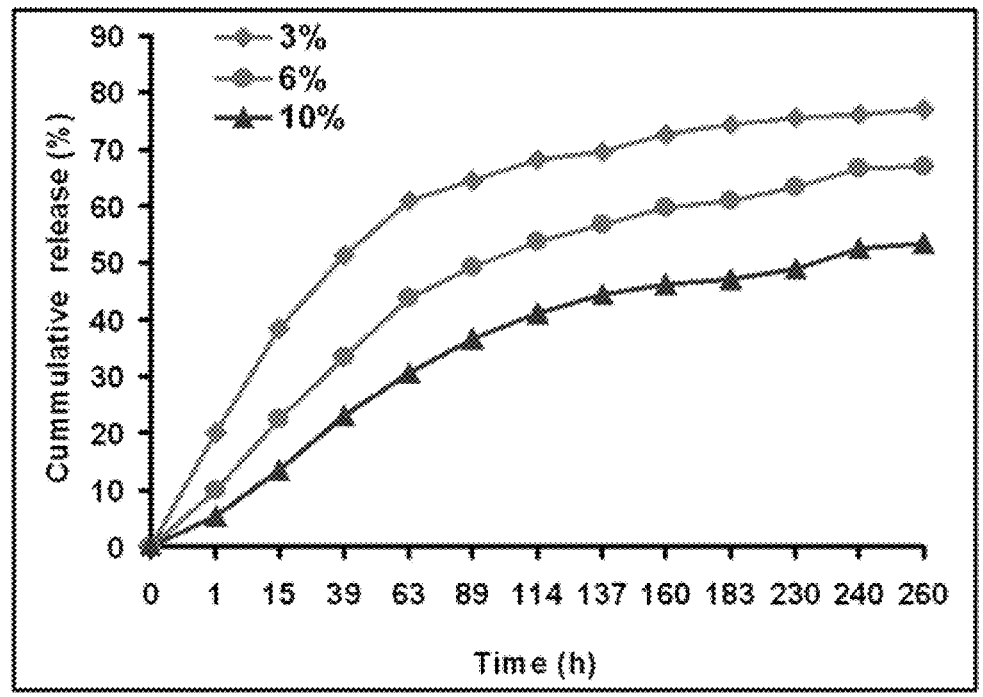
FIG. 16B shows cumulative amount of amoxicillin released with respect to time. The release mechanism was found to be non-fickian for 3 and 6% hydrogels while for 10% hydrogels it approached fickian diffusion.
Figure 17A:
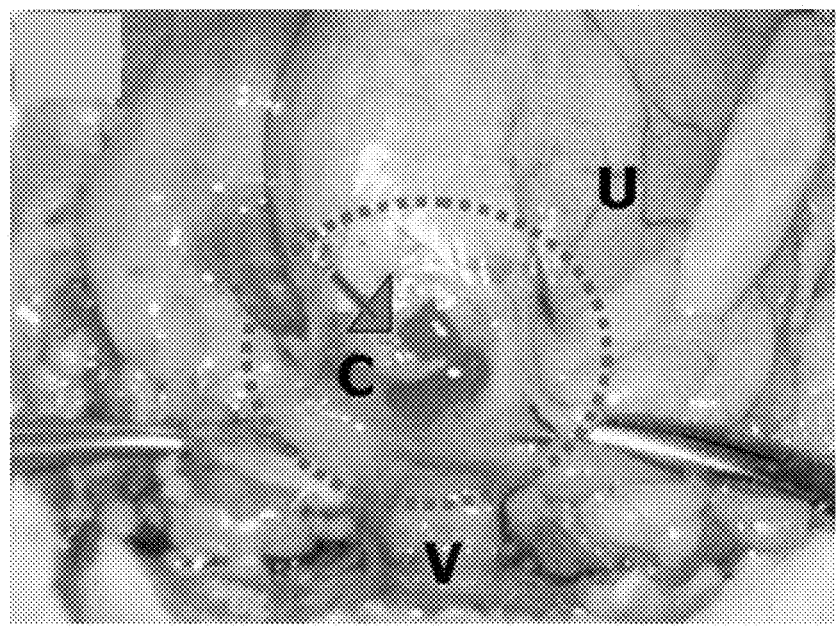
FIGS. 17A-D show intravaginal and intracervical application of in-situ forming Dendrimer-PEG hydrogels in the pregnant guinea pigs. The green arrows mark the presence of hydrogel on the tissue (FIG. 17A) day 1: hydrogel after 5 h of application, (FIG. 17B) day 1: hydrogel after 12 h of application (FIG. 17C) day 2: after hydrogel application (FIG. 17D) day 3: after hydrogel application, where 'C'=cervix, V=vaginal cavity, U=uterus with pups. The hydrogel is retained in the cervix and vaginal cavity for 2 days and on day 3 it's seen largely in the vaginal cavity of pregnant guinea pigs.
Figure 17B:
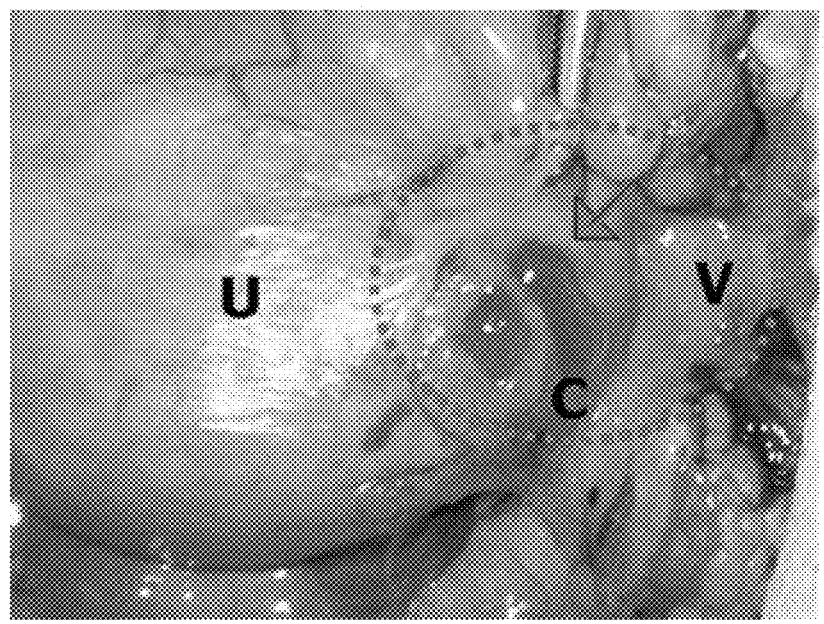
Figure 17C:
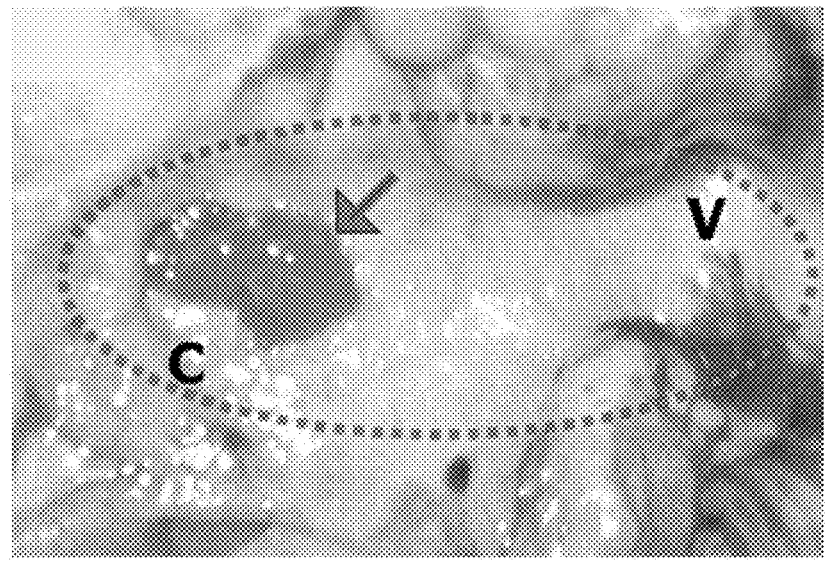
Figure 17D:
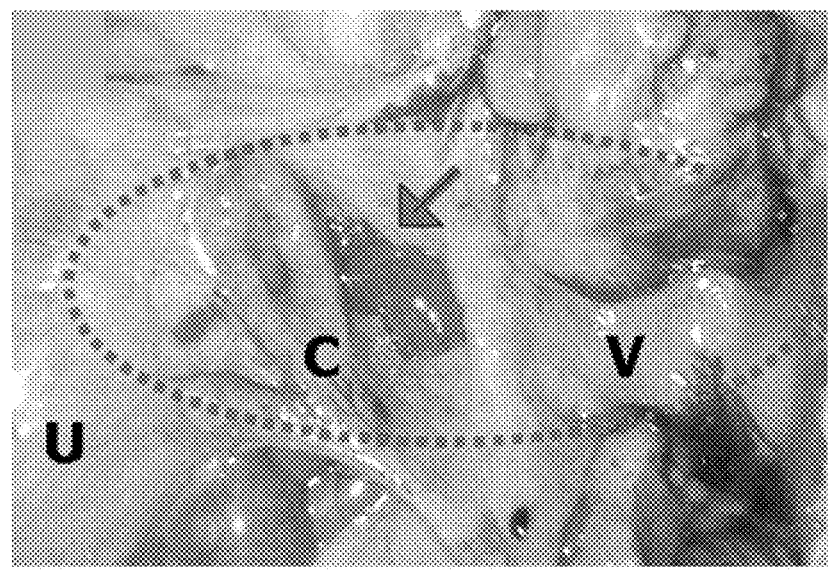

FIG. 16A) shows a cummulative amount of amoxicillin released with respect to time (hours) across per cm² area for 3, 6 and 10% hydrogels and FIG. 16B) shows a cumulative amount of amoxicillin released with respect to time. The release mechanism was found to be non-fickian for 3 and 6% hydrogels while for 10% hydrogels it approached fickian diffusion.

The flux, diffusional exponent and permeability coefficient are collected in Table 5. The flux and permeability was found to decrease with the increase in the polymer concentration. This is due to the increased crosslinking density and lower swelling of the hydrogels at higher polymer content. Observed result is consistent with the lower drug release rate at higher polymer concentrations. At higher PEG concentrations (20-45% w/v) the PEG hydrogels exhibit 10 folds higher flux as compared to the dendrimer-PEG hydrogels. This indicates that the PEG-dendrimer hydrogel forms a tighter network in comparison to the PEG crosslinked hydrogels. Investigated dendrimer-PEG hydrogels are therefore expected to sustain the drug release efficiently.

In-Vivo Testing of Hydrogel Formulations in Guinea Pig Model

Figure 18A:
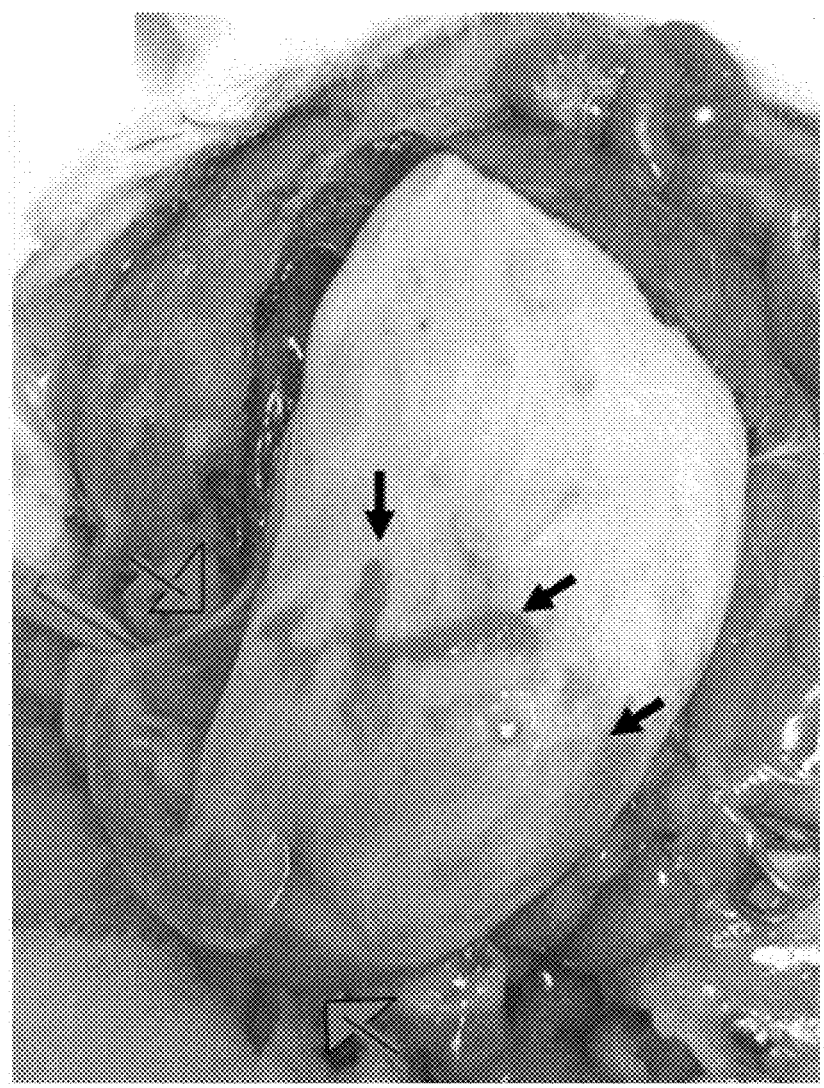
FIGS. 18A-C show the Dendrimer-PEG hydrogels after intravaginal and intracervical application in pregnant guinea pigs do not cross the fetal membrane and enter into the gestational (sac) cavity.
Figure 18B:
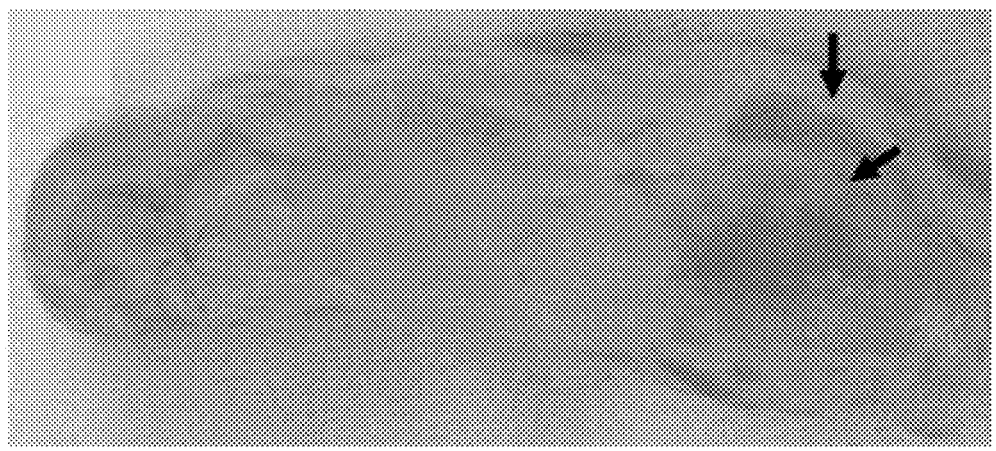

Vaginal distribution, retention, biodegradation and tolerability of gels are important parameters to achieve sustained residence in the body cavity. Discussed intravaginal gels were developed to treat the ascending genital infections during pregnancy. Since the gel is in-situ forming, permeation and transport of the gel (PEG and G4-NH$_2$—NH-PDP polymers) across the fetal membranes into the fetus was investigated. The 10% w/v gels were used for in-vivo testing as these were found to sustain the drug release for longer times as compared to 3 and 6% gels. The volume of the gel for intravaginal application was determined by injecting the samples 100 µL to 500 µL. The ideal volume for application was found to be 200 µL and any volume above that resulted in leaking of the gel material outside the vagina. Similar volumes for intravaginal gels in guinea pigs were reported. The hydrogels without formulation additives exhibited short residence times and were leaked out as brittle particles after 24 hours. The gels with formulation additives (glycerin, PVP and PEG 600) were retained in the cervicovaginal region at least up to 72 hours, the end point used in this protocol. The incorporation of PVP in the gels provides the mucoadhesive effect. FIG. 17 shows the presence of gel after 5, 12, 24 and 72 hours of application. The visual examination revealed that 200 µL gel volume was sufficient to cover the cervicovaginal region. The gel could be seen in the cervicovaginal region in the early hours after application (5 and 12 hours) and the gel was retained in this region even at later time points (24 to 72 hours). The gel was found to slowly degrade with change in morphology and the eroded material was seen on the fetal membranes of the pups positioned very close to the cervix (FIG. 18A). The gel was not seen on any other pup (fetus) positioned away from the cervix. It is interesting to note that the gels with disulfide bonds exhibited a slow degradation in-vivo in vaginal environment. This observation is similar to the in-vitro degradation study in simulated vaginal fluid with GSH at pH 4. The gel components remained on the surface of the fetal membranes without transport across the membranes (FIGS. 18A and 18B). The G4-NH$_2$—NHPDP dendrimer conjugate released due to degradation of the gel is not seen across the fetal membrane. The pups did not show traces of gel on fur after removal of the fetal membranes (FIG. 18C) indicating that the gel does not cross across the fetal membranes and can be used for the selective local treatment of the pregnant mother without transfer to the fetus. The previous ex-vivo studies in human fetal membranes showed that the transport of FITC labeled G4-NH$_2$ dendrimer is restricted across the membrane. Presented in-vivo results combined with the previous ex-vivo studies indicate that the hydrogels formed using the G4-NH$_2$—NH-PDP and 8-arm-PEG-SH do not cross the fetal membranes and could be used for the selective local treatment of pregnant woman without transfer to the fetus. The pH of vagina was tested after 5 hours, 12 hours and 24 hours of hydrogels application, using the swabs. No change in pH was observed after application of the gel. The investigated hydrogels were formed rapidly in-situ and they absorb buffer in which they were formed without affecting pH of vagina. None of the animals showed any discomfort after application of gel, none of the animals aborted in 72 hours. The visual examination of the vaginal tissues showed no signs of edema and irritation and the gels were well tolerated by the animals.

FIG. 17 shows the intravaginal and intracervical application of in-situ forming dendrimer-PEG hydrogels in the pregnant guinea pigs. The green arrows mark the presence of hydrogel on the tissue (FIG. 17A) day 1: hydrogel after 5 hours of application, (FIG. 17B) day 1: hydrogel after 12 hours of application (FIG. 17C) day 2: 24 hours after hydrogel application (FIG. 17D) day 3: 72 hours after hydrogel application, where 'C'=cervix, V=vaginal cavity, U=uterus with pups. The hydrogel is retained in the cervix and vaginal cavity for 2 days and on day 3 it's seen largely in the vaginal cavity of pregnant guinea pigs.

Figure 18C:
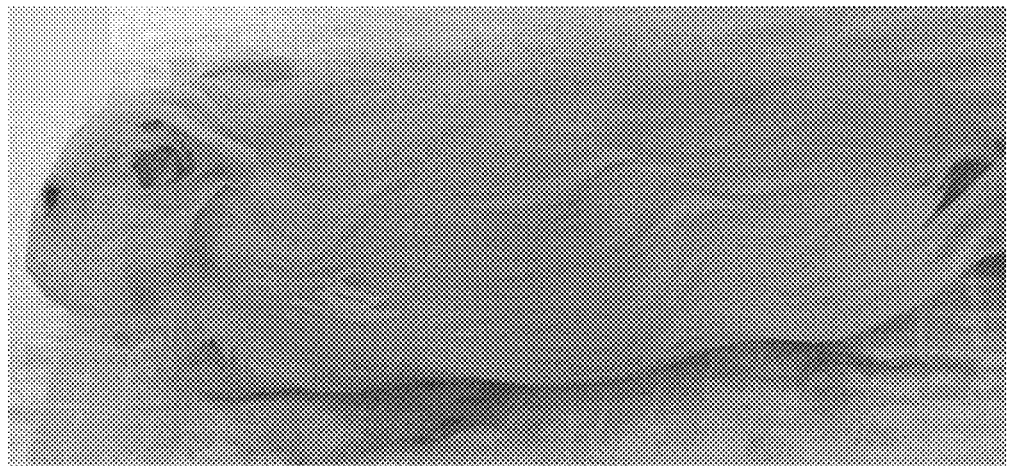
Figure 19A:
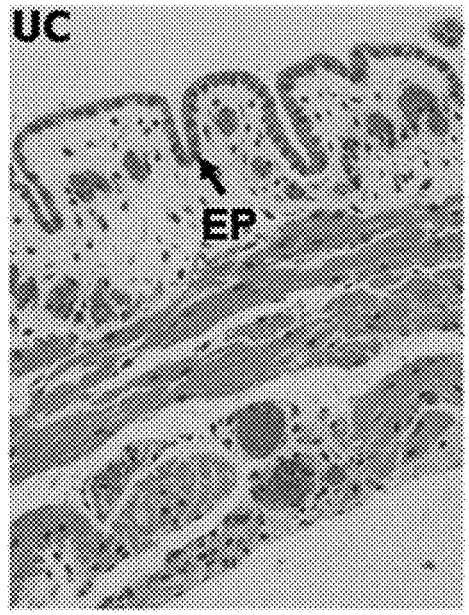
FIGS. 19A-I show the hemotoxylin and eosin stained histological sections of uterus (U), upper cervix (Ucx) and cervix (Cx) of guinea pig treated with the hydrogels for 24 hours and 72 hours (n=3 per group). The epithelial cell lining in all the tissues is intact and does not show any signs of inflammation and edema. The submucosa of hydrogel treated cervix after 24 and 72 hours is comparable to the control. None of the tissues showed any signs of epithelial sloughing, necrosis in the submucosa or massive infiltration of inflammatory cells. EP=epithelial cells, SE=subepithelium, SM=submucosa, M=muscular layer EGO=endometrial gland cells.
Figure 19B:
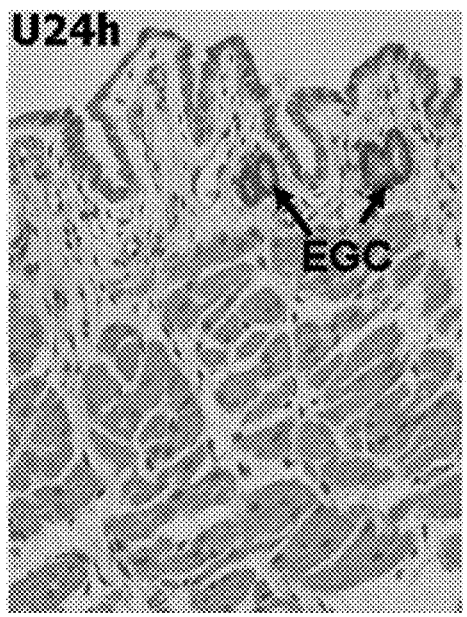
Figure 19C:
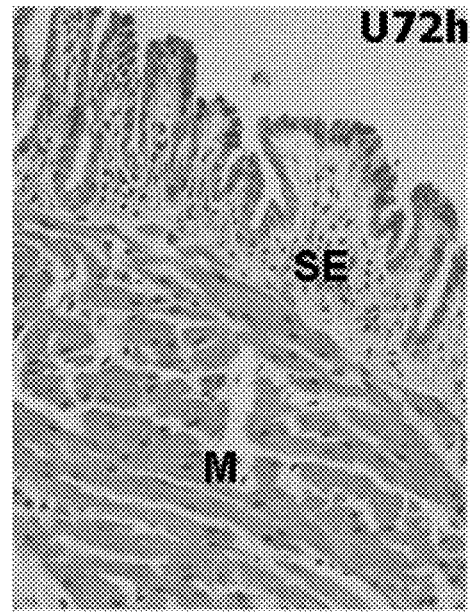
Figure 19D:
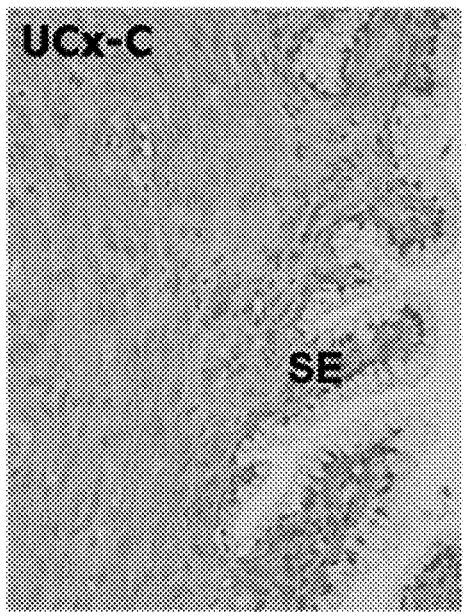
Figure 19E:
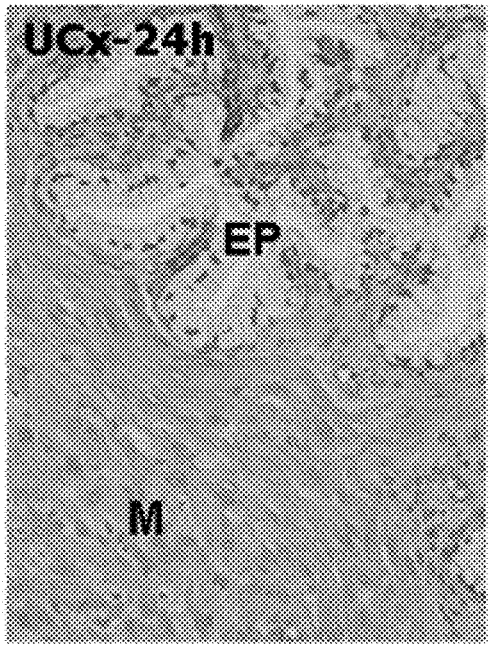
Figure 19F:
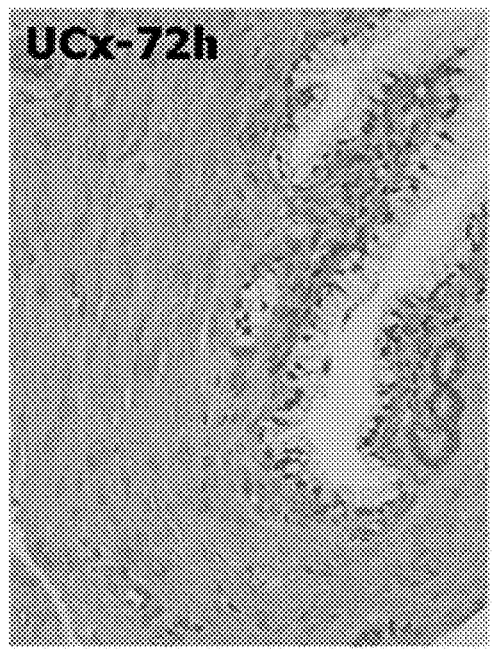
Figure 19G:
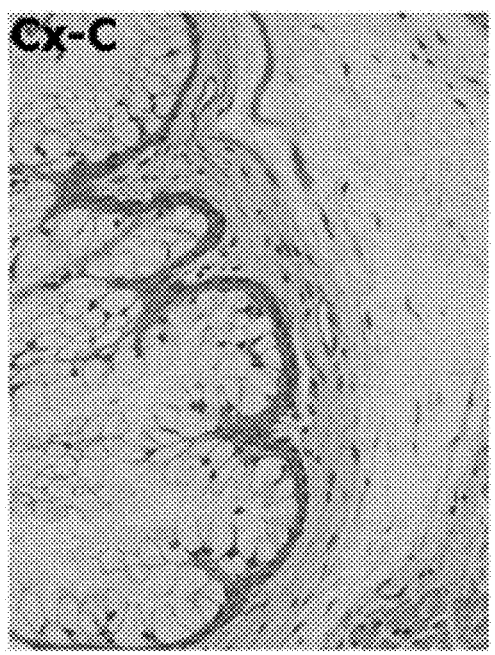
Figure 19H:
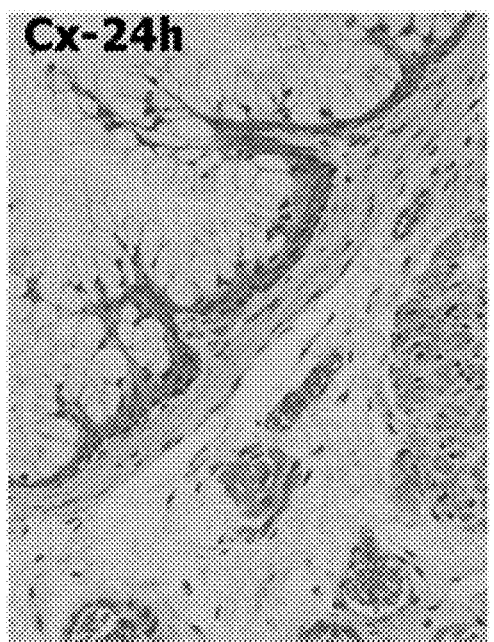
Figure 19I:
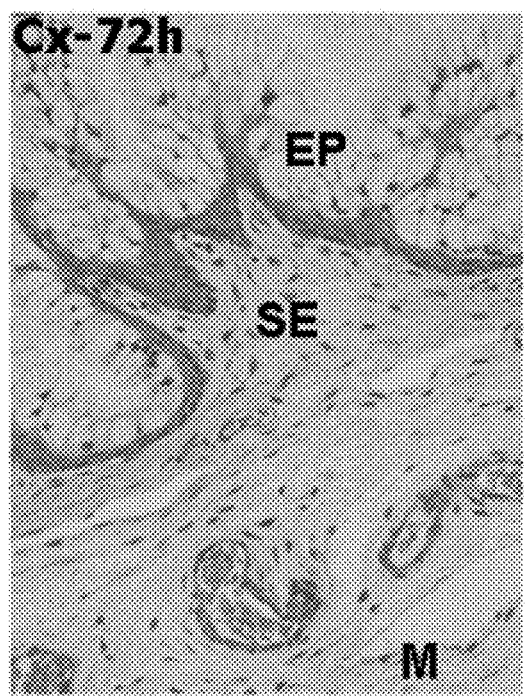

FIG. 18 shows the dendrimer-PEG hydrogels after intravaginal and intracervical application in pregnant guinea pigs do not cross the fetal membrane and enter into the gestational (sac) cavity. (FIG. 18A) day 3: hydrogel seen on the fetal membrane of the pup positioned close to the cervix, the green arrows mark the presence of fetal membrane on the pup, the black arrows show the presence of gel outside of the fetal membrane (FIG. 18B) the pup covered in fetal membrane with hydrogel on top of the fetal membrane (FIG. 18C) the pup after removal of the fetal membrane showing no signs of hydrogel on the fur or inside the fetal membrane.

The histological evaluation of the uterus and cervicovaginal epithelial layer shows that the cell layer was not disrupted and no morphological changes were observed in the cells after 24 and 72 hours treatment with hydrogels (FIG. 19; see Brief Description for additional detail). The epithelial layer of the control tissue and the 24 and 72 hours tissue with hydrogel treatment appear comparable. There are no signs of sloughing of the epithelial cells into the lumen, inflammation or edema of the epithelium. The submucosal tissues after hydrogel treatment (24 and 72 hours) did not show any signs of necrosis or massive infiltration of the inflammatory cells. The cervical tissues show presence of the superficial mucous cell layer and after treatment with hydrogels the tissues do not show any signs of sloughing of the superficial mucous layer.

FIG. 19 shows the hemotoxylin and eosin stained histological sections of uterus (U), upper cervix (Ucx) and cervix (Cx) of guinea pig treated with the hydrogels for 24 hours and 72 hours (n=3 per group). The epithelial cell lining in all the tissues is intact and does not show any signs of inflammation and edema. The submucosa of hydrogel treated cervix after 24 and 72 hours is comparable to the control. None of the tissues showed any signs of epithelial sloughing, necrosis in the submucosa or massive infiltration of inflammatory cells. EP=epithelial cells, SE=subepithelium, SM=submucosa, M=muscular layer EGO=endometrial gland cells, UC=uterus control, U24 and 72 hours=hydrogel treated uterus 24 and 74 hours, UCxC=control upper cervix, UCx24 and 72 hours=hydrogel treated upper cervix 24 and 74 hours, Cx-C=cervix control, Cx24 and 72 hours=hydrogel treated cervix 24 and 74 hours (40× magnification).

FIG. 20 shows the confocal images of the cervical region of pregnant guinea pigs treated with hydrogels for 24 (FIGS. 20A and 20D) and 72 hours (FIGS. 20B and 20E). The in-situ forming hydrogel comprising FITC-G4-NH-PDP crosslinked with 8-arm PEG-SH was applied to the cervicovaginal region. The hydrogel (green color) is seen on the surface of the mucosal layer (red color). The confocal images after 24 and 72 hours confirm the presence of the gel on the tissue surface. The nuclei for all cells are stained blue with DAPI. There is no sign of the degraded gel into the subepithelial or submucosal layers. EP=epithelial layer, SE=subepithelial layer, ML=mucified epithelial layer (FIGS. 20C and 20F).

No signs of atropy of the epithelial cell layer or the superficial mucous layer were observed after the hydrogel treatment for 72 hours. The animals treated with hydrogels did not show any signs of thickening of the mucous cell layer when compared to the control animal (FIG. 19). These results suggested that the animals were tolerant to the gels and no untoward reaction was exhibited. The residence of the gel on the mucified epithelial cells of the cervicovaginal region was further confirmed from the histological evaluation of immunohistofluorescence images (FIG. 20). The fluorescent gel comprising G4-NH$_2$-FITC-NHPDP crosslinked with 8-arm PEG-SH was used for this investigation and the cross sections of the vagina and cervix show the presence of fluorescent gel (green color) on the mucified epithelial layer (red) marked positive with anticytokeratin. The presence of gel is apparent at time points 24 and 72 hours respectively. The immunohistofluorescence images of the fetal membrane and the uterus at 72 hours do not show the presence of the gel across these tissues (FIG. 21), as seen by the absence of the fluorescent green. These results confirm that the gel components are primarily located on the epithelial surface of cervical region and do not cross into deeper tissue. The ascending bacterial infection causes chorioamnionitis which is associated with development of cerebral palsy, a motor disorder in children due to stimulation of proinflammatory cytokines causing white matter damage and fetal brain injury. The local delivery of antibiotics in the cervicovaginal region is preferred therapy for the treatment of these infections.

Figure 21A:
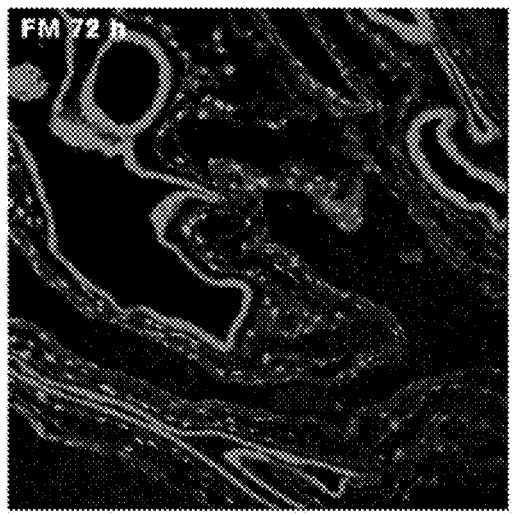
FIGS. 21A and 21B show the confocal images of the fetal membrane and uterus of guinea pigs treated with hydrogels for 72 hours. The in-situ forming hydrogel comprising FITC-G4-NH-PDP crosslinked with 8-arm PEG-SH was applied to the cervicovaginal region. The cross section of the uterus (FIG. 21B) and the fetal membrane (FIG. 21A) do not show presence of hydrogel or degraded hydrogel across the tissue.
Figure 21B:
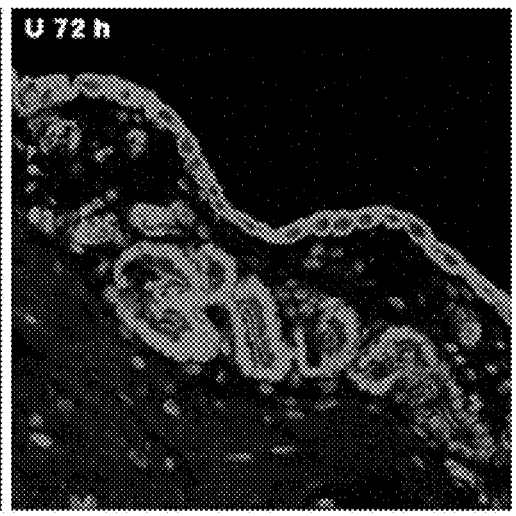
Figure 22:
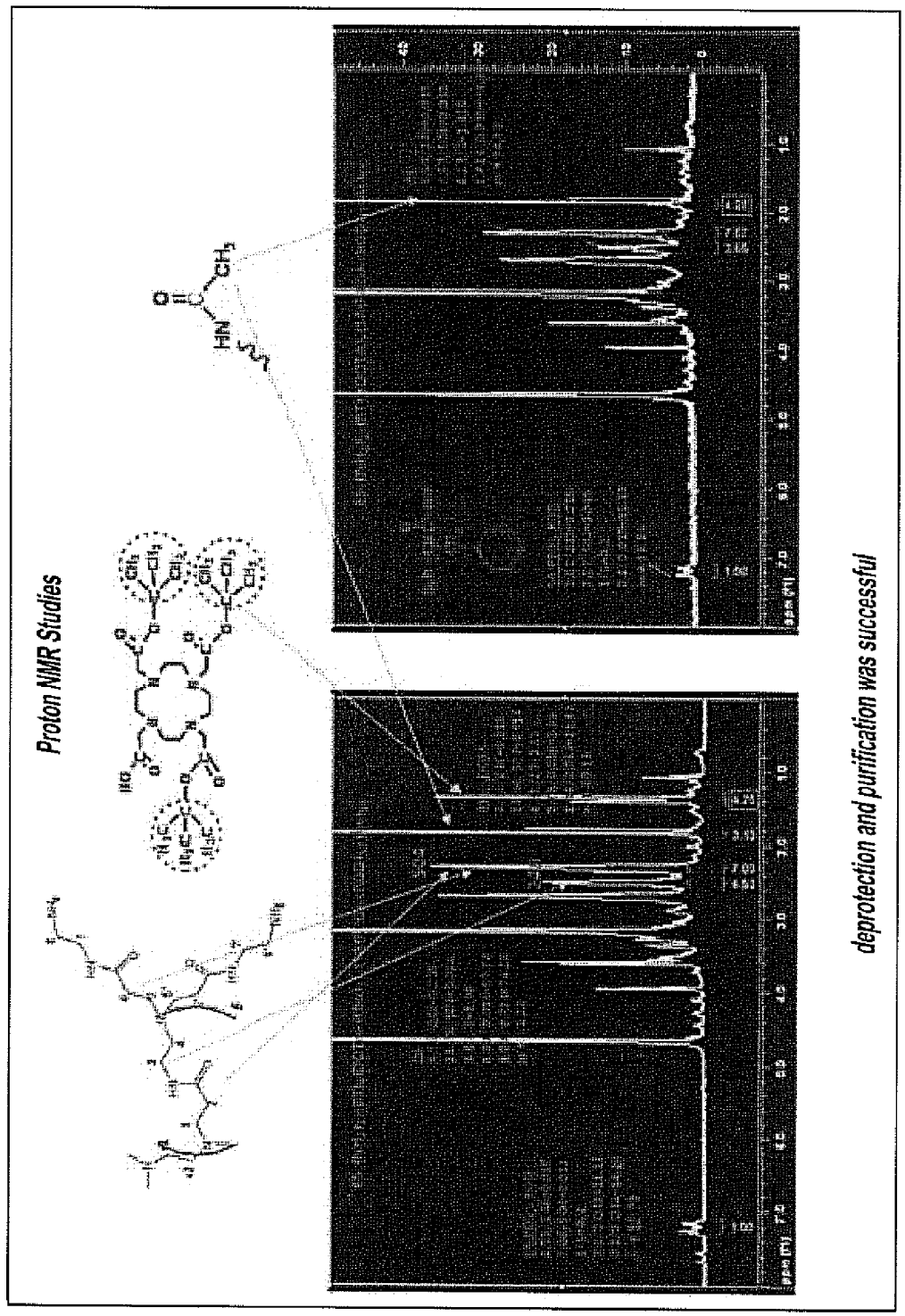
FIG. 22 shows an example of an NMR figure.

FIG. 21 shows the confocal images of the fetal membrane and uterus of guinea pigs treated with hydrogels for 72 hours. The in-situ forming hydrogel comprising G4-NH$_2$-FITC-NHPDP crosslinked with 8-arm PEG-SH was applied to the cervicovaginal region. The cross section of the uterus (FIG. 21A) and the fetal membrane (FIG. 21B) do not show presence of hydrogel or degraded hydrogel across the tissue.

The hydrogels exhibited long residence times of at least 72 hours and were very well tolerated by the tissues. The hydrogels exhibit dual antibacterial activity by the release of amoxicillin followed by the release of partially modified amine terminated dendrimer due to degradation of the hydrogels. Dendrimers with amine terminations exhibit antibacterial activity. The covalent linking of the dendrimer to the PEG overcomes the cytotoxicity associated with the dendrimer which is well documented. These findings are significant as the dendrimers in the size range 5 to 6 nm do not cross the human fetal membranes which separate the extra-amniotic cavity and the fetus, and could be used for the local intravaginal delivery of pregnant woman. The overall findings of the present study suggest that the proposed hydrogels offer an excellent degradable drug delivery system which exhibits sustained local delivery of the antibacterial agents intravaginally to the pregnant mother without transfer to the fetus.

CONCLUSIONS

Drug therapy during pregnancy is challenging, and effective ways to selectively treat the pregnant woman without affecting the fetus are always desired. Topical delivery of therapeutic agents is favored to treat ascending genital infections in pregnant women. Biodegradable in-situ forming hydrogels obtained by crosslinking of G4-NH$_2$-FITC-NHPDP dendrimer and 8-arm PEG via formation of disulfide bridges is described. Amoxicillin release from these hydrogels (3, 6 and 10% w/v) is sustained for more than 240 hours and the release approaches Fickian diffusion pattern from the 10% w/v hydrogels. The in-vivo evaluation of the hydrogels using pregnant guinea pig model shows that gels are very well tolerated by the animals and no signs of change in vaginal pH and erythema are observed up to 72 hours. The gel volume of 100-200 µl was found to sufficiently cover the entire cervicovaginal region as seen by visual examination. The gels exhibited a slow degradation in-vivo at the vaginal pH and the degraded gel was retained in the maternal tissues without transfer across the fetal membranes. These results were confirmed by visual and immunohistofluorescence images of tissues which showed that the gel is largely retained in the superficial mucified epithelial cells. The histopathological evaluation of the vaginal and the cervical tissues showed absence of epithelial cell edema, necrosis and infiltration of inflammatory cells in the subepithelial and submucosal tissues. There were no signs of sloughing of the superficial epithelial cell layer after application of the hydrogels. The morphology of the tissues treated with the hydrogels for 24 and 72 hours was comparable to that of the control tissues. The overall results confirm that the gels were very well tolerated by the animals and none of the animals aborted in 72 hours after application of gels. The in-situ forming hydrogels of the present invention offer therapeutic approaches to provide localized selective treatment of the pregnant woman with ascending genital infections without adverse effects to the fetus.

Throughout this application, author and year and patents by number reference various publications, including United States patents. Full citations for the publications are listed below. The disclosures of these publications and patents in their entireties are hereby incorporated by reference into this application in order to more fully describe the state of the art to which this invention pertains.

The invention has been described in an illustrative manner, and it is to be understood that the terminology, which has been used herein, is intended to be in the nature of words of description rather than of limitation.

Obviously, many modifications and variations of the present invention are possible in light of the above teachings. It is, therefore, to be understood that within the scope of the described invention, the invention can be practiced otherwise than as specifically described.

REFERENCES

1. Svenson, S.; Tomalia, D. A., Dendrimers in biomedical applications—reflections on the field. *Adv Drug Deliv Rev* 2005, 57, (15), 2106-29.
2. Goodwin, A. P.; Lam, S. S.; Frechet, J. M. J., Rapid, Efficient Synthesis of Heterobifunctional Biodegradable Dendrimers. *Journal of the American Chemical Society* 2007, 129, (22), 6994-6995.
3. Menjoge, A. R.; Kannan, R. M.; Tomalia, D. A., Dendrimer-based drug and imaging conjugates: design considerations for nanomedical applications. *Drug Discov Today.* 2010, 15, 171-185
4. Okuda, T.; Kawakami, S.; Maeie, T.; Niidome, T.; Yamashita, F.; Hashida, M., Biodistribution characteristics of amino acid dendrimers and their PEGylated derivatives after intravenous administration. *J Control Release* 2006, 114, (1), 69-77.
5. Tomalia, D. A., Reyna, L. A., Svenson, S., Dendrimers as multi-purpose nanodevices for oncology drug delivery and diagnostic imaging. *Biochemical Society Transactions* 2007, 35, 61-67.
6. Lee, C. C.; MacKay, J. A.; Frechet, J. M.; Szoka, F. C., Designing dendrimers for biological applications. *Nat Biotechnol* 2005, 23, (12), 1517-26.
7. Sato, N.; Kobayashi, H.; Saga, T.; Nakamoto, Y.; Ishimori, T.; Togashi, K.; Fujibayashi, Y.; Konishi, J.; Brechbiel, M. W., Tumor targeting and imaging of intraperitoneal tumors by use of antisense oligo-DNA complexed with dendrimers and/or avidin in mice. *Clin Cancer Res* 2001, 7, (11), 3606-12.
8. Han, H. J.; Kannan, R. M.; Sunxi, W.; Guangzhao, M.; Juan Pedro, K.; Roberto, R., Multifunctional Dendrimer-Templated Antibody Presentation on Biosensor Surfaces for Improved Biomarker Detection. Adv. Fund. Mater. 2010, 20, 409-421.
9. Navath, R. S.; Kurtoglu, Y. E.; Wang, B.; Kannan, S.; Romero, R.; Kannan, R. M., Dendrimer-drug conjugates for tailored intracellular drug release based on glutathione levels. *Bioconjug Chem* 2008, 19, (12), 2446-55.
10. Antoni, P.; Hed, Y.; Nordberg, A.; Nystrom, D.; von Holst, H.; Hult, A.; Malkoch, M., Bifunctional dendrimers: from robust synthesis and accelerated one-pot post-functionalization strategy to potential applications. *Angew Chem Int Ed Engl* 2009, 48, (12), 2126-30.
11. Kolhe, P.; Misra, E.; Kannan, R. M.; Kannan, S.; Lieh-Lai, M., Drug complexation, in vitro release and cellular entry of dendrimers and hyperbranched polymers. *Int J Pharm* 2003, 259, (1-2), 143-60.
12. Kurtoglu, Y. E.; Navath, R. S.; Wang, B.; Kannan, S.; Romero, R.; Kannan, R. M., Poly(amidoamine) dendrimer-drug conjugates with disulfide linkages for intracellular drug delivery. *Biomaterials* 2009, 30, (11), 2112-21.
13. Khandare, J.; Kolhe, P.; Pillai, O.; Kannan, S.; Lieh-Lai, M.; Kannan, R. M., Synthesis, cellular transport, and activity of polyamidoamine dendrimer-methylprednisolone conjugates. *Bioconjug Chem* 2005, 16, (2), 330-7.
14. Gillies, E. R.; Frechet, J. M. J., Designing Macromolecules for Therapeutic Applications: Polyester DendrimerPoly(ethylene oxide) â€œBow-Tieâ€ Hybrids with Tunable Molecular Weight and Architecture. *Journal of the American Chemical Society* 2002, 124, (47), 14137-14146.
15. Sivanandan, K.; Vutukuri, D.; Thayumanavan, S., Functional group diversity in dendrimers. *Org Lett* 2002, 4, (21), 3751-3.
16. Fischer-Durand, N.; Salmain, M.; Rudolf, B.; Juge, L.; Guerineau, V.; Laprevote, O.; Vessieres, A.; Jaouen, G., Design of a New Multifunctionalized PAMAM Dendrimer with Hydrazide-Terminated Spacer Arm Suitable for Metalâˆ'Carbonyl Multilabeling of Aldehyde-Containing Molecules. *Macromolecules* 2007, 40, (24), 8568-8575.
17. Kobayashi, H.; Kawamoto, S.; Jo, S. K.; Sato, N.; Saga, T.; Hiraga, A.; Konishi, J.; Hu, S.; Togashi, K.; Brechbiel, M. W.; Star, R. A., Renal tubular damage detected by dynamic micro-MRI with a dendrimer-based magnetic resonance contrast agent. *Kidney Int* 2002, 61, (6), 1980-1985.
18. Kobayashi, H.; Saga, T.; Kawamoto, S.; Sato, N.; Hiraga, A.; Ishimori, T.; Konishi, J.; Togashi, K.; Brechbiel, M. W., Dynamic micro-magnetic resonance imaging of liver micrometastasis in mice with a novel liver macromolecular magnetic resonance contrast agent DAB-Am64-(1B4M-Gd)(64). *Cancer Res* 2001, 61, (13), 4966-4970.
19. Saad, M.; Garbuzenko, O. B.; Ber, E.; Chandna, P.; Khandare, J. J.; Pozharov, V. P.; Minko, T., Receptor targeted polymers, dendrimers, liposomes: which nanocarrier is the most efficient for tumor-specific treatment and imaging? *J Control Release* 2008, 130, (2), 107-14.
20. Fuchs, S.; Kapp, T.; Otto, H.; Schoneberg, T.; Franke, P.; Gust, R.; Schluter, A. D., A surface-modified dendrimer set for potential application as drug delivery vehicles: synthesis, in vitro toxicity, and intracellular localization. *Chemistry* 2004, 10, (5), 1167-92.
21. Kitchens, K. M.; El-Sayed, M. E.; Ghandehari, H., Transepithelial and endothelial transport of poly (amidoamine) dendrimers. *Adv Drug Deliv Rev* 2005, 57, (15), 2163-76.
22. Patil, M. L.; Zhang, M.; Taratula, O.; Garbuzenko, O. B.; He, H.; Minko, T., Internally cationic polyamidoamine PAMAM-OH dendrimers for siRNA delivery: effect of the degree of quaternization and cancer targeting. *Biomacromolecules* 2009, 10, (2), 258-66.
23. Chow, H.-F.; Leung, C.-F.; Xi, L.; Lau, L. W. M., Synthesis and Characterization of Outer Sphereâˆ'Outer Sphere Connected Organoplatinum Dendritic Networks from Surface-Difunctionalized and Surface-Trifunctionalized Dendritic Monomers. *Macromolecules* 2004, 37, (10), 3595-3605.
24. Kaminskas, L. M.; Boyd, B. J.; Karellas, P.; Krippner, G. Y.; Lessene, R.; Kelly, B.; Porter, C. J., The impact of molecular weight and PEG chain length on the systemic pharmacokinetics of PEGylated poly 1-lysine dendrimers. *Mol Pharm* 2008, 5, (3), 449-63.
25. Kono, K.; Akiyama, H.; Takahashi, T.; Takagishi, T.; Harada, A., Transfection activity of polyamidoamine dendrimers having hydrophobic amino acid residues in the periphery. *Bioconjug Chem* 2005, 16, (1), 208-14.
26. Majoros, I. J.; Keszler, B.; Woehler, S.; Bull, T.; Baker, J. R., Acetylation of Poly(amidoamine) Dendrimers. *Macromolecules* 2003, 36, (15), 5526-5529.
27. Majoros, I. J.; Thomas, T. P.; Mehta, C. B.; Baker, J. R., Jr., Poly(amidoamine) dendrimer-based multifunctional engineered nanodevice for cancer therapy. *J Med Chem* 2005, 48, (19), 5892-9.
28. Waite, C. L.; Sparks, S. M.; Uhrich, K. E.; Roth, C. M., Acetylation of PAMAM dendrimers for cellular delivery of siRNA. *BMC Biotechnol* 2009, 9, 38.
29. Qi, R.; Gao, Y.; Tang, Y.; He, R. R.; Liu, T. L.; He, Y.; Sun, S.; Li, B. Y.; Li, Y. B.; Liu, G., PEG-conjugated PAMAM Dendrimers Mediate Efficient Intramuscular Gene Expression. *Aaps J* 2009.
30. Kolhatkar, R. B.; Kitchens, K. M.; Swaan, P. W.; Ghandehari, H., Surface acetylation of polyamidoamine (PAMAM) dendrimers decreases cytotoxicity while maintaining membrane permeability. *Bioconjug Chem* 2007, 18, (6), 2054-60.

31. Antoni, P.; Nystrom, D.; Hawker, C. J.; Hult, A.; Malkoch, M., A chemoselective approach for the accelerated synthesis of well-defined dendritic architectures. *Chem Commun (Camb)* 2007, (22), 2249-51.
32. Mulders, S. J. E.; Brouwer, A. J.; van der Meer, P. G. J.; Liskamp, R. M. J., Synthesis of a novel amino acid based dendrimer. *Tetrahedron Letters* 1997, 38, (4), 631-634.
33. Goyal, P.; Yoon, K.; Weck, M., Multifunctionalization of dendrimers through orthogonal transformations. *Chemistry* 2007, 13, (31), 8801-10.
34. Steffensen, M. B., Simanek, E. E., Synthesis and manipulation of orthogonally protected dendrimers: building blocks for library synthesis. *Angew. Chem.* 2004, 116, 5290-5292.
35. Brauge, L.; Magro, G.; Caminade, A. M.; Majoral, J. P., First divergent strategy using two AB(2) unprotected monomers for the rapid synthesis of dendrimers. *J Am Chem Soc* 2001, 123, (27), 6698-9.
36. Oh, S.-K.; Kim, Y.-G.; Ye, H.; Crooks, R. M., Synthesis, Characterization, and Surface Immobilization of Metal Nanoparticles Encapsulated within Bifunctionalized Dendrimers. *Langmuir* 2003, 19, (24), 10420-10425.
37. Wu, P.; Malkoch, M.; Hunt, J. N.; Vestberg, R.; Kaltgrad, E.; Finn, M. G.; Fokin, V. V.; Sharpless, K. B.; Hawker, C. J., Multivalent, bifunctional dendrimers prepared by click chemistry. *Chem Commun (Camb)* 2005, (46), 5775-7.
38. Lim, J., Simanek, E. E., Synthesis of water-soluble dendrimers based on melamine bearing 16 paclitaxel groups. *Organic Letters* 2008, 10, 201-204.
39. Paleos, C. M.; Tsiourvas, D.; Sideratou, Z.; Tziveleka, L., Acid- and salt-triggered multifunctional poly(propylene imine) dendrimer as a prospective drug delivery system. *Biomacromolecules* 2004, 5, (2), 524-9.
40. Toli, L. P., Anderson, G. A., Smith, R. D., Brothers II, H. M., Spindler, R., Tomalia, D. A., Electrospray ionization Fourier transform ion cyclotron resonance mass spectrometric characterization of high molecular mass Starburst™ dendrimers. *International Journal of Mass Spectrometry and Ion Processes* 1997, 165-166, 405-418.
41. Woller, E. K.; Cloninger, M. J., The lectin-binding properties of six generations of mannose-functionalized dendrimers. *Org Lett* 2002, 4, (1), 7-10.
42. Duncan, R.; Izzo, L., Dendrimer biocompatibility and toxicity. *Adv Drug Deliv Rev* 2005, 57, (15), 2215-37.
43. Malik, N.; Wiwattanapatapee, R.; Klopsch, R.; Lorenz, K.; Frey, H.; Weener, J. W.; Meijer, E. W.; Paulus, W.; Duncan, R., Dendrimers: relationship between structure and biocompatibility in vitro, and preliminary studies on the biodistribution of 125I-labelled polyamidoamine dendrimers in vivo. *J Control Release* 2000, 65, (1-2), 133-48.
44. Kannan, S., Kolhe, P., Kannan, R. M., Lieh-lai, M., Glibatec, M, Effect of dendrimer end functionality on the cytotoxicity and the cellular drug delivery in lung epithelial cells. *Journal of Biomaterials Science: Polymers Edition* 2004, 15, 311-330.
45. Darbre, T.; Reymond, J.-L., Peptide Dendrimers as Artificial Enzymes, Receptors, and Drug-Delivery Agents. *Accounts of Chemical Research* 2006, 39, (12), 925-934.

TABLE 1

Library of PAMAM dendrimers with asymmetrical peripheral end groups obtained by Amino Acid Surface Modifications

| S. No | Dendrimer generation and end group | Amino Acid | Deprotection h/ Hydrolysis | Peripheral Functionality | Structure |
|---|---|---|---|---|---|
| 1 | G4-PAMAM-NH$_2$ | Boc-Ser-OH | — | OH, NHBoc | G4—HN—C(=O)—CH(NHBoc)—CH$_2$OH |
| 2 | G4-PAMAM-NH$_2$ | Boc-Ser-OH | Boc | OH, NH$_2$ | G4—HN—C(=O)—CH(NH$_2$)—CH$_2$OH |
| 3 | G4-PAMAM-NH$_2$ | Boc-Cys-OH | — | SH, NHBoc | G4—HN—C(=O)—CH(NHBoc)—CH$_2$SH |
| 4 | G4-PAMAM-NH$_2$ | Boc-Cys-OH | Boc | SH, NH$_2$ | G4—O—C(=O)—CH(NH$_2$)—CH$_2$SH |

TABLE 1-continued

Library of PAMAM dendrimers with asymmetrical peripheral end groups obtained by Amino Acid Surface Modifications

| S. No | Dendrimer generation and end group | Amino Acid | Deprotection h/ Hydrolysis | Peripheral Functionality | Structure |
|---|---|---|---|---|---|
| 5 | G3.5-PAMAM-COOH | H-Ser-OMe | — | OH, COOMe | 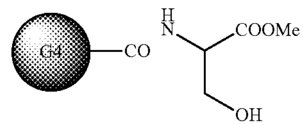 |
| 6 | G3.5-PAMAM-COOH | H-Ser-OMe | Me | OH, COOH | 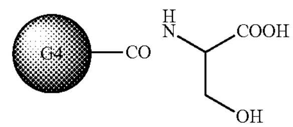 |
| 7 | G4-PAMAM-OH | Boc-Cys-OH | — | SH, NHBoc | 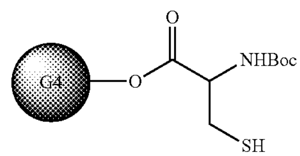 |
| 8 | G4-PAMAM-OH | Boc-Cys-OH | Boc | SH, $NH_2$ | 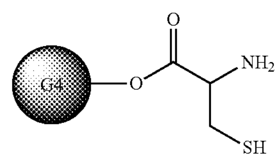 |
| 9 | G4-PAMAM-OH | Boc-Asp-OH | — | NHBoc, COOH | 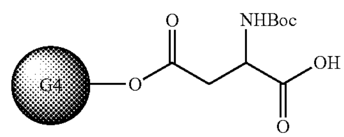 [SMILES: COC(=O)CC(NC(=O)OC(C)(C)C)C(=O)O] |
| 10 | G4-PAMAM-OH | Boc-Cys(S-TP)-OH | — | NHBoc, S-TP | 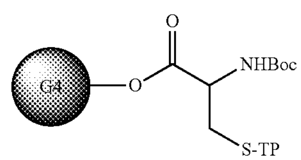 |
| 11 | G4-PAMAM-OH | Boc-Cys(S-TP)-OH | Boc | $NH_2$, S-TP | 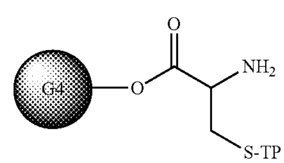 |

TABLE 2

Molecular weight estimation of amino acid modified PAMAM dendrimers

| Name of the compound | Mol. wt | No of amino acids attached | Total hetero- bi-functional peripheral groups | % Conversion | Purity of compound in % | Solubility Aqueous/ DMSO |
|---|---|---|---|---|---|---|
| G4-PAMAM- NH-CO- Ser(OH)-NHBoc | 24.5 kDa | 58 | 116 (58 + 58) | 91 | 98 | DMSO soluble |
| G4-PAMAM- NH-CO- Ser(OH)-$NH_2$ | 18.7 kDa* | 58 | 116 (58 + 58) | 91 | 96 | $H_2O$ soluble |
| G4-PAMAM- NH-CO- Cys(SH)-NHBoc | 24.8 kDa | 55 | 110 (55 + 55) | 86 | 96 | DMSO soluble |

TABLE 2-continued

Molecular weight estimation of amino acid modified PAMAM dendrimers

| Name of the compound | Mol. wt | No of amino acids attached | Total hetero-bi-functional peripheral groups | % Conversion | Purity of compound in % | Solubility Aqueous/DMSO |
|---|---|---|---|---|---|---|
| G4-PAMAM-NH-CO-Cys(SH)-NH$_2$ | 19.3 kDa* | 55 | 110 (55 + 55) | 86 | 95 | H$_2$O soluble |
| G3.5-PAMAM-CO-NH-Ser(OH)-COOMe | 17.2 kDa | 57 | 114 (57 + 57) | 89 | 97 | DMSO soluble |
| G3.5-PAMAM-CO-NH-Ser(OH)-COOH | 15.9 kDa* | 57 | 114 (57 + 57) | 89 | 96 | H$_2$O soluble |
| G4-PAMAM-O-CO-Cys(SH)-NH-Boc | 25.0 kDa* | 56 | 112 (64 + 64) | 87.5 | 96 | DMSO soluble |
| G4-PAMAM-O-CO-Cys(SH)-NH$_2$ | 19.2 kDa | 46 | 92 (46 + 46) | 72 | 98% | H$_2$O soluble |
| G4-PAMAM-O-CO-Asp(COOH)-NH-Boc | 25.7 kDa* | 56 | 112 (56 + 56) | 87.5 | 95% | DMSO soluble |
| G4-PAMAM-O-CO-Asp(COOH)-NH$_2$ | 18.99 kDa | 46 | 92 (46 + 46) | 72 | 96% | H$_2$O soluble |
| G4-PAMAM-O-CO-Cys(S-TP)-NH-Boc | 26.8 kDa | 42 | 84 (46 + 46) | 65.6 | 97% | DMSO soluble |
| G4-PAMAM-O-CO-Cys(S-TP)-NH$_2$ | 25.5 kDa | 38 | 76 (38 + 38) | 59 | 95% | DMSO soluble |

*Molecular weight determined by MALDI-TOF

TABLE 3

Particle size and zeta potential hetero-bifunctional dendrimers

| Name of the sample | Sample Particle diameter (nm) | Zeta Potential (mV) |
|---|---|---|
| G4-PAMAM-NH$_2$ | 4.70 | +11.5 |
| G3.5-PAMAM-COOH | 4.20 | −9.30 |
| G4-PAMAM-OH | 4.78 | −2.10 |
| G4-PAMAM-NH-Ser(OH)-NH$_2$ | 5.65 | −1.83 |
| G4-PAMAM-NH-Cys(SH)NH$_2$ | 6.21 | +4.80 |
| G3.5-PAMAM-CO-Ser(OH)-COOH | 6.56 | +8.83 |
| G4-PAMAM-OH-Cys(SH)-NH$_2$ | 6.01 | 3.60 |
| G4-PAMAM-Asp(COOH)-NH$_2$ | 5.59 | +1.51 |

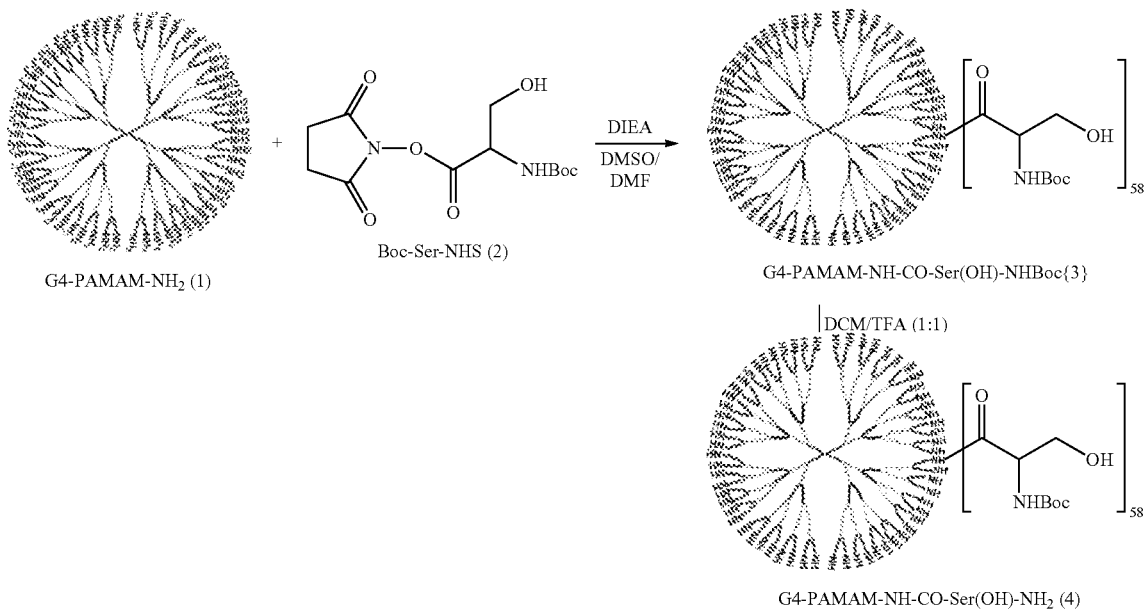

Scheme-1

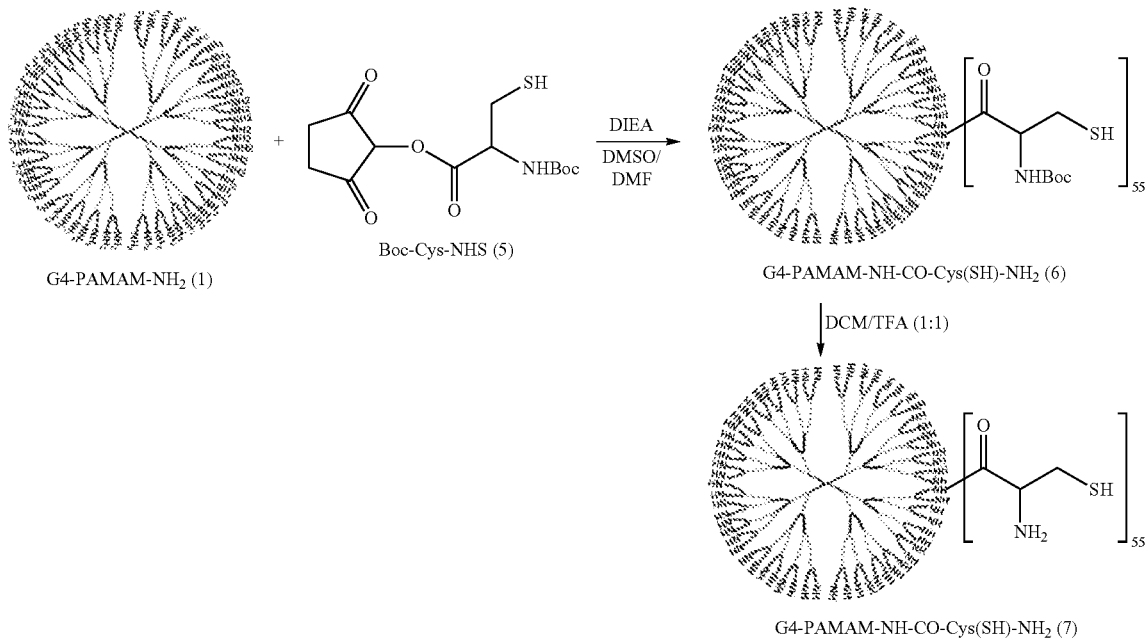
Schemes 1-2. Schematic representation for synthesis of G4-PAMAM-NH—CO-Ser(OH)-NHBoc (3), and G4-PAMAM-NH—CO-Cys(SH)-NHBoc (6) Compounds (3 and 6) show the conversion of symmetric peripheral amines of G4-PAMAM-NH$_2$ (1) into hetero bifunctional terminal groups 'OH+NHBoc' and 'SH+NHBoc' respectively. The compounds (3, 6) on deprotection of Boc group gave OH+NH$_2$' and 'SH+NH$_2$' respectively.
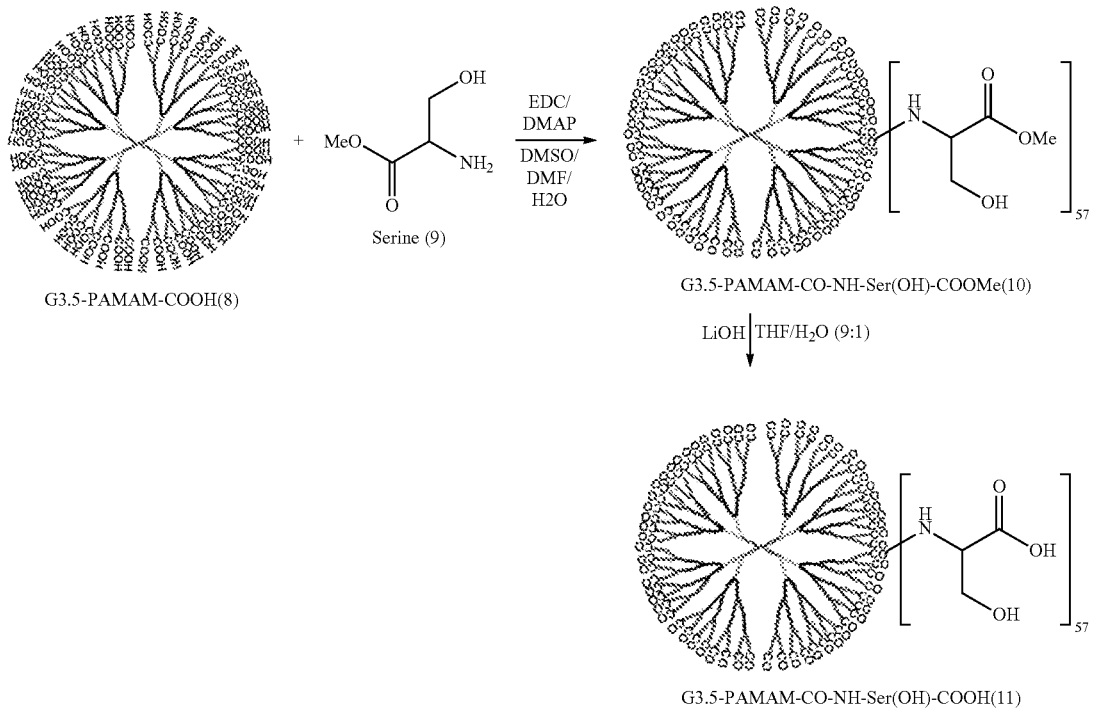

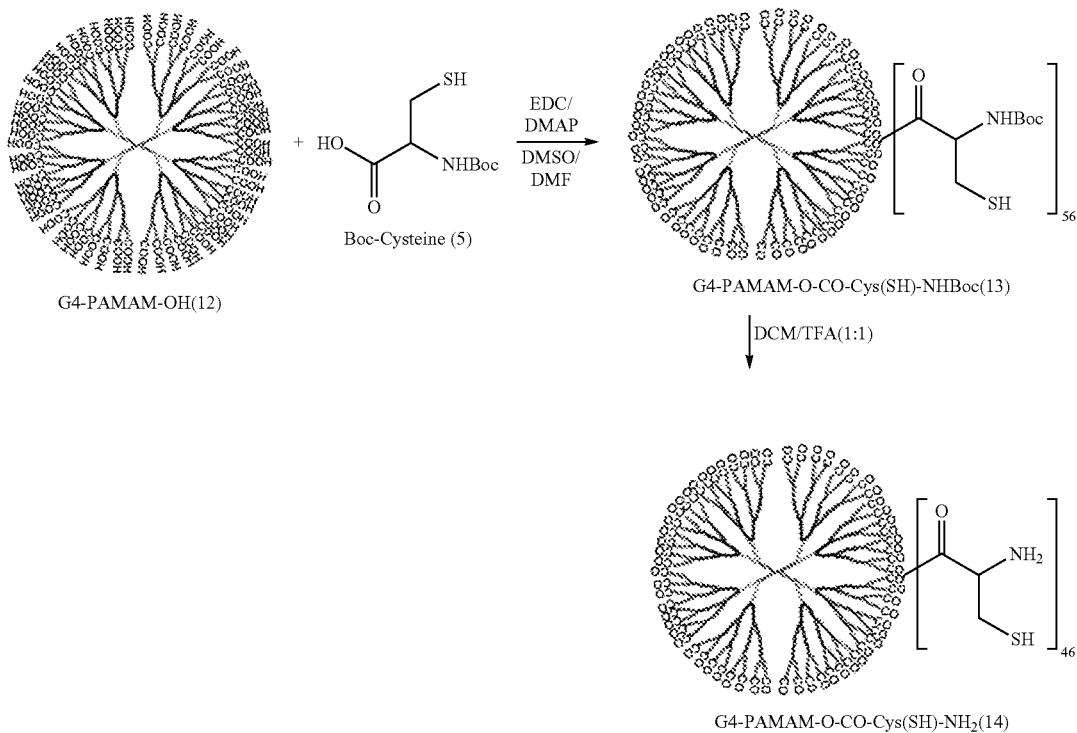

Schemes 3-4. Schematic representation for synthesis of G3.5-PAMAM-CO—NH-Ser(OH)—COOMe (10) and G4-PAMAM-O—CO-Cys(SH)-NHBoc (13) Compounds (10 and 13) show the conversion of symmetric peripheral acid of G3.5-PAMAM-NH₂ (8) into hetero bifunctional terminal groups 'COOMe+OH' and 'SH+NHBoc' respectively. The compounds 10, 13 was further hydrolysis of methyl ester and Boc gave compounds 'COOH+OH' and 'SH+NH₂' respectively.

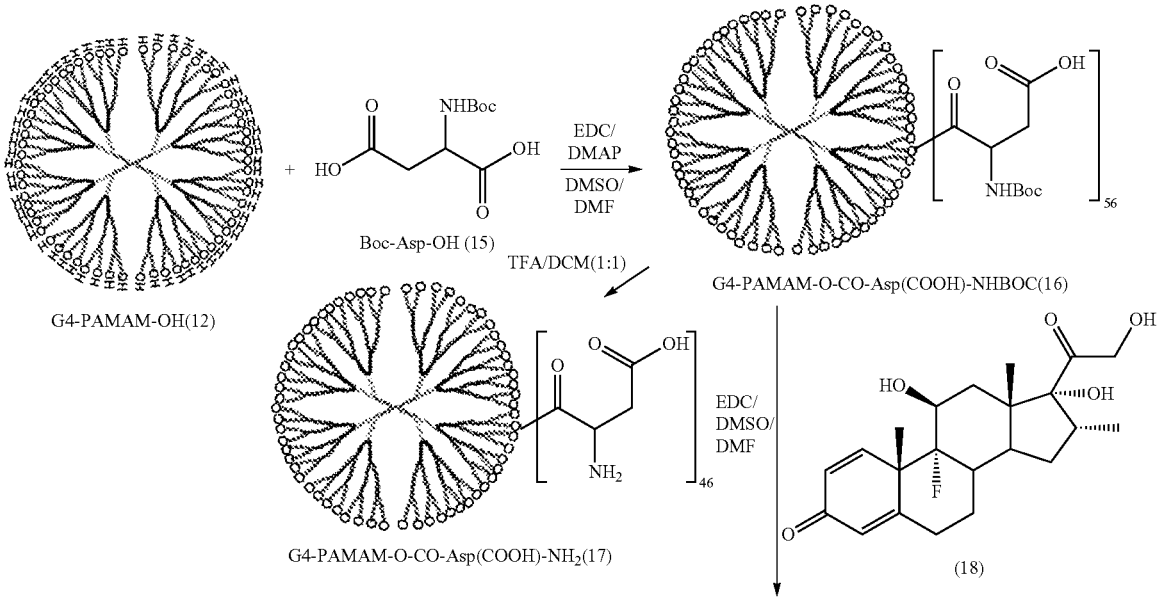

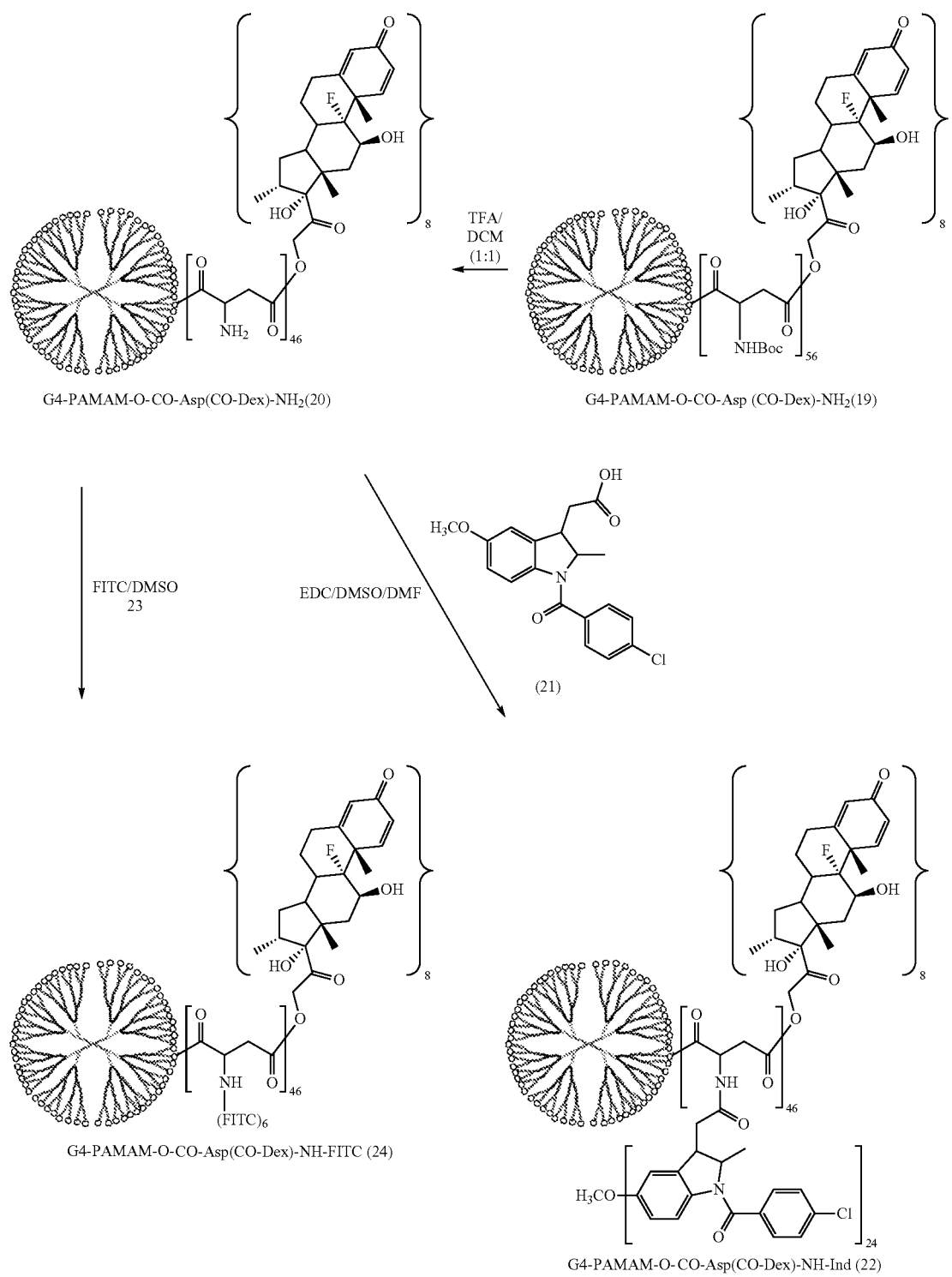

Scheme 5. Schematic representation for the post-functionalization reactions of hetero-bifunctional dendrimers showing conjugation of multiple drugs and or imaging agents in immediate succession. G4-PAMAM-O-Asp(COOH)—NH₂ (17) dendrimer bearing COOH and NH₂ termini was synthesized. Dexamethasone was conjugated to G4-PAMAM-O-Asp(COOH)—NH₂ (16) and indomethacin was added to achieve G4-PAMAM-O-Asp(CO-Dex)-NH-Ind (22). Similarly, FITC was conjugated in immediate succession to G4-PAMAM-O-Asp(CO-Dex)-NH₂ (20) to yield G4-PAMAM-O-Asp(CO-Dex)-NH-FITC (24).

Scheme-6
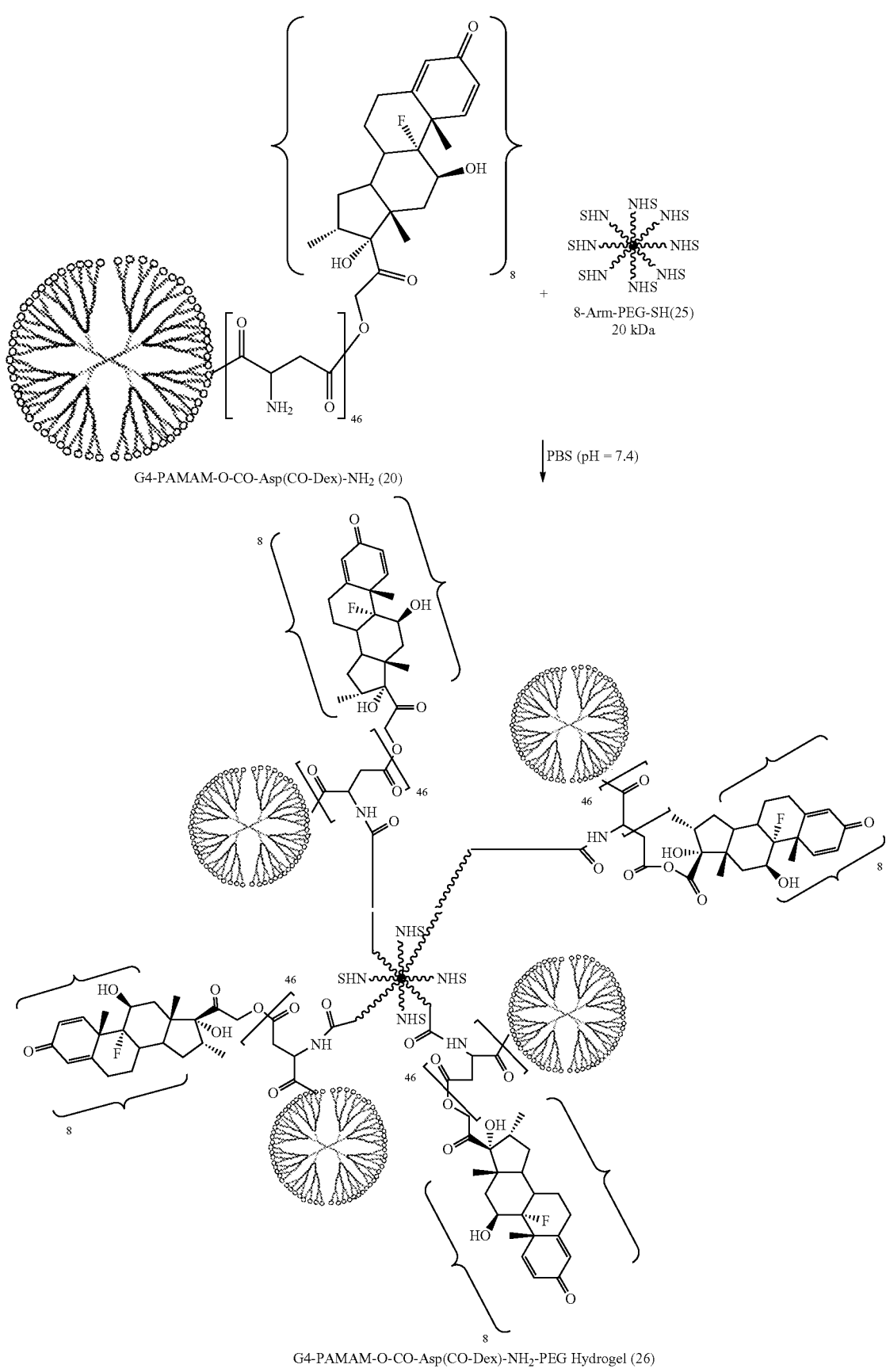

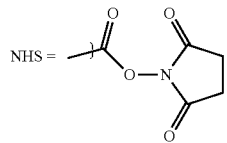
Scheme 6. Schematic representation for the post-functionalization reactions of hetero-bifunctional dendrimers showing conjugation of drug (e.g. dexamethasone) to one functional handle while the other functional handle is used for hydrogel formation (26) with N-hydroxysuccinmide terminated 8-arm-polyethylene glycol (25).
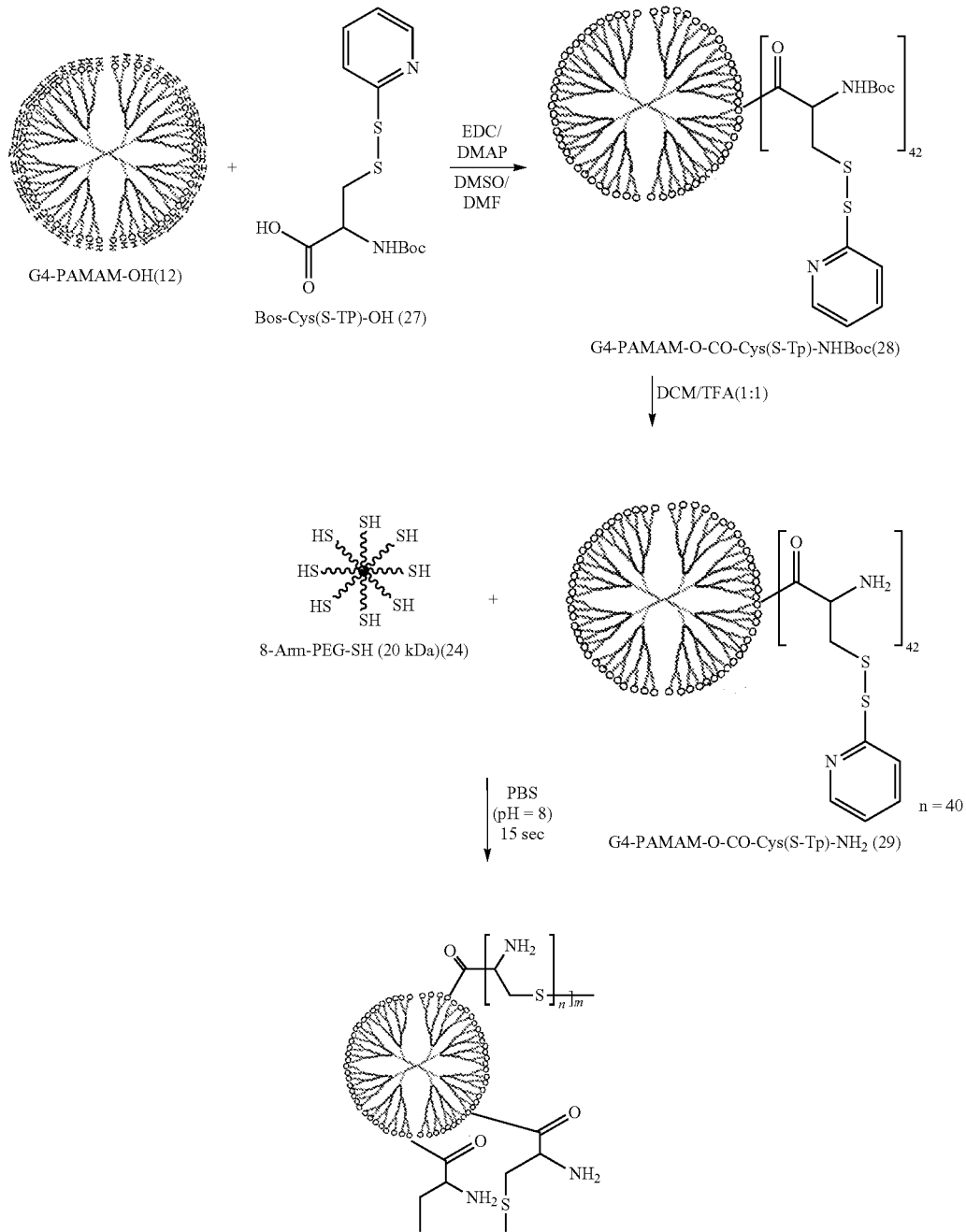

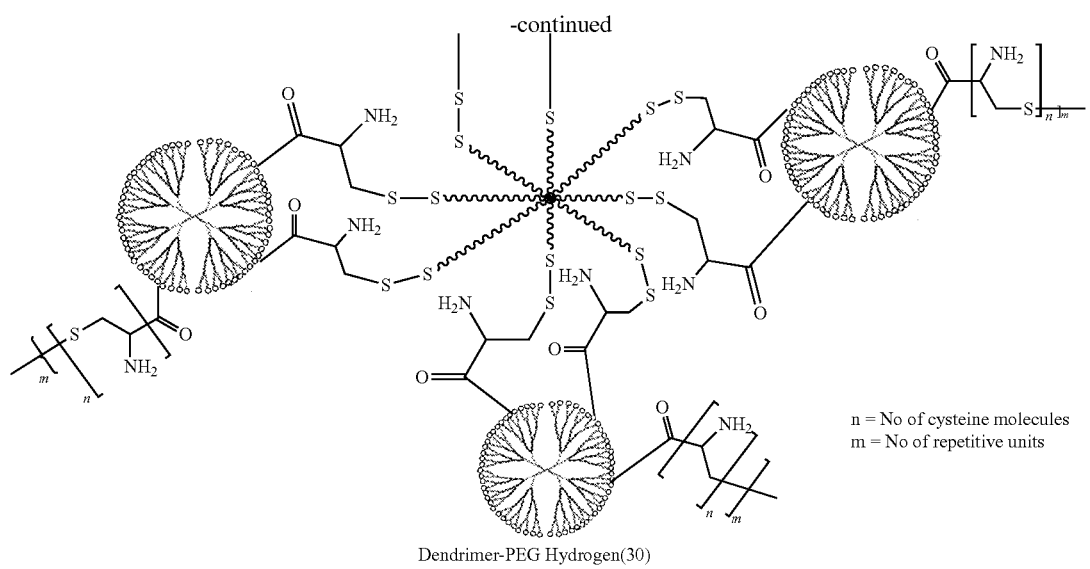

Dendrimer-PEG Hydrogen(30)

n = No of cysteine molecules
m = No of repetitive units

Scheme 7. Schematic representation for the formation of hydrogel involving one of the functional handles of the G4-PAMAM-O—CO-Cys(S-TP)—NH$_2$ dendrimer while the 'NH$_2$' handle is available for further modifications. The thiol terminated 8arm PEG (20 kDa) formed gel at pH 7.4 by reacting with the thiopyridine terminations of the G4-PAMAM-O—CO-Cys(S-TP)-NH$_2$ resulting in disulfide linkages.

Scheme-8

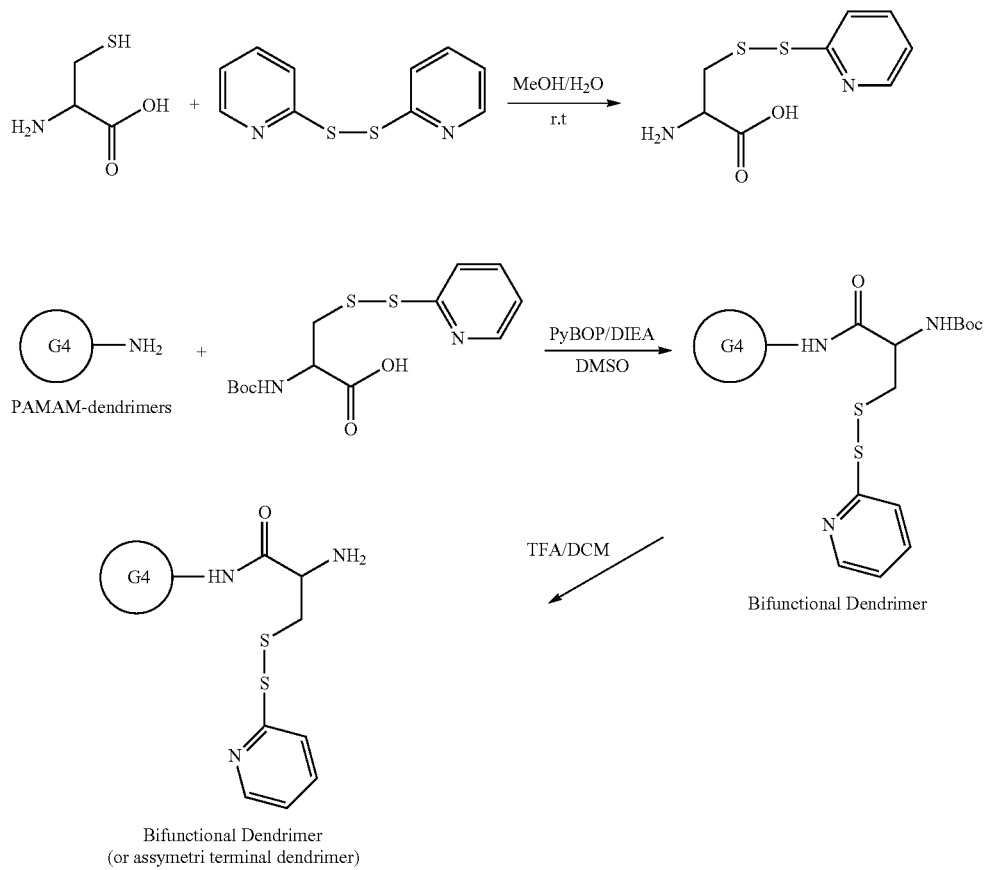

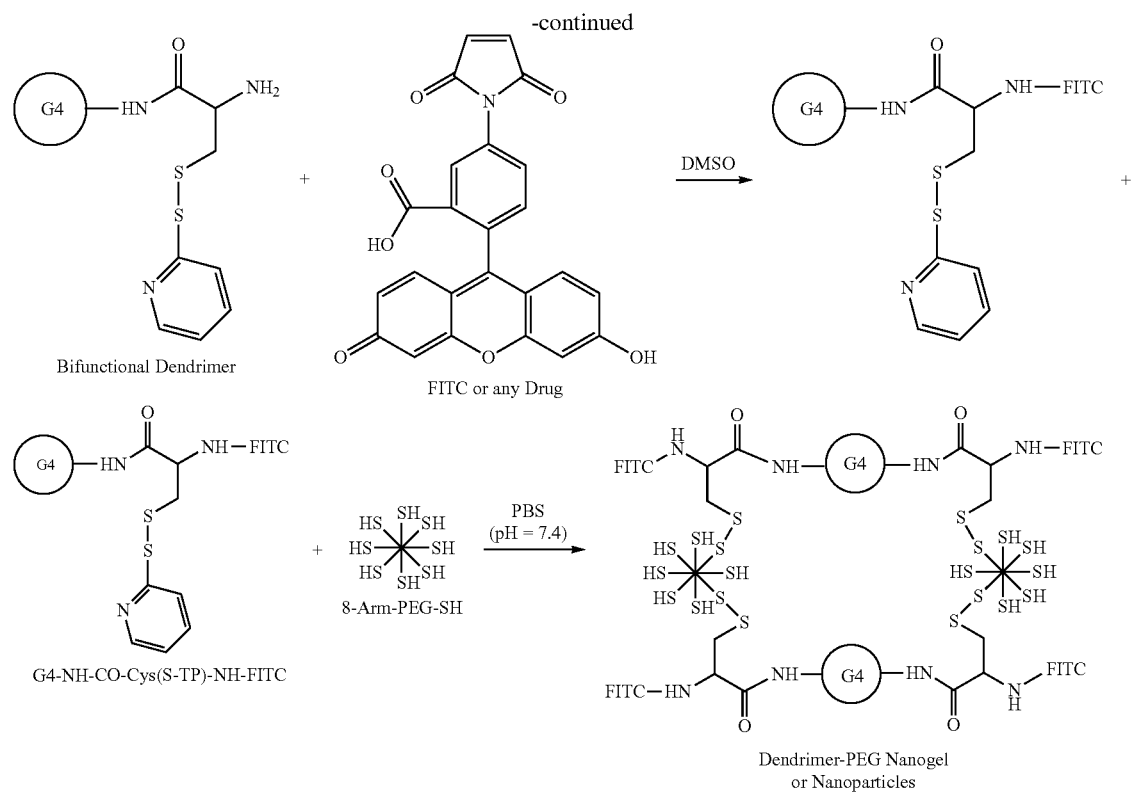
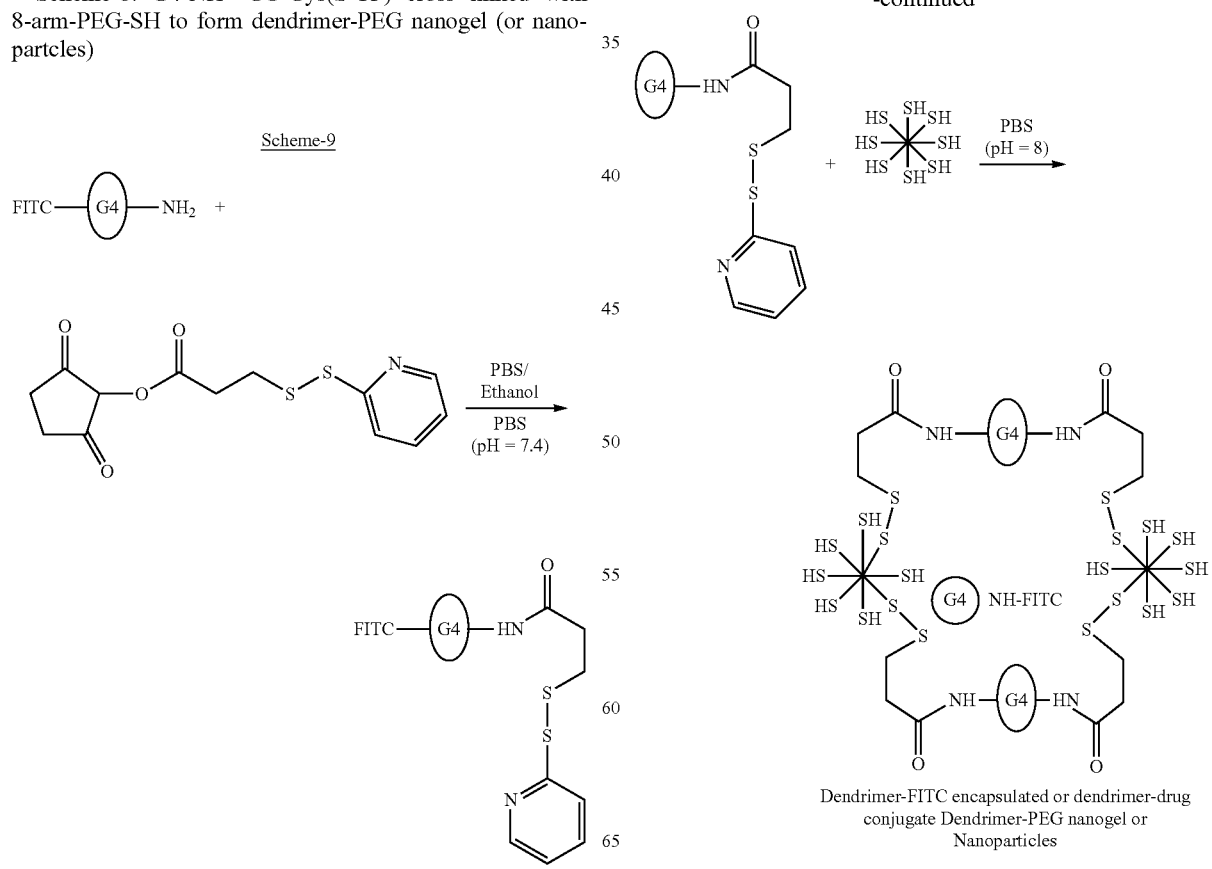
Scheme-8. G4-NH—CO-Cys(S-TP) cross linked with 8-arm-PEG-SH to form dendrimer-PEG nanogel (or nanopartcles)
Dendrimer-FITC encapsulated or dendrimer-drug conjugate Dendrimer-PEG nanogel or Nanoparticles Scheme-10
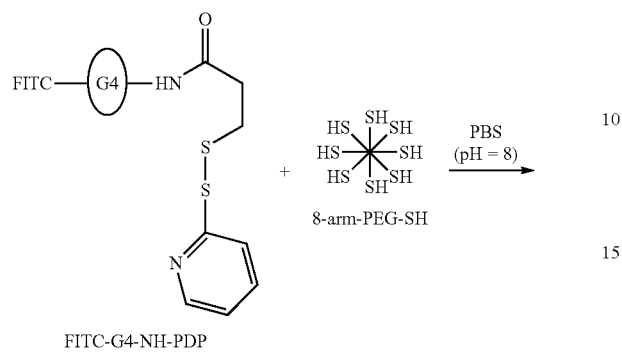
FITC-G4-NH-PDP
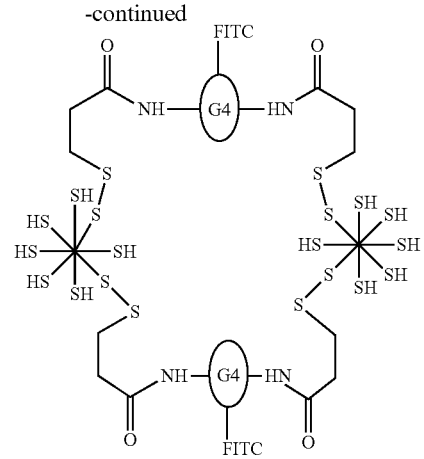
Dendrimer-FITC Covalently linked or any drug
Dendrimer-PEG Nanogel or Nanoparticles
Scheme-9. G4-NH-PDP cross linked with 8-arm-PEG-SH to form G4-FITC encapsulated dendrimer-PEG nanogel (or nanopartcles).
Scheme-10: FITC-G4-NH-PDP cross linked with 8-arm-PEG-SH to form dendrimer-PEG nanogel (or nanopartcles)
Scheme-11
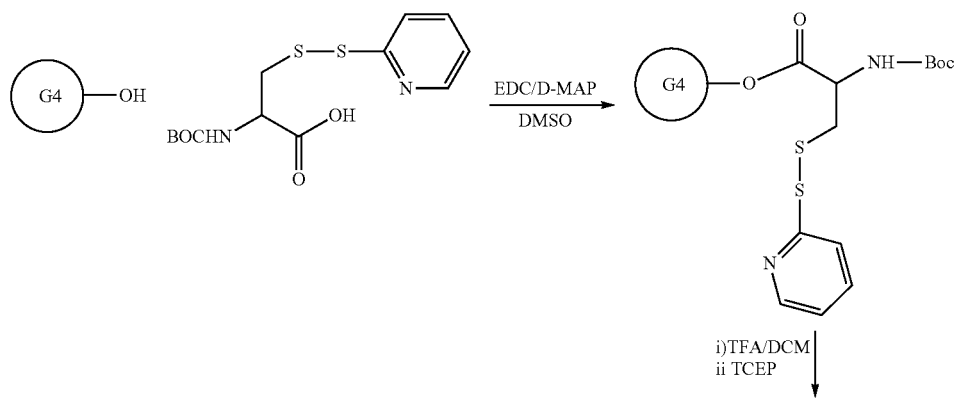
Amine Thiol Fuctionalized Dendrimers
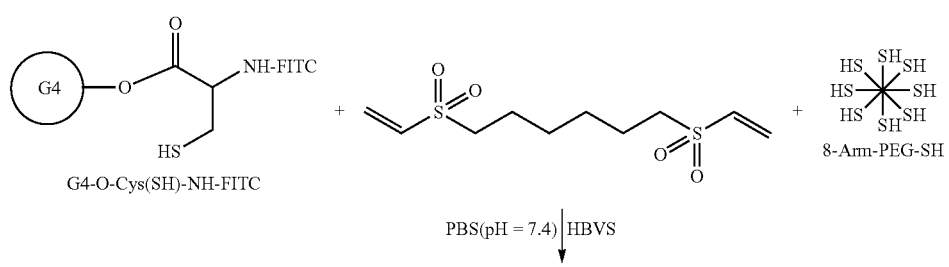

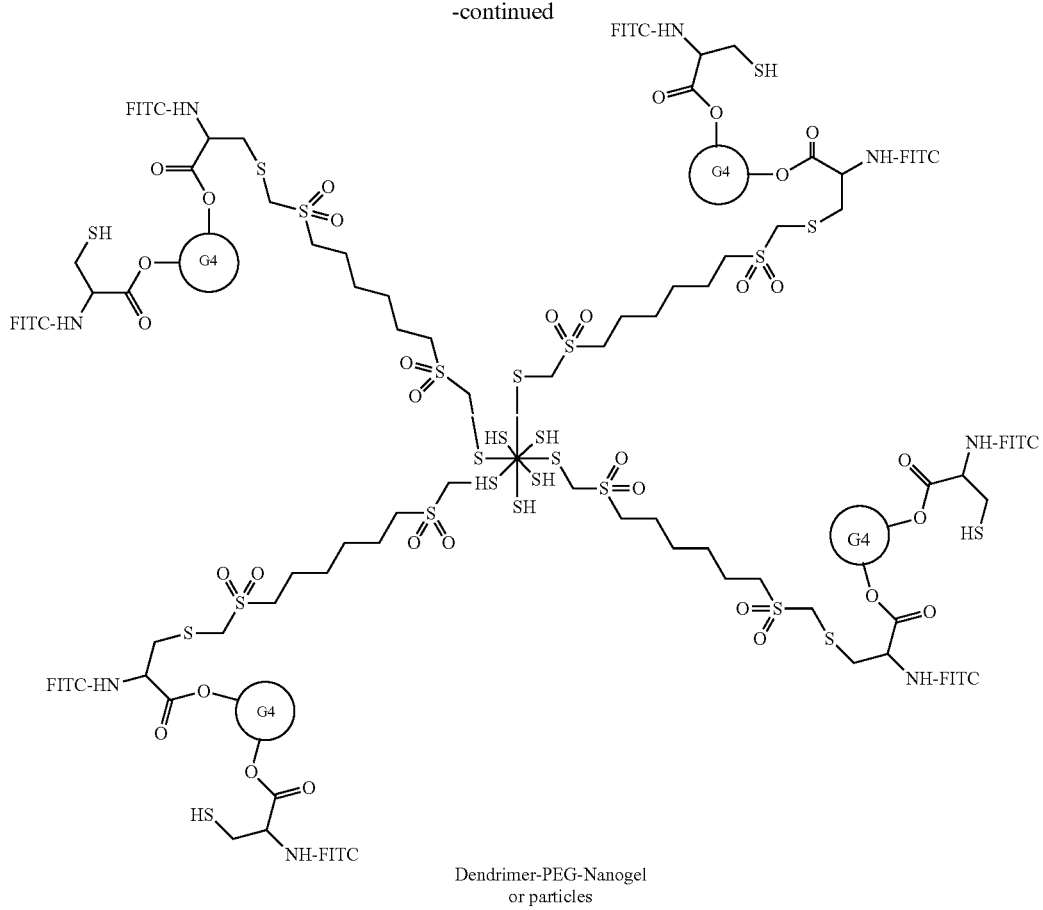
Dendrimer-PEG-Nanogel or particles
Scheme-11: HBVS cross linked with G4-O-Cys(SH)—NH—FITC and 8-arm-PEG-SH to form dendrimer-PEG nanogel (or nanopartcles)
Scheme-12
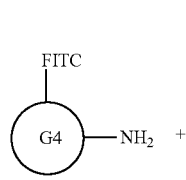
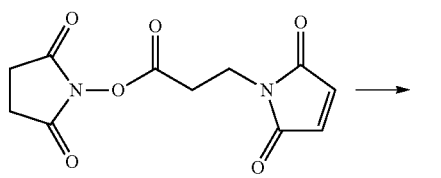
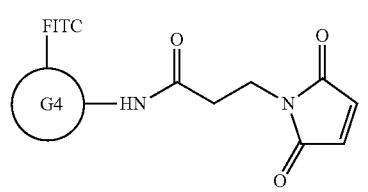
Dendrimer-FITC Covalently linked Dendrimer-PEG nanogel or Particles Scheme-12: FITC-G4-NH-Mal cross linked with 8-arm-PEG-SH to form dendrimer-PEG nanogel (or nanopartcles)
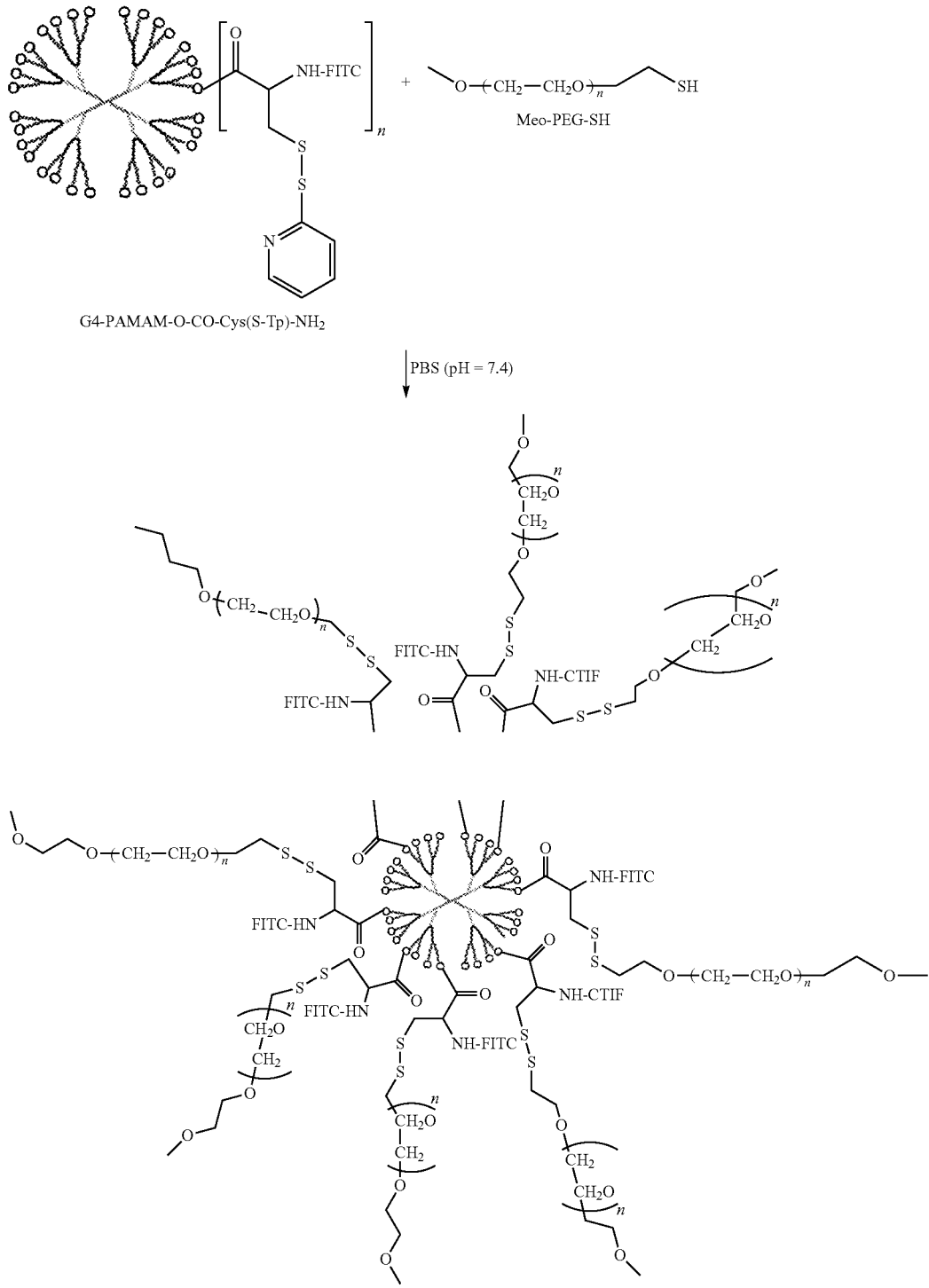
n = 40

Scheme-13: G4-O—CO-Cys(S-Tp)-NH$_2$ cross linked with Meo-PEG-SH to form dendrimer-PEG nanogel (or nanopartcles)
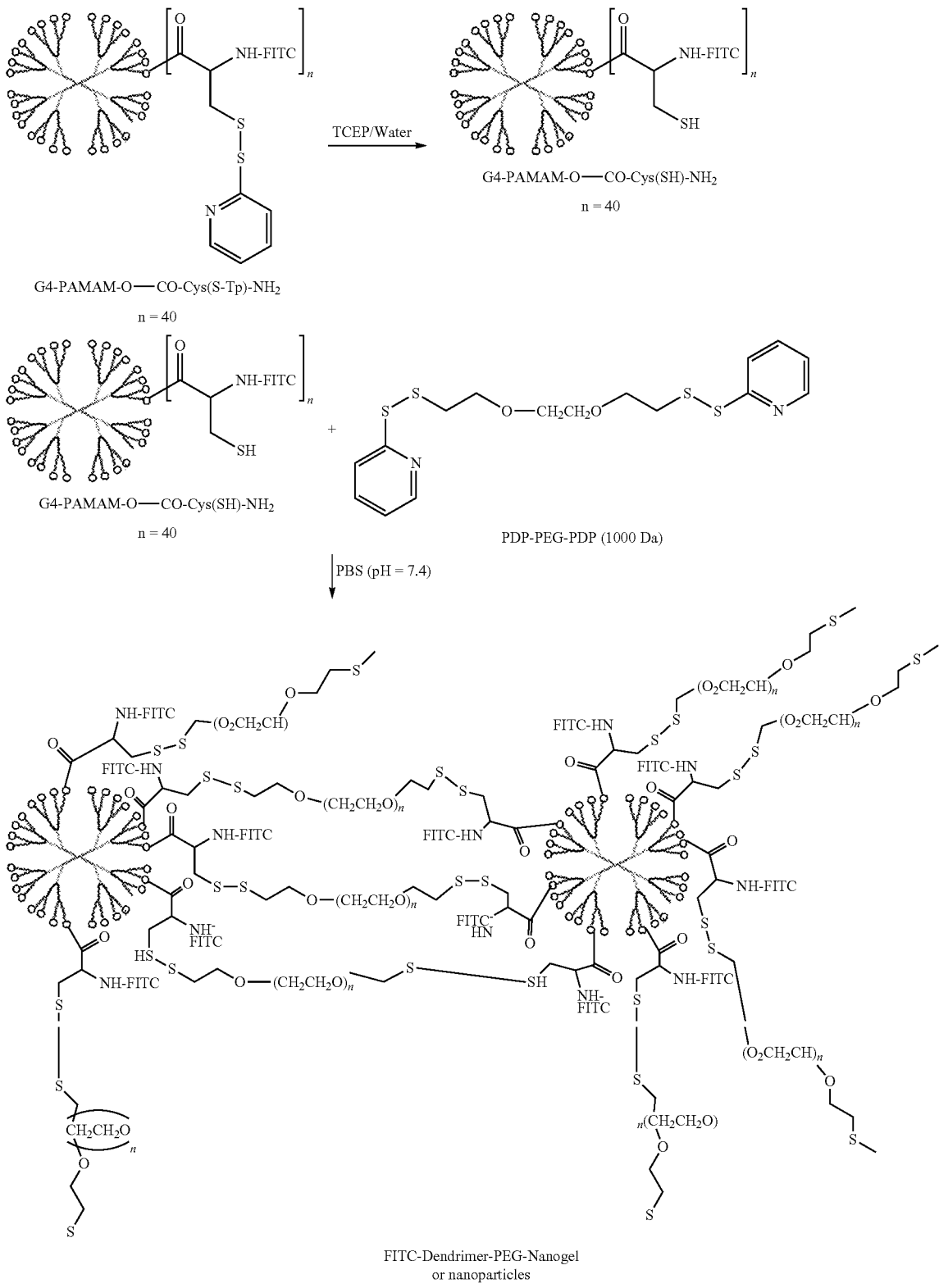

Scheme-14: G4-O—CO-Cys(SH)—NH₂ cross linked with PDP-PEG-PDP to form dendrimer-PEG nanogel (or nanopartcles)
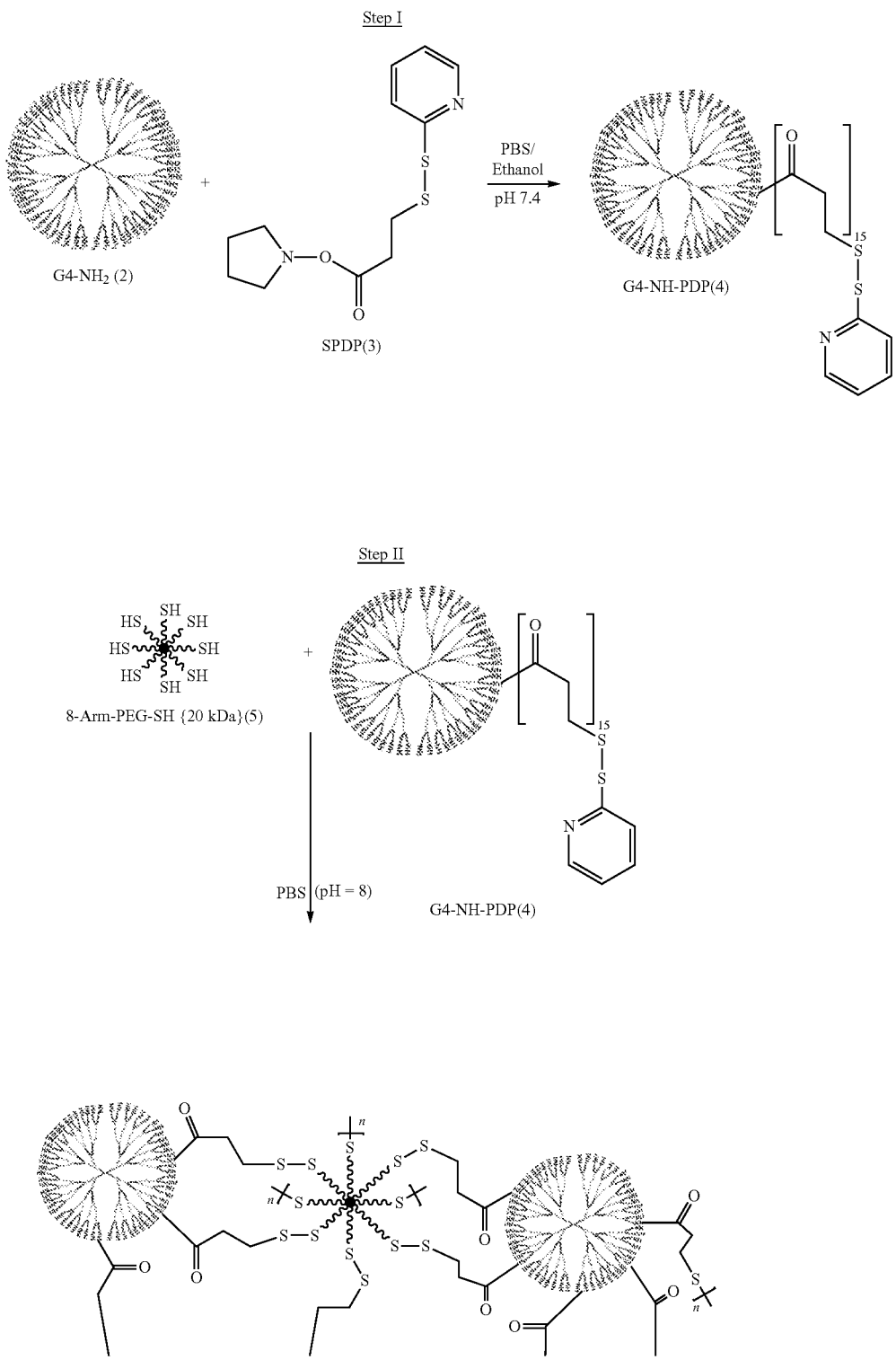

-continued

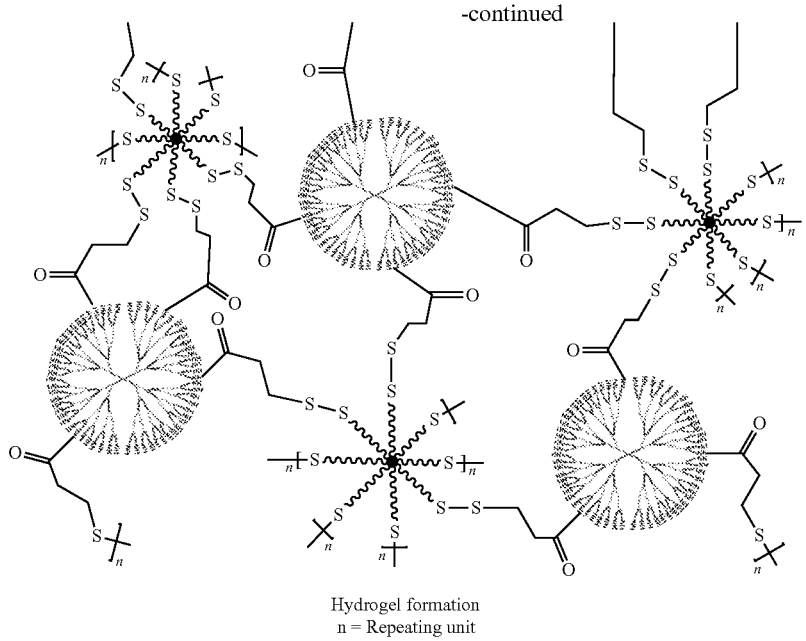

Hydrogel formation
n = Repeating unit

Scheme 15 Schematic representation for the formation of hydrogel. The thiol terminated 8-arm PEG (20 kDa) formed gel at pH 7.4 by reacting with the dithiopyridine terminations of the G4-NH-PDP resulting in disulfide linkages.

What is claimed is:

1. An injectable hydrogel nanoparticle comprising:
a plurality of poly(amidoamine) (PAMAM) dendrimers with an end group covalently bound to an amino acid linker selected from the group consisting of serine, aspartic acid, cysteine, glutamic acid, threonine, and tyrosine,
wherein the amino acid linker is covalently bound by a first functional group to a crosslinkable polymer and is covalently bound by a second, different functional group to a drug or imaging agent;
wherein the hydrogel nanoparticle is formed by crosslinking of the crosslinkable polymer.

2. The injectable hydrogel nanoparticle of claim 1 wherein the amino acid is in a protected form selected from the group consisting of tert-butylcarbonyl-serine-hydroxysuccinimide (Boc-Ser-NHS), tert-butylcarbonyl-aspartic acid (Boc-Asp-OH), tertbutylcarbonyl-glutamic acid (Boc-Glu-OH), fluorenylmethoxycarbonyl-serine (Fmoc-Ser), fluorenylmethoxycarbonyl-aspartic acid (Fmoc-Asp-OH), fluorenylmethoxycarbonyl-glutamic acid (Fmoc-Glu-OH), tert-butylcarbonylcysteine-hydroxysuccinimide (Boc-Cys-NHS), serine-methylester (H-ser-OMe), cysteine-methylester (H-Cys-OMe), aspartic acid-methylester (H-Asp-OMe), glutamic acid-methyl ester (H-Glu-OMe), tert-butylcarbonyl-threoninehydroxysuccinimide (Boc-Thr-NHS), threonine-methylester (H-Thr-OMe), fluorenylmethoxycarbonyl-threonine (Fmoc-Thr), tert-butylcarbonyl-tyrosinehydroxysuccinimide (Boc-Tyr-NHS), tert-butylcarbonyl-tyrosine (Boc-Tyr-OH), tyrosine-methylester (H-Tyr-OMe), cysteine-dithiopyridine (Cys-S-STP), and tertbutylcarbonyl-cysteine-dithiopyridine (Boc-Cys-S-STP) when it is covalently bound prior to attachment of the crosslinkable polymer and the drug or imaging agent.

3. The injectable hydrogel nanoparticle of claim 1, wherein the crosslinkable polymer is selected from the group consisting of a linear polymer, a branched polymer, and a star shaped polymer.

4. The injectable hydrogel nanoparticle of claim 1, wherein the diameter of the nanoparticle is between 5 nm and 10 μm.

5. The injectable hydrogel nanoparticle of claim 1, formulated for intravenous, topical, intravitreal, intramuscular, or subcutaneous administration.

6. The injectable hydrogel nanoparticle of claim 1, wherein the PAMAM dendrimer is a G4 PAMAM dendrimer.

7. The injectable hydrogel nanoparticle of claim 1, wherein the drug is selected from the group consisting of macrolide antibiotics, tetracyclines, fluoroquinolones, cephalosporins, non-steroidal anti-inflammatory and analgesic drugs, and corticosteroids.

8. The injectable hydrogel nanoparticle of claim 3, wherein the crosslinkable polymer is a functionalized polyethylene glycol (PEG) polymer.

9. The injectable hydrogel nanoparticle of claim 8, wherein the functionalized PEG polymer is between 5 kDa and 80 kDa in size.

10. The injectable hydrogel nanoparticle of claim 8, wherein the functionalized PEG polymer is between 20 and 40 kDa in size.

11. The injectable hydrogel nanoparticle of claim 7, wherein the drug is selected from the group consisting of erythromycin, azithromycin, rapamycin, clarithromycin, minocycline, doxycycline, ciprofloxacin, enrofloxacin, ofloxacin, gatifloxacin, levofloxacin, norfloxacin, cefuroxime, cefaclor, cephalexin, cephadroxil, cepfodoxime proxetil, N-acetyl cysteine, ibuprofen, aspirin, acetaminophen, diclofenac sodium, fluocinolone acetonide, and methylprednisolone.

* * * * *

UNITED STATES PATENT AND TRADEMARK OFFICE
CERTIFICATE OF CORRECTION

| | | |
|---|---|---|
| PATENT NO. | : 9,526,794 B2 | Page 1 of 1 |
| APPLICATION NO. | : 13/636715 | |
| DATED | : December 27, 2016 | |
| INVENTOR(S) | : Kannan Rangaramanujam et al. | |

It is certified that error appears in the above-identified patent and that said Letters Patent is hereby corrected as shown below:

On the Title Page

Item (86) PCT No., replace "PCT/JP2011/030648" with --PCT/US2011/030648--.

Signed and Sealed this
Second Day of May, 2017

Michelle K. Lee
*Director of the United States Patent and Trademark Office*